(12) United States Patent
Bullinga

(10) Patent No.: US 6,993,388 B2
(45) Date of Patent: Jan. 31, 2006

(54) SYSTEM AND METHOD FOR ASSESSMENT OF CARDIAC ELECTROPHYSIOLOGIC STABILITY AND MODULATION OF CARDIAC OSCILLATIONS

(75) Inventor: John R. Bullinga, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 10/884,276

(22) Filed: Jul. 2, 2004

(65) Prior Publication Data

US 2005/0004608 A1    Jan. 6, 2005

Related U.S. Application Data

(60) Provisional application No. 60/484,860, filed on Jul. 3, 2003.

(51) Int. Cl.
*A61N 1/00* (2006.01)
(52) U.S. Cl. .......................................................... 607/9
(58) Field of Classification Search ............. 607/9–28; 600/508–521
See application file for complete search history.

(56) References Cited

U.S. PATENT DOCUMENTS

| | | | |
|---|---|---|---|
| 4,791,936 A * | 12/1988 | Snell et al. .................. 600/510 |
| 4,802,491 A | 2/1989 | Cohen et al. | |
| 5,437,285 A | 8/1995 | Verrier et al. | |
| 5,549,652 A * | 8/1996 | McClure et al. ............... 607/28 |
| 5,560,370 A | 10/1996 | Verrier et al. | |
| 5,713,367 A | 2/1998 | Arnold et al. | |
| 5,861,009 A | 1/1999 | Armstrong et al. | |
| 5,921,940 A | 7/1999 | Verrier et al. | |
| 5,935,082 A | 8/1999 | Albrecht et al. | |
| 6,021,345 A | 2/2000 | Karagueuzian et al. | |
| 6,169,919 B1 | 1/2001 | Nearing et al. | |
| 6,370,431 B1 | 4/2002 | Stoop et al. | |
| 6,400,982 B2 | 6/2002 | Sweeney et al. | |
| 6,445,947 B1 | 9/2002 | Hoium et al. | |
| 6,453,191 B2 | 9/2002 | Krishnamachari | |
| 6,456,880 B1 | 9/2002 | Park et al. | |
| 6,473,647 B1 | 10/2002 | Bradley | |
| 2001/0007948 A1 | 7/2001 | Stoop et al. | |
| 2001/0010009 A1 | 7/2001 | Bakels et al. | |
| 2002/0138106 A1 | 9/2002 | Christini et al. | |
| 2002/0151811 A1 | 10/2002 | Starobin et al. | |

OTHER PUBLICATIONS

Schwab et al., "Incidence of T Wave Alternation After Acute Myocardial Infarction and Correlation with Other Prognostic Parameters: Results of a Prospective Study", *Journal of Pacing and Clinical Electrophysiology*, Jun. 2001, pp. 957-961.

Ikeda et al., "T-Wave Alternans as a Predictor for Sudden Cardiac Death After Myocardial Infarction", *Journal of the American College of Cardiology* vol. 89, Jan. 1, 2002, pp. 79-82.

(Continued)

*Primary Examiner*—Scott M. Getzow
(74) *Attorney, Agent, or Firm*—Fay Kaplun & Marcin, LLP

(57) ABSTRACT

Described is a method of delivering a pacing pattern to a heart, measuring a response of the heart to the pacing pattern, the measured response including a series of electrograms representing a plurality of heartbeats of the pacing pattern and calculating diagnostic data from the measured response, wherein the diagnostic data includes data in one of a time domain and a frequency domain.

44 Claims, 44 Drawing Sheets

OTHER PUBLICATIONS

Pastore et al., :Mechanism Linking T-Wave Alternans to the Genesis of Cardiac Fibrillation, *Circulation*, Mar. 16, 1999, pp. 1385-1394.

Gold et al., "A Comparison of T-Wave Alternans, Signal Averaged Electrocardiography and Programmed Ventricular Stimulation for Arrhythmia Risk Stratification", Journal of the American College of Cardiology, Dec. 2000, pp. 2247-2253.

Pastore et al., "Role of Structural Barriers in the Mechanism of Alternans-Induced Reentry", *Circulation Research*, Dec. 22, 2000, pp. 1157-1163.

\* cited by examiner

| Loop 1 | | Loop 2 | |
|---|---|---|---|
| A | B | A | B |
| 545 | 555 | 545 | 555 |

| Loop 1 | | | | Loop 2 | | | |
|---|---|---|---|---|---|---|---|
| A | B | C | D | A | B | C | D |
| 535 | 575 | 555 | 555 | 535 | 575 | 555 | 555 |

| Loop 1 | | | Loop 2 | | |
|---|---|---|---|---|---|
| A | B | C | A | B | C |
| 545 | 555 | 555 | 545 | 555 | 555 |

| Loop 1 | | | Loop 2 | | |
|---|---|---|---|---|---|
| A | B | C | A | B | C |
| 565 | 555 | 545 | 565 | 555 | 545 |

| Loop 1 | | | Loop 2 | | |
|---|---|---|---|---|---|
| A | B | C | A | B | C |
| 535 | 535 | 555 | 535 | 535 | 555 |

Repolarization Detection -- 150

Patient 1, Impact from Beat A to Beat B1

Patient 2, Impact from Beat A to Beat B1

Patient 1, Impact from Beat B2 to Beat B3

Patient 2, Impact from Beat B2 to Beat B3

Patient 1, Responses for each Beat

Patient 2, Responses for each Beat

Patient Characterization Options:
☐ Steady State Response, ☐ Resonant Pacing Response,
☐ Non-Resonant Pacing Response, ☐ Template of Responses First Mode: ☐ Monitor, ☐ Magnitude Control, ☐ Phase Control
Second Mode: ☐ Monitor, ☐ Magnitude Control, ☐ Phase Control
Third Mode: ☐ Monitor, ☐ Magnitude Control, ☐ Phase Control

Alternans Detection Response
Auto Heart Rate Maximum Limit: On/Off, Range: ☐ to ☐
Alternans Mode Switch Queue: Rate/Threshold, Alt/Arrhythmia Premature Beat Response: Characterize: On/Off
Premature Beat Overdrive: On/Off, Range: ☐ to ☐
Rate Smoothing: On/Off

Fig. 25

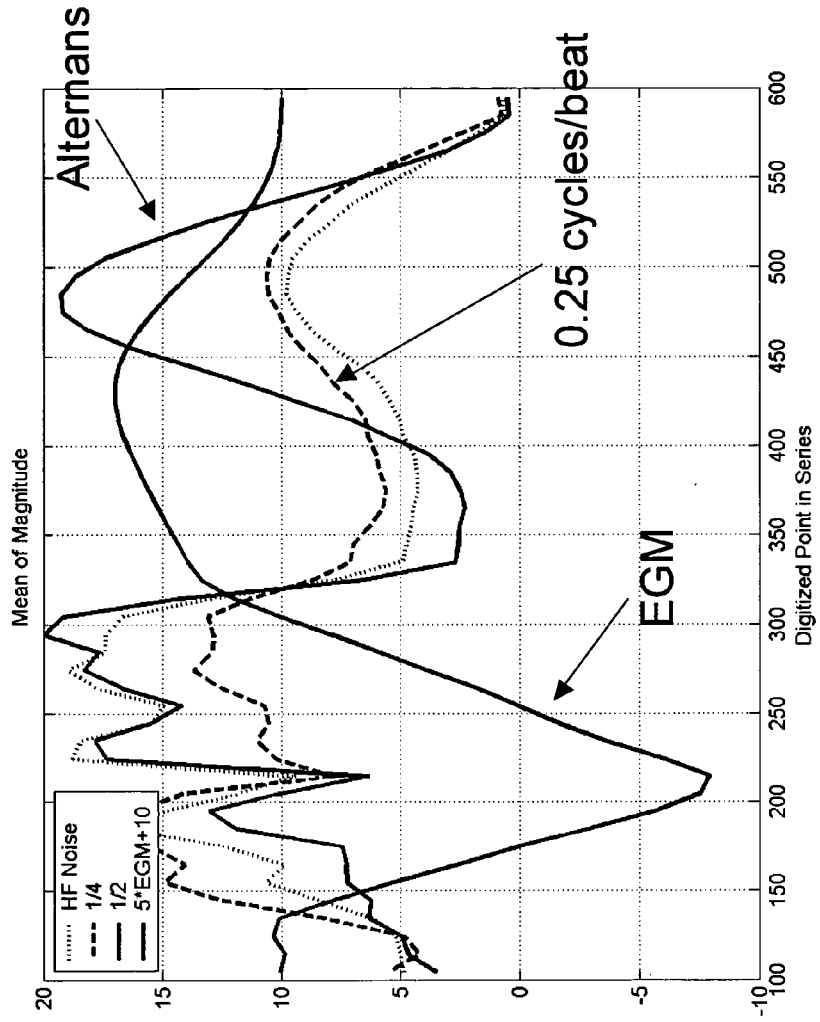
Fig. 29b RP: Patient with Heart Failure, CAD

RP: Patient with Heart Failure, CAD

US 6,993,388 B2

SYSTEM AND METHOD FOR ASSESSMENT OF CARDIAC ELECTROPHYSIOLOGIC STABILITY AND MODULATION OF CARDIAC OSCILLATIONS

PRIORITY/INCORPORATION BY REFERENCE

The present application claims priority to U.S. patent application No. Ser. 60/484,860 entitled "System and Method for Assessment of Cardiac Electrophysiologic Stability and Modulation of Cardiac Oscillations" filed on Jul. 3, 2003, the specification of which is expressly incorporated, in its entirety, herein.

BACKGROUND INFORMATION

Heart disease accounts for more deaths in the United States than any other disease. Sudden cardiac death ("SCD") accounts for approximately 400,000 deaths and heart failure accounts for approximately 260,000 deaths annually in the United States. Most SCDs are caused by ventricular tachycardia ("VT") or ventricular fibrillation ("VF"). Identifying patients at risk of SCD due to VT/VF remains a major challenge. Heart failure has also become a problem of epidemic proportions in the United States. Methods for tracking disease progression or regression may alert treating physicians as to who may benefit from additional therapies or changes in therapy.

SUMMARY OF THE INVENTION

A method for delivering a resonant pacing pattern to a heart of a patient. The heart having a plurality of oscillators producing an oscillation, wherein a variation of the resonant pacing pattern resonates with each of the oscillators, thereby synchronizing the phase of oscillation of each of the oscillators to the resonant pacing pattern.

A cardiac pacing device including a pulse generator producing pacing pulses for delivery to a heart and an electrode placed within the body delivering the pacing pulses with a resonant pacing pattern to the heart.

A method for delivering a non-resonant pacing pattern to a heart of a patient. The heart having a plurality of oscillators producing an oscillation, wherein a variation of the non-resonant pacing pattern does not resonate with each of the oscillators, thereby reducing a magnitude of the oscillation.

A cardiac pacing device including a pulse generator that produces pacing pulses for delivery to a heart and an electrode placed within the body delivering the pacing pulses with a non-resonant pacing pattern to the heart.

A method of delivering a pacing pattern to a heart, measuring a response of the heart to the pacing pattern, the measured response including a series of electrograms representing a plurality of heartbeats of the pacing pattern and calculating diagnostic data from the measured response, wherein the diagnostic data includes data in one of a time domain and a frequency domain.

A method of characterizing a patient by measuring responses of a heart, storing the characterization responses of the heart, monitoring the patient when a pacing pattern is delivered to the heart and controlling one of a magnitude response and a phase response of the heart.

A method of collecting responses of the a heart, the responses corresponding to sequential overlapping groups of beats of the heart, determining a phase of each of the responses, and removing one of the beats when the phase of one of the responses is inverted from the phase of a preceding response.

BRIEF DESCRIPTION OF THE DRAWINGS

FIG. 3a shows a second exemplary resonant cardiac pacing pattern according to the present invention;

FIG. 3b shows a third exemplary resonant cardiac pacing pattern according to the present invention;

FIG. 4a shows a first exemplary non-resonant cardiac pacing pattern according to the present invention;

FIG. 4b shows a second exemplary non-resonant cardiac pacing pattern according to the present invention;

FIG. 4c shows a third exemplary non-resonant cardiac pacing pattern according to the present invention;

FIG. 25 shows an exemplary input form which may be used to program the pacing device according to the present invention;

FIG. 29b shows the magnitude of the frequency composition of electrograms over time including the high frequency noise and the averaged electrogram data according to the present invention;

DETAILED DESCRIPTION

Figure 1:
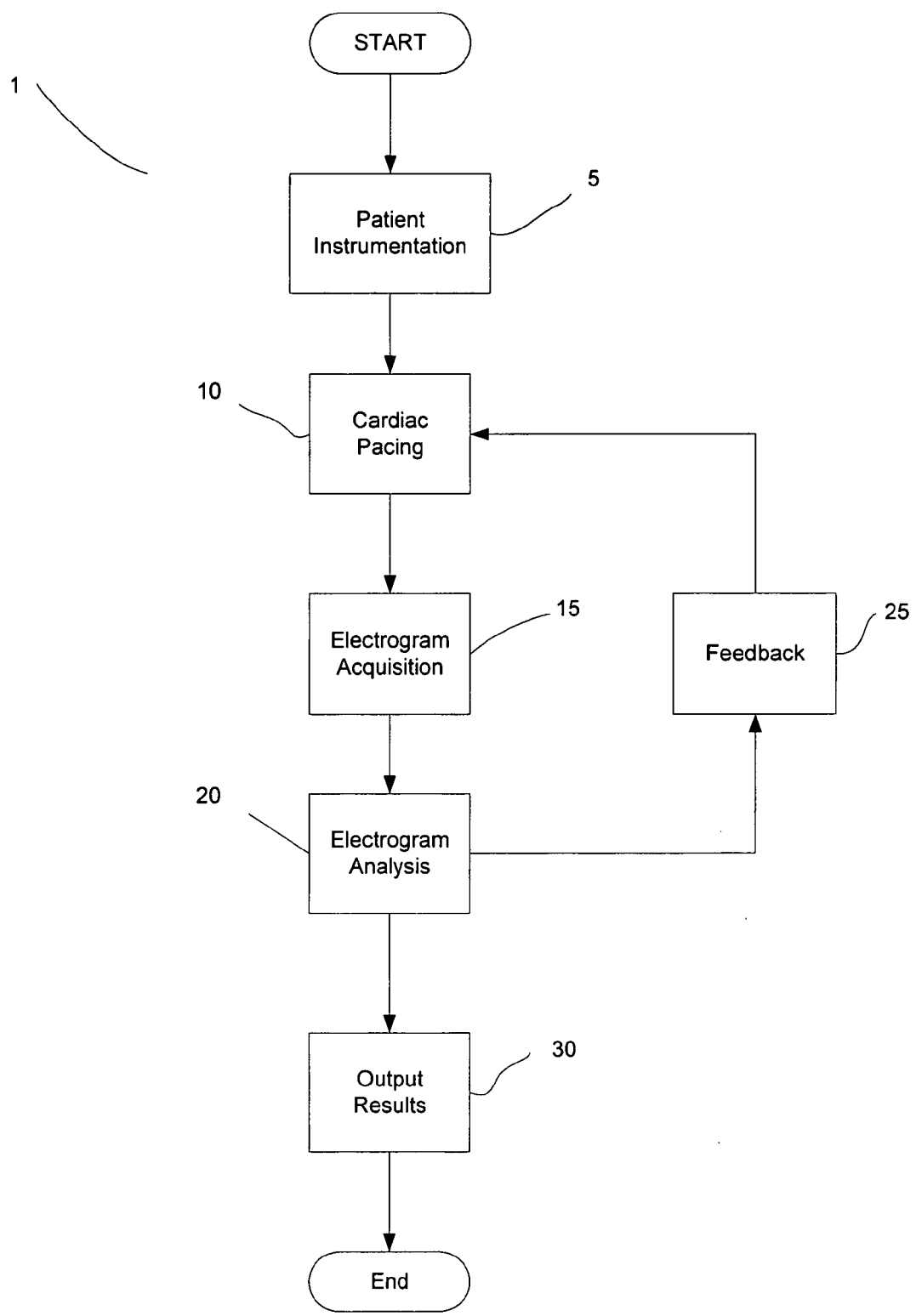
FIG. 1 shows an exemplary general diagnostic and/or therapeutic method according to the present invention.

The present invention may be further understood with reference to the following description and the appended drawings, wherein like elements are provided with the same reference numerals. The present invention includes a diagnostic method that detects and quantifies the potential of a system to have unwanted dynamics. The present invention further includes therapeutic methods of heart pacing to minimize the effects of unwanted dynamics. Repolarization alternans is the major unwanted dynamic and it is a manifestation of decreased cardiac electrophysiologic stability. A decrease in cardiac electrophysiologic stability identifies an increased risk of ventricular tachyarrhythmias and/or identifies progression of cardiomyopathy in people with heart failure. Ongoing repolarization alternans is also a proarrhythmic condition that facilitates the initiation of ventricular tachyarrhythmias.

FIG. 1 shows an exemplary general diagnostic and/or therapeutic method 1 which provides a general overview of the steps used in the exemplary embodiment of the present invention. Each of the individual exemplary steps will be described in greater detail below. In step 5, the patient is fitted with the instrumentation to perform the diagnostic and/or therapeutic methods. In general, the instrumentation includes a cardiac pacing device to provide electrical stimulations to the heart, a heart monitoring device to monitor the heart's response to the electrical stimulation provided by the cardiac pacing device and a signal processing device to analyze the signals provided by the heart monitoring device. The results of the signal analysis may then be used to change the programming features of the cardiac pacing device or provide an output to a physician. Those of skill in the art will understand that there are various devices that may perform the pacing, monitoring and signal processing functions. For example, the cardiac pacing may be performed using a transvenous pacing catheter, an implanted permanent pacemaker ("PM"), an implantable cardioverter defibrillator ("ICD"), etc. The monitoring function may be performed using a surface electrocardiogram, an intracardiac electrogram, a pressure transducer, an echocardiogram, etc. The signal processing function may be performed by software operating on a computing device or by analog and/or digital hardware devices which may or may not include firmware.

In step 10, a specific pacing pattern is provided via the cardiac pacing device, the pacing pattern being serial impulses with temporal or amplitude variation designed to provoke a specific response from the heart. Examples of specific pacing patterns will be described in greater detail below. In step 15, the heart monitoring device acquires and records the heart's response to the specific pacing pattern provided in step 10. In step 20, the signal processing device will analyze the signals provided by the heart monitoring device to detect the repolarization signal of the heart and quantify the repolarization dynamics. As a result of this detection, there may be a feedback signal in step 25 to change the pacing provided to the heart. For example, the feedback signal may alter the rate, the pattern or the amplitude of the pacing pattern being delivered via the cardiac pacing device. When favorable cardiac dynamics are detected through the analysis of signals, this may be used in a decision process to perpetuate the current pacing pattern, i.e., the pacing pattern may be delivered to the patient on a permanent or semi-permanent basis to provide therapeutic benefits to the patient. If unfavorable cardiac dynamics are detected through analysis of the signals, this may be used in a decision process to change the mean cycle length ("CL") of pacing, the magnitude of the CL change in the pacing pattern, or change the pattern of pacing. Meanwhile, the signal processing device, based on the detection of the repolarization will quantify the cardiac electrophysiologic stability of the heart and provide the results in step 30 to a physician who can interpret the results and assess the degree of risk to the patient and the degree of cardiomyopathy.

The basis of the diagnostic portion of the method 1 is the measurement of T-wave alternans ("TWA") that has been identified as an important predictor of risk of ventricular tachycardia/ventricular fibrillation ("VT/VF") in patients referred for electrophysiologic study ("EPS"). In a prospective study of 850 patients after myocardial infarction, TWA and left ventricular ejection fraction were the only independent predictors of VT/VF when compared to nine other risk predictors. Ikeda T., Saito H., Tanno K., et al., "T-wave alternans as a predictor for sudden cardiac death after myocardial infarction," *Am J Cardiol.*, 2002;89:79–82. Similarly, in another prospective study of 313 patients undergoing electrophysiologic study, TWA performed as well as programmed ventricular stimulation for the prediction of ventricular arrhythmias. Gold M R, Bloomfield D M, Anderson K P, et al., "A comparison of T-wave alternans, signal averaged electrocardiography, and programmed ventricular stimulation for arrhythmia risk stratification." *Journal of the American College of Cardiology.* 2000; 36: 2247–2253. In another prospective study of 542 patients with a left ventricular ejection fraction less than 40%, TWA was a strong predictor of mortality independent of ejection fraction and etiology of systolic dysfunction. Bloomfield D M, "T-Wave Alternans in Congestive Heart Failure", American College of Cardiology Late Breaking Clinical Trials, Chicago 2003. TWA also correlates to reductions in left ventricular ejection fraction after myocardial infarction. Schwab J O, Webber S, Schmitt H et, al, "Incidence of T-wave Alternation After Acute Myocardial Infarction and Correlation with Other Prognostic Parameters: Results of a Prospective Study," Journal of Pacing and Clinical Electrophysiology 2001; 24: 957–961. Therefore, TWA may be useful in assessing the degree of cardiomyopathy in heart failure and changes in TWA may be used to identify progression or regression of heart failure.

Each myocyte of the heart has an excitable cell membrane that exists at rest in a polarized state with a negative intracellular electrical potential. Excitation of the membrane occurs when there is depolarization of the membrane, i.e., the intracellular electrical potential becomes more positive. The process of membrane excitation is dependent on transmission of a depolarizing current from a neighboring cell through the gap junctions that electrically connect myocytes together into a syncytium and of sarcolemmal ion channels that carry depolarizing ion currents. Alternatively, excitation may occur when an applied stimulus results in depolarization of the myocyte, i.e., cardiac pacing. Following excitation, additional ion channels carry ion currents to maintain depolarization and then other ion channels to result in repolarization. Additionally, intracellular ion currents interact with sarcolemmal ion currents to influence action potential duration and action potential morphology. Hence, the heart may be viewed as an excitable media where excitable refers to the ability of the myocytes to change between polarized and depolarized states and media refers to the heart consisting of a syncytium of electrically coupled myocytes.

Disease processes that decrease cardiac electrophysiologic stability, as discussed below, may alter the cellular electrophysiology such that the myocyte action potential duration and action potential morphology changes in an oscillatory manner, e.g., changes on alternating beats is called repolarization alternans. Hence, each myocyte has the potential of being an oscillator. Some evidence supports that oscillations of the intracellular calcium currents importantly interact with the sarcolemmal ion currents to produce oscillations of the action potential duration and action potential morphology. Myocytes have electrical interdependence on neighboring myocytes through the gap junctions that locally cause oscillations to occur concordantly, i.e., in the same phase of oscillation. The greater the distance between myocytes, the less there is the electrical interdependence between the myocytes. This allows myocytes in different regions of the heart to oscillate discordantly, i.e., oscillations may occur out of phase in distant regions of the heart. Hence, the heart may be viewed as having a plurality of oscillators linked in an excitable media whereby the oscillators behave locally in an interdependent manner and distantly in an independent manner.

Figure 26A:
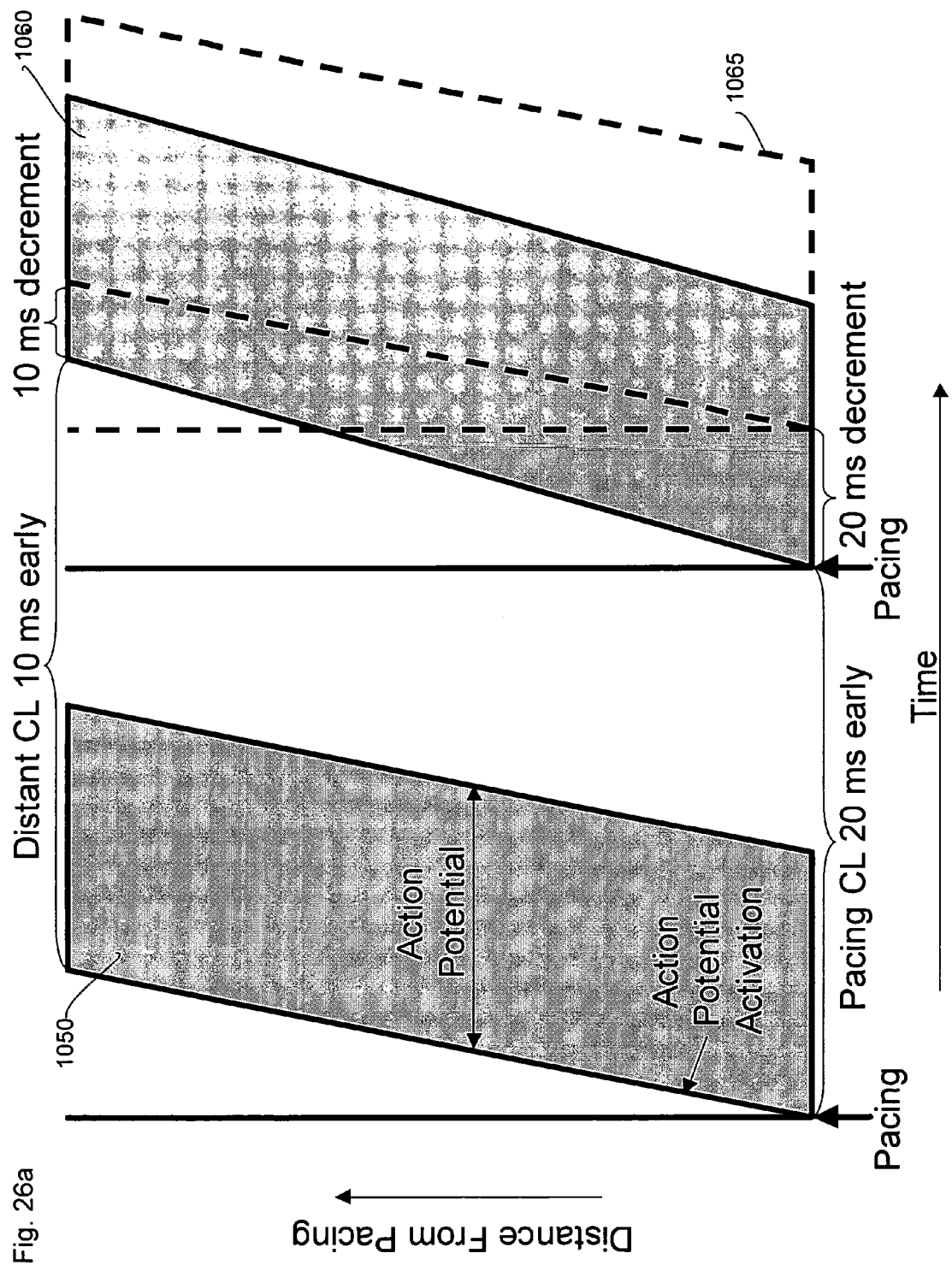
FIG. 26a illustrates a first example of the impact of conduction velocity slowing in response to an early beat according to the present invention.
Figure 26B:
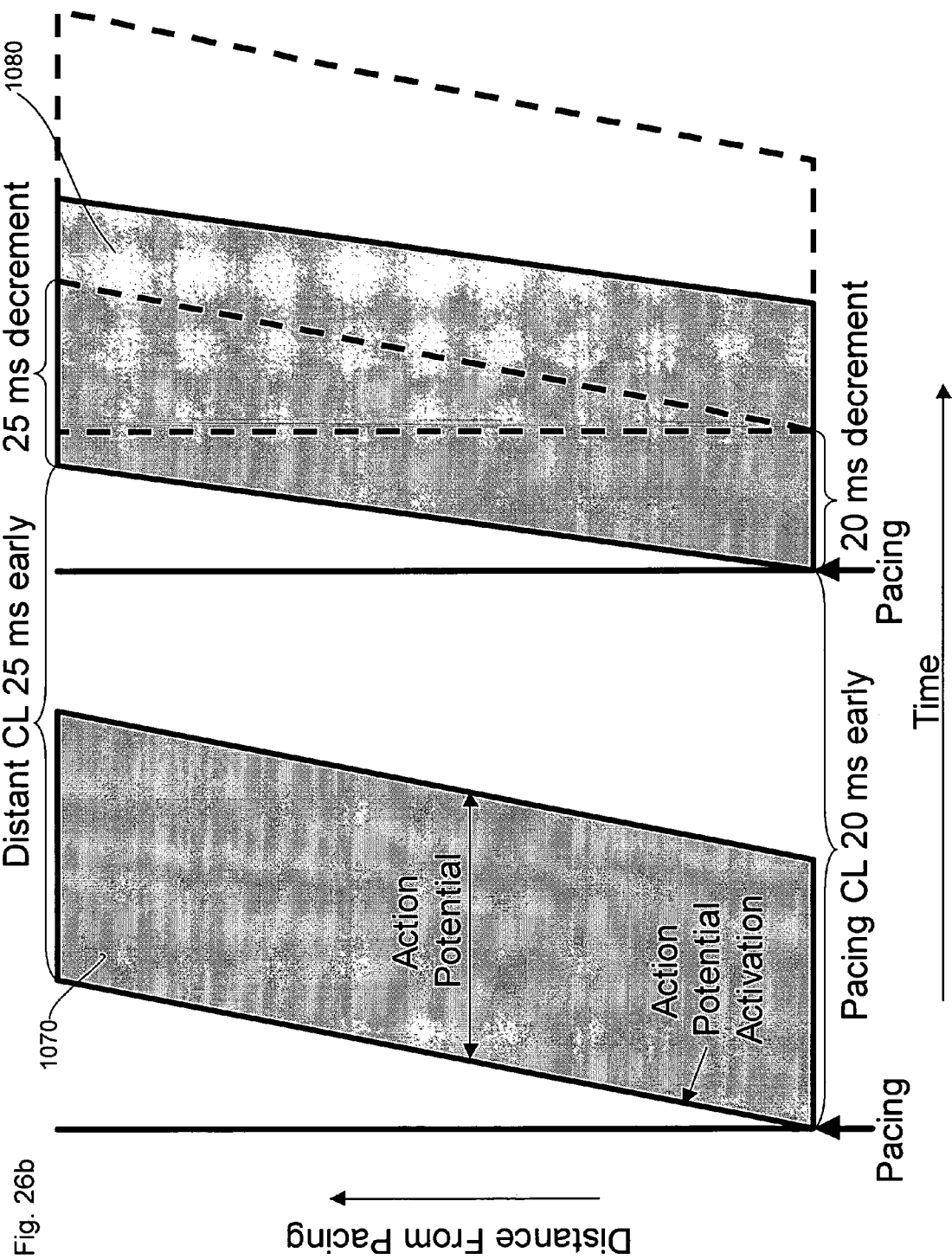
FIG. 26b illustrates a second example of the impact of conduction velocity slowing in response to an early beat according to the present invention.

Timing of depolarization may influence action potential duration and thereby impact and control the phase of oscillation, as discussed in greater detail below. Timing of depolarization for each myocyte relative to cardiac pacing depends on the conduction velocity of the excitable media and the distance of the myocyte from the site that cardiac pacing is delivered. Conduction velocity may have variation on a beat-to-beat basis. If the variation in timing of cardiac pacing is greater than the variation in conduction velocity multiplied by the distance from cardiac pacing site, then the variation in timing of cardiac pacing has the capacity through electrical restitution to influence the oscillators in the excitable media in a concordant manner, i.e., all of the oscillators receive an input with the same phase. This principle is further illustrated in FIG. 26a which illustrates the impact of conduction velocity slowing in response to an early beat. In this example, there are two beats shown 1050 and 1060 with the first beat 1050 being of standard CL and the second beat 1060 being 20 ms early relative to the standard CL (beat 1065 shown with dotted line). Although there is conduction velocity slowing with the premature beat 1060 resulting in a 10 ms delay in a distant region of the heart, the timing of activation is still 10 ms early relative to the prior activation. Hence, all regions of the myocardium are influenced in a concordant manner. In a second example having a first beat 1070 being of standard CL and a second beat 1080 being a 20 ms early beat, FIG. 26b shows a conduction velocity acceleration resulting in a 5 ms acceleration in a distant region of the heart resulting in the timing of activation 25 ms early relative to the prior activation in that distant region. Again, all regions of myocardium are influenced in a concordant manner. Depending on the variation of CL and conduction velocity, variation of CL may impact all of the oscillators in a concordant manner despite spatial separation within the heart. Hence, cardiac pacing may be used to modulate the plurality of oscillators linked in an excitable media. Understanding this paradigm is fundamental the methods of this invention.

The T-wave is the electrocardiogram ("ECG") manifestation of ventricular repolarization. TWA is the ECG manifestation of beat-to-beat oscillations of action potential duration and action potential morphology. In animal models, TWA has been shown to be responsible for the functional block leading to the initiation of VF and to the initiation of VT around scar tissue. TWA has been reported prior to VT/VF on ICD recording in patient case reports and in a canine model of VT/VF. Therefore, it is believed that TWA may be a strong predictor of the risk of VT/VF due to possible mechanistic involvement in the genesis of VT/VF. Further, the capacity to have pathologic TWA is an electrophysiologic correlate to the degree of cardiomyopathy and may be used to identify and quantify changes in the degree of cardiomyopathy in patients with heart failure.

The human heart under normal conditions is a stable system. The system undergoes electrical depolarization to initiate mechanical contraction (systole) and electrical repolarization to allow mechanical relaxation (diastole) of the ventricle with each heartbeat. A person that has an average heart rate of 60 beats per minute has undergone two billion cycles of depolarization and repolarization by the time they are 65 years old. The heart as a system must remain stable in the face of a multitude of changes such as growth, aging, accelerations and deceleration of heart rate, sympathetic and parasympathetic stresses, changes in electrolytes, and exposure to medications. Common disease processes such as myocardial infarction, hypertension, and heart failure may reduce the stability of the system to these same stresses. Identification of decreased system stability is an approach to identify systems that may become unstable. In terms of the heart, system failure due to an unstable system may result in VT/VF. It is therefore very desirable to identify reductions in system stability prior to these changes becoming life threatening.

The stability of a system may be characterized by a continuum from stable, to marginally stable, then unstable. A stable system under steady-state conditions has no oscillations of an output when there is no input. A marginally stable system under steady-state conditions has oscillations of an output when there is no further input. An unstable system under steady state conditions has a growing output without bound. These principles may be applied to the electrophysiologic stability of the heart. Whereas a stable heart is resistant to arrhythmias, a marginally stable heart is susceptible to develop arrhythmias, and an unstable heart will imminently develop an arrhythmia.

The normal response of the myocardial tissue under steady-state conditions while being paced at a constant heart rate is for the action potential duration and action potential morphology to approach a constant. When cardiac pacing is applied to a region of a whole heart, the action potential of the myocardium in each region of the heart approaches a constant duration and morphology. The T-wave of the ECG is the sum of the effects of the repolarization phase of all myocardial action potentials. Hence, the T-wave approaches a constant morphology in a stable heart under steady state conditions and there is an absence of significant beat-to-beat changes in the T-wave, i.e., TWA. A result of a decrease in cardiac electrophysiologic stability is the development of oscillations of repolarization under steady state conditions. The characteristic oscillation of repolarization occurs every other beat. This results in the manifestation on the surface ECG of the phenomenon of TWA. Multiple cellular electrophysiology mechanisms have been described to cause TWA. Multiple disease processes that lead to an increased frequency of VT/VF have been described to have the phenomenon of TWA such as heart failure, myocardial ischemia/infarction, hypertensive heart disease, and the long-QT syndromes. The presence of TWA under steady state conditions identifies marginally stable cardiac electrophysiology. The response of an unstable system is to have continuous increase in oscillations. The cardiac electrophysiologic analogy of an unstable system is to have oscillation increase until a ventricular arrhythmia occurs.

Testing system stability under steady state conditions yields an important but limited view of system stability. An additional manner of characterizing system stability is to assess the impulse and frequency responses of the system. Relative stability may be inferred by the duration of time a system takes to suppress oscillations. Under steady state conditions, a system that is faster at suppression of oscillations is more stable than a system that takes longer to suppress oscillations. A long duration of time to suppress oscillations identifies a marginally stable system. Clinically these responses are important because the heart must remain stable in responses to different heart rates, heart rate variability and premature atrial and ventricular beats.

The heart is the system undergoing stability testing where the input is cardiac pacing and the output is measured by the heart monitoring device, e.g., a surface ECG or an intracardiac electrogram. The impulse response of the heart (the system) may be tested by provided a temporal or amplitude change in cardiac pacing (the input) and measuring the response in the electrogram (the output). The magnitude of the impulse may be modulated by a temporal change of CL, or voltage amplitude change of cardiac pacing. For example, a large impulse may be a premature ventricular contraction ("PVC") with a compensatory pause. A small impulse may be change of CL within the normal range of heart rate variability. A small impulse may also be an increase in voltage of cardiac pacing that results in a larger effective electrode and shortens the mean interbeat time to depolarization of the ventricle. The sign of the impulse may be inverted by creating a late beat rather than a premature beat. A step response may be assessed by an abrupt change in CL to either longer or shorter CL.

The frequency response of a system may be tested with a series of impulses that conform to the curve of the frequency of interest and may be used to determine the characteristic roots that determine the phase and gain of the system. This is analogous to the derivation of a Bode plot for an electrical circuit. Since the frequency of the characteristic oscillatory output of the system is known, delivering an oscillatory input at that same frequency may test resonance within the system. Clinically, R—R alternans is known to produce TWA. This is because the input to the system (R—R interval alternans) resonates with the output of the system (TWA). Frequency response testing may provide a more powerful tool than traditional TWA testing for assessment of system stability whereby an input that resonates with the output may have a large gain (amplify oscillations) and an input that does not resonate with the output may have a small gain (suppress oscillations).

Heart rate variability normally results from sympathetic and parasympathetic modulation of the heart rate. A decrease in heart rate variability has been identified as a predictor of risk of VT/VF and of progression of heart failure. It has been thought that parasympathetic activity may suppress VT/VF and heart failure results in parasympathetic withdrawal. However, the direct cardiac effect of heart rate variability has not been evaluated in the past independent of parasympathetic activity.

Ventricular tachyarrhythmias (VT/VF) are commonly precipitated by dynamic stresses such as atrial tachyarrhythmias and ventricular ectopy. Cardiac repolarization is adaptive and normally remains stable in the face of these perturbations by rapidly dampening oscillations (normal electrophysiologic stability). Cardiomyopathy causes abnormal cellular electrophysiology that decreases the ability of hearts to dampen oscillations (marginal electrophysiologic stability). Hearts susceptible to VT/VF may be provoked to oscillate in response to a premature beat. The exemplary embodiment of the present invention includes a method of testing for the phenomenon of repolarization alternans that is designed to perform as a discriminator of cardiac electrophysiologic stability. The exemplary method is called the "dynamic T-wave alternans test," and is based on the principle of resonance.

If a heart has the potential to have repolarization alternans (marginal electrophysiologic stability), then the phenomenon may be provoked by a pacing with a pattern that resonates with repolarization alternans. In general, the exemplary dynamic T-wave alternans test is a method that: (1) dynamically stresses a system; (2) measures the electrophysiologic response of the system to the stress; and (3) quantifies the oscillatory response of the system to the stress. Cardiac pacing with programmed irregularity of CL (or amplitude) is used to create the dynamic stress. The electrophysiologic response of the system is measured on the surface ECG or on intracardiac electrograms (unipolar or bipolar). Measures derived from signal processing of the electrograms are used to quantify the magnitude of pacing induced oscillations and the ability of the system to dampen repolarization alternans. Electrophysiologic stability is then quantified with these measures. In an alternative embodiment, the frequency response of the system may be used to test the stability. As will be described in greater detail below, the present invention allows for the time domain response and frequency domain response of the heart system to be monitored and controlled. The electrophysiologic stability of the heart may be determined using either parameters derived from the time domain response or the frequency domain response.

Normal hearts rapidly suppress oscillations of repolarization (normal cardiac electrophysiologic stability). This may be measured as a rapid rate of decay of oscillations using the digital signal processing methods incorporated into the exemplary analysis software provided in the signal processing device. Valt is the voltage magnitude of TWA. The rate of decay of oscillations is the first derivative of the oscillation magnitude (dValt/dt). Hearts with the potential to have oscillations of repolarization have a slower decay rate of oscillations (marginal cardiac electrophysiologic stability) than hearts without the potential to have oscillations of repolarization. Hence, the rate of decay of oscillations (dValt/dt) is a discriminator of relative electrophysiologic stability. The exemplary embodiment of the present invention includes pacing with an irregularity of CL in a repetitive pattern. The timing of the irregularity in the cycle length is designed to resonate with repolarization oscillations of past beats to create a greater magnitude of oscillations in hearts with marginal electrophysiologic stability. A second discriminator between marginal and normal electrophysiologic stability is the magnitude of oscillations (Valt). A derived measure of electrophysiologic stability is an index of both the decay rate and the magnitude oscillations named the T-wave stability index ("TWSI"). The TWSI equals the decay rate of alternans (dValt/dt) divided by the magnitude of alternans (Valt). By incorporating both discriminators, the decay rate is normalized to the magnitude of oscillations and the index maximizes the differentiation of relative T-wave stability.

Referring back to FIG. 1, the following will describe the cardiac pacing of step 10 in more detail. The dynamic pacing protocol is the method of cardiac pacing that is used to provoke oscillations and observe oscillation decay. The controlled provocation of oscillations may be accomplished with multiple pacing patterns. Those of skill in the art will understand that variations of the basic pattern may be used to accomplish the same task. The present invention is intended to include all pacing patterns that are designed to pace with a temporal or amplitude variation that provokes oscillations and resonates with past oscillations when the pattern is repeated. This present invention also includes incorporation into the pacing pattern a period of decreased induction of oscillations.

The following are exemplary pacing patterns that may be modified to accomplish the induction of oscillations. Each capitol letter represents a pacing CL or amplitude. The underlined letters represent the repeating pattern. The following patterns may be used for provocation of oscillations:

...AB<u>AB</u>AB...

...ABC<u>ABC</u>ABC...

...ABCD<u>ABCD</u>ABCD...

...ABCDE<u>ABCDE</u>ABCDE...

...ABCDEF<u>ABCDEF</u>ABCDEF...

...ABCDEFG<u>ABCDEFG</u>ABCDEFG...

...ABCDEFGH<u>ABCDEFGH</u>ABCDEFGH...

Although all of the above patterns may be used to provoke oscillations, some patterns may be more efficient for the measurement of relative T-wave stability. The first pattern (AB) provides an input that induces oscillations without a period for observation of decay of oscillations. This is a first example of a resonant pacing pattern. The patterns (ABC), (ABCDE) and (ABCDEFG) pace with a pattern that allows for induction of oscillations and observation of oscillation decay. However, the repeating pattern does not resonate with past patterns due to a 180° phase shift when the pattern is repeated. The result is that these pacing patterns induce short timescale repolarization oscillations that may be subsequently suppressed by repetition of the pattern. The present invention is intended to include all pacing patterns that are designed to pace with temporal or amplitude variation that provoke oscillations and provoke oscillations that are 180° out of phase with past oscillations when the pattern is repeated, i.e., a non-resonant pacing pattern. The diagnostic and therapeutic uses of these non-resonant pacing patterns will be further discussed below. The patterns (ABCD), (ABCDEF) and (ABCDEFGH) provoke oscillations, provide a time period of oscillation decay observation, and provoke oscillations that resonate with prior oscillations when the pattern is repeated. These are additional examples of resonant pacing patterns. A resonant pacing pattern may also de defined in the frequency domain as any temporal pattern of pacing that results in a high magnitude of frequency content at the alternans frequency.

Figure 2:
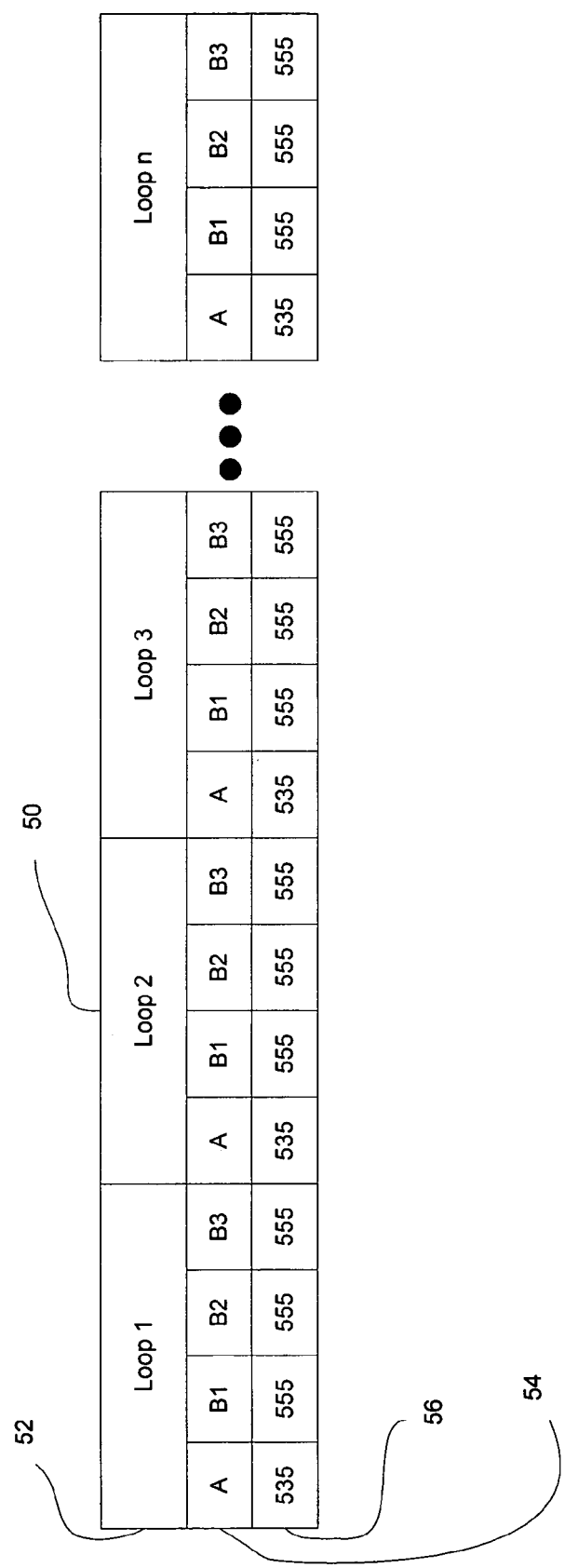
FIG. 2 shows an exemplary resonant cardiac pacing pattern according to the present invention.

FIG. 2 shows an exemplary resonant cardiac pacing pattern 50. Resonant pacing has a high magnitude of the frequency content of the variation of pacing (e.g., cycle length or magnitude) in the region of the oscillator of the heart. As will be described in greater detail below, the exemplary embodiment of the present invention considers an example of the region of oscillations being in the 0.5 cycles/beat region. Thus, a resonant pacing pattern for this example may be any pattern having a high frequency content within the 0.5 cycles/beat region. The temporal pattern of pacing pattern 50 comprises the placing of a slightly premature cycle length at an even numbered interval within a constant baseline cycle length at a moderately elevated heart rate. Frequency domain analysis of the temporal variation of this pattern results in high frequency content at 0.25 and 0.5 cycles/beat regions. In the example of pacing pattern 50, the premature beat will be 20 ms early, which is equivalent to the usual physiologic range of normal heart rate variability. The specific pattern is a modification of the (ABCD) pattern described above, where cycle lengths (C) and (D) are equivalent to (B), and thus, the pattern is described as (A, B1, B2, B3). The row 54 of the pacing pattern 50 shows the repeating pattern of B2, B3 for each of the loops shown in the row 52. Each of loops 1 . . . n have the same repeating pattern of A, B1, B2, B3. The exemplary pacing pattern 50 has a cycle length (A) of 535 ms (milliseconds) and a cycle length (B) of 555 ms as shown in the row 56. The exemplary resulting overall heart rate is 109 bpm. Those of skill in the art will understand that the diagnostic test may check the heart over a range of heart rates (e.g., 80 bpm, 90 bpm, 100 bpm, etc.) to determine the cardiac electrophysiologic stability.

FIG. 2 shows three complete continuous loops of pacing pattern 50 and also illustrates that the pacing pattern 50 may extend over any number of loops n based on the particular test and/or patient being tested. The exemplary repeating pacing pattern 50 illustrated in FIG. 2 incorporates the three aspects of provoking oscillations, providing a time period of oscillation decay observation, and provoking oscillations that are in phase (resonate) with past oscillations when the pattern is repeated. Cardiac pacing may be performed in any number of configurations. The preferred pacing configuration for identification of risk of VT/VF is either atrial pacing if there is adequate AV-nodal function or atrial-ventricular sequential pacing with a short AV-delay. The preferred pacing configuration for monitoring risk of VT/VF and cardiomyopathy is either atrial pacing if there is adequate AV-nodal function or atrial-ventricular sequential pacing with a short AV-delay. If a bi-ventricular pacing system has been implanted, then the preferred pacing configuration for monitoring risk of VT/VF and cardiomyopathy is either atrial-right ventricular sequential pacing with a short AV-delay or atrial-bi ventricular sequential pacing with a short AV-delay.

Figure 3C:
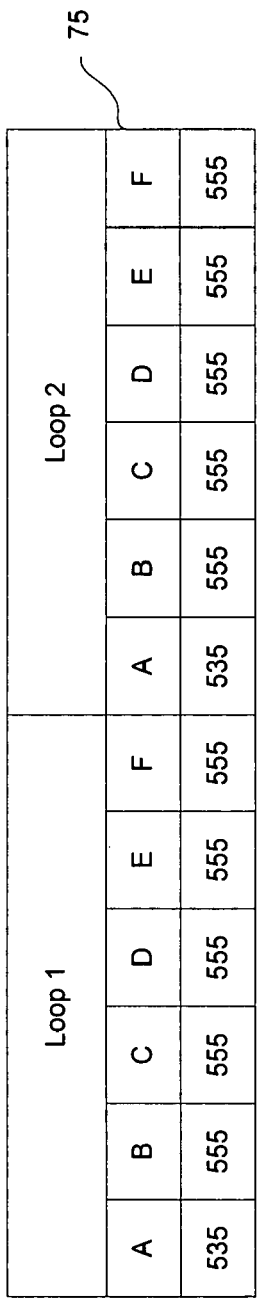
FIG. 3c shows a fourth exemplary resonant cardiac pacing pattern according to the present invention.
Figure 3D:
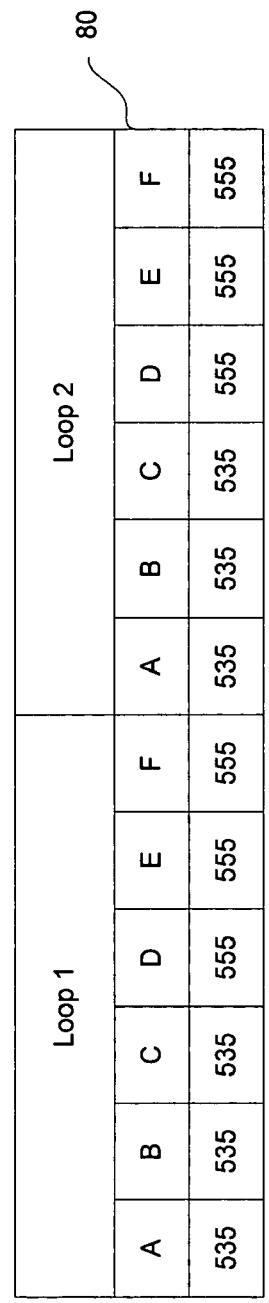
FIG. 3d shows a fifth exemplary resonant cardiac pacing pattern according to the present invention.

FIGS. 3*a*–*d* show additional exemplary resonant cardiac pacing patterns. Two complete loops are shown for each exemplary pacing pattern and the numbers represent the cycle length of each beat in milliseconds. FIG. 3*a* shows the pacing pattern 60 that is a resonant cardiac pacing pattern having two alternating cycle lengths. FIG. 3*b* shows the pacing pattern 70 that is a 4-beat pacing pattern that includes a compensatory pause. Thus, for the pacing pattern 70, beat A of 535 ms is the premature beat, beat B of 575 ms is the post-premature beat having the compensatory pause and beats C and D of 555 ms are baseline CL beats. FIG. 3*c* shows the pacing pattern 75 that is a 6-beat pacing pattern having no compensatory pause. FIG. 3*d* shows the pacing pattern 80 that is a hybrid 6-beat pacing pattern. For pacing pattern 80, beat A of 535 ms is a premature beat relative to beat F of 555 ms that results in a shortening of action potential duration. Beat D of 555 ms is longer relative to beat C of 535 ms that results in a lengthening of action potential duration. Hence, the temporal changes in CL result in provocation of oscillations of repolarization that resonate with past oscillations.

FIGS. 4*a*–*g* show additional exemplary non-resonant cardiac pacing patterns. Two complete loops are shown for each exemplary pacing pattern. Non-resonant pacing has a low magnitude of the frequency content of the variation of pacing (e.g., cycle length or magnitude) in the frequency region of the oscillator of the heart. As will be described in greater detail below, the exemplary embodiment of the present invention considers an example of the region of oscillation being in the 0.5 cycles/beat region. Thus, a non-resonant pacing pattern for this example may be any pattern having a low frequency content within the 0.5 cycles/beat region. However, there may be other examples of oscillation regions at differing frequencies. Thus, the non-resonant patterns for these other frequency regions will be patterns which have a low frequency content in the region of interest for the particular oscillation. The frequency domain definition of non-resonant pacing described above may be restated as a time domain definition due to the principle of duality between the time and frequency domains. An example of a non-resonant pacing pattern in the time domain is a pacing pattern of temporal variation of cycle length or pacing amplitude that induces a low amplitude oscillation and then repeats the pacing pattern such that the next induction of oscillation is 180 degrees out of phase with the prior induction of oscillation.

Figure 4D:
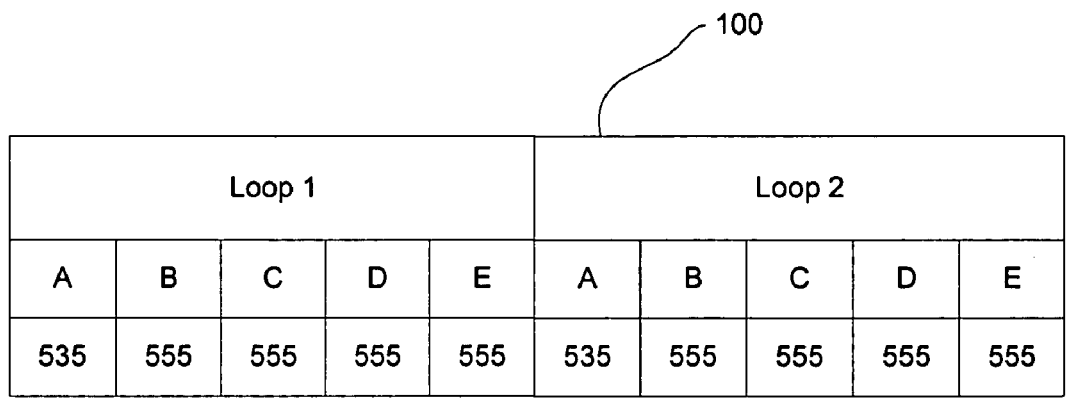
FIG. 4d shows a fourth exemplary non-resonant cardiac pacing pattern according to the present invention.
Figure 4E:
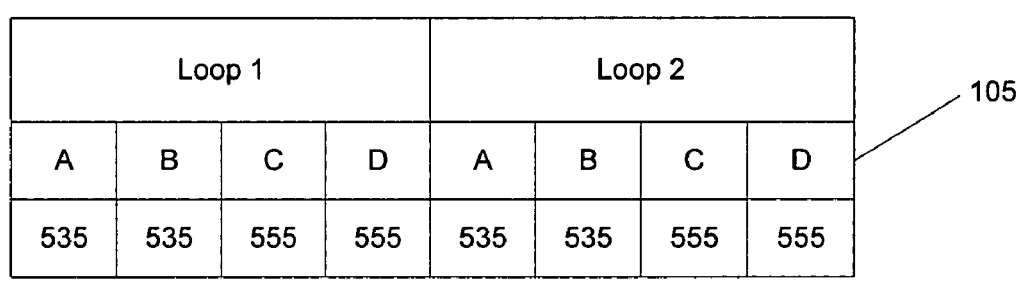
FIG. 4e shows a fifth exemplary non-resonant cardiac pacing pattern according to the present invention.
Figure 4F:
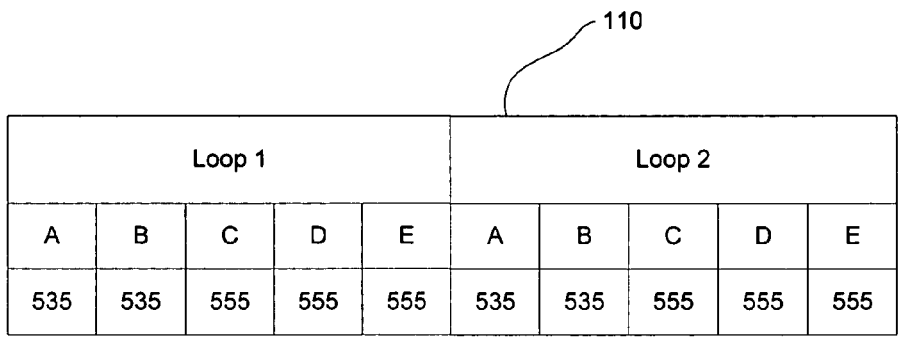
FIG. 4f shows a sixth exemplary non-resonant cardiac pacing pattern according to the present invention.
Figure 4G:
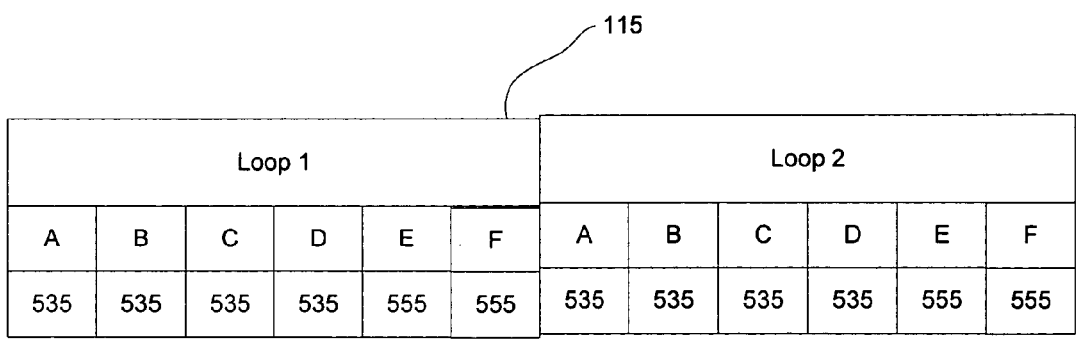
FIG. 4g shows a seventh exemplary non-resonant cardiac pacing pattern according to the present invention.

FIG. 4*a* shows the pacing pattern 85 that is a 3-beat pacing pattern having no compensatory pause. FIG. 4*b* shows the pacing pattern 90 that is a 3-beat pacing pattern having a compensatory pause. FIG. 4*c* shows the pacing pattern 95 that is a 3-beat pacing pattern having no compensatory pause. FIG. 4*d* shows the pacing pattern 100 that is a 5-beat pacing pattern. FIG. 4e shows the pacing pattern 105 that is a 4-beat pacing pattern FIG. 4f shows the pacing pattern 110 that is a hybrid 5-beat pacing pattern. FIG. 4g shows the pacing pattern 115 that is a hybrid 6-beat pacing pattern.

Those of skill in the art will understand that the preceding resonant and non-resonant pacing patterns are provided as examples of pacing patterns that may be used for the purposes of the diagnostic method according to the present invention. However, the present invention may include any number of resonant and non-resonant pacing patterns that meet the criteria described above for the diagnostic method. Additional therapeutic uses for resonant and non-resonant patterns will be described in detail below.

Again referring back to FIG. 1, the electrogram acquisition of step 15 is used to detect the signals associated with repolarization. Those of skill in the art will understand that multiple methods of detection are available. For example, ventricular repolarization may be detected on the surface ECG or using intracardiac electrodes (bipolar or unipolar lead configuration). The preferred configuration for identification of risk of VT/VF is recording of the surface ECG. The preferred intracardiac electrogram recording configuration for monitoring risk of VT/VF and cardiomyopathy is an electrogram that is a unipolar far-field from the ventricular cardiac pacing. Examples of this are an atrial to pacemaker generator electrogram in patients with a dual chamber pacemaker who are AV sequentially paced with a short AV-delay, a defibrillator coil to ICD generator electrogram in patients who are implanted with an ICD. Other unipolar far-field electrograms such as right ventricular to right atrial electrogram or right ventricular to pacemaker generator are preferred to right ventricular bipolar electrograms.

Figure 5A:
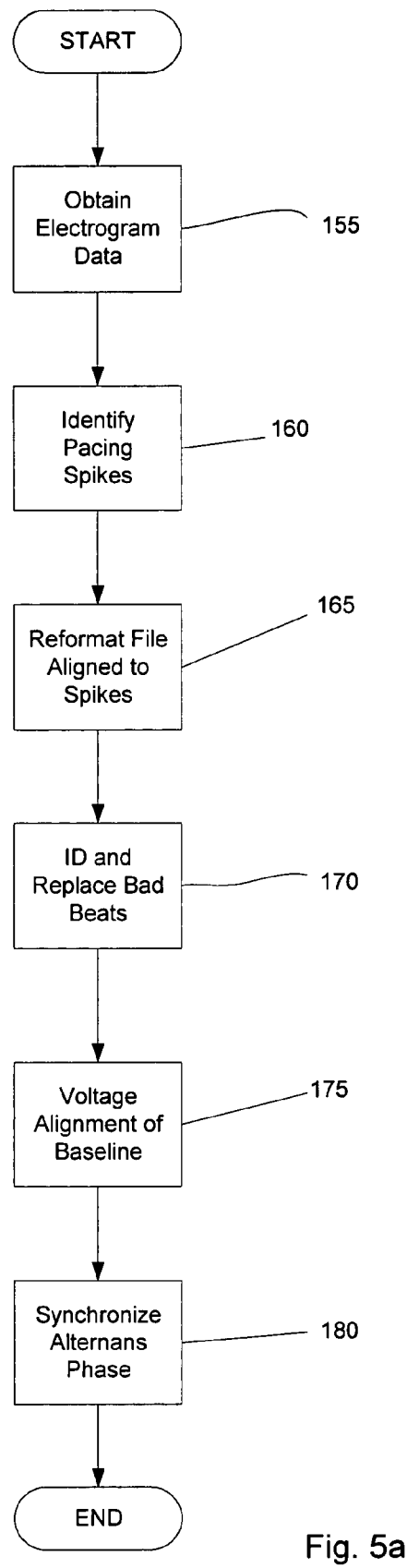
FIG. 5a shows an exemplary process for detecting repolarization according to the present invention.

FIG. 5a shows an exemplary process 150 for detection of repolarization. Those of skill in the art will understand that the exemplary process 150 may include the steps of electrogram acquisition (step 15) and electrogram analysis (step 20), or portions thereof, of FIG. 1. In step 155, the electrogram data is obtained by, for example, sampling the ECG at 1 kHz, with 1–2 μV resolution, and band-pass filtering from 0.05–300 Hz. Multiple electrograms may be simultaneously acquired. Those of skill in the art will understand that these are only exemplary values and that the acquisition and filtering may be different for different methods of acquisition, e.g., pacemaker or ICD acquisition, intracardiac acquisition, etc. The digitized electrograms may then be electronically stored and imported into the analysis software package of the signal processing device or analyzed with software within the pacemaker or ICD.

Figure 6A:
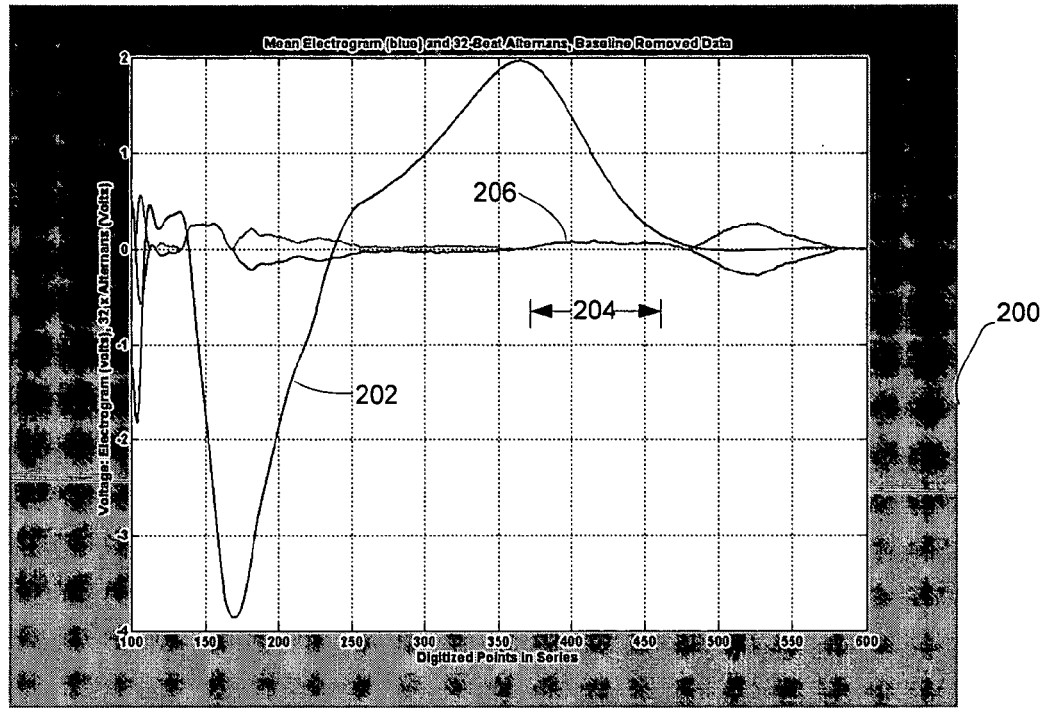
FIG. 6a shows a first exemplary signal averaged electrogram and alternans detection curve for a first patient having a constant ventricular pacing pattern according to the present invention.
Figure 6B:
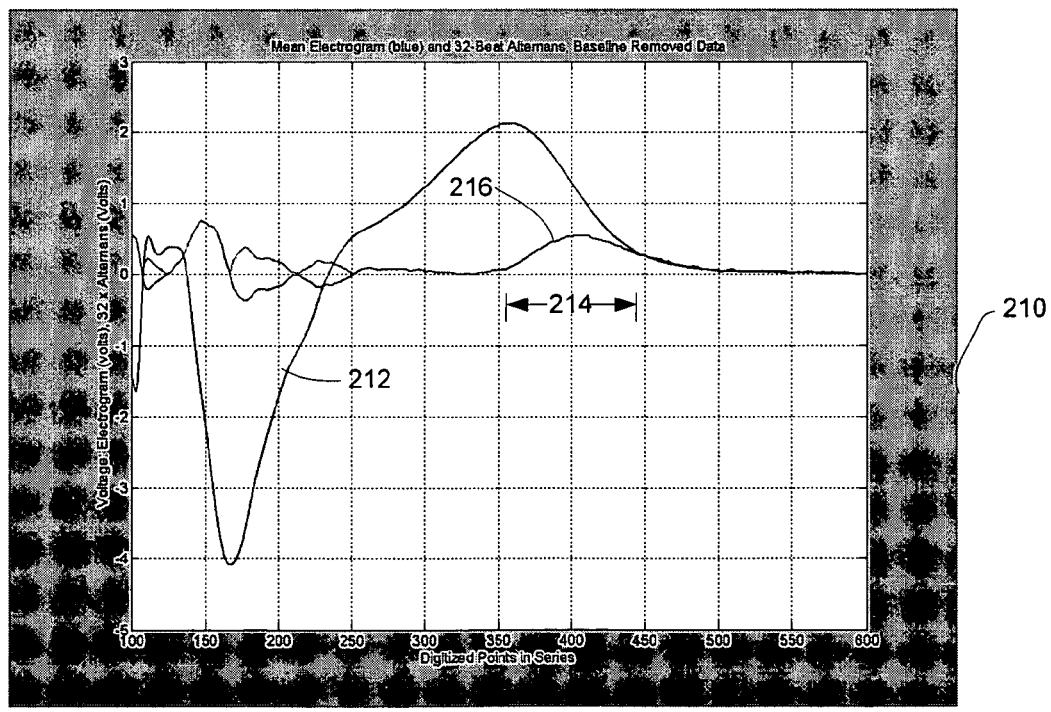
FIG. 6b shows a second exemplary signal averaged electrogram and alternans detection curve for a first patient having a resonant ventricular pacing pattern according to the present invention.

FIGS. 6a–e show various exemplary electrograms for patients as a result of various applied pacing patterns. Those of skill in the art will understand that the exemplary electrograms shown in FIGS. 6a–e. show a signal averaged ECG aligned to the pacing spike for each of the described scenarios. FIGS. 6a–b show a electrograms for a patient who underwent ablation of an accessory pathway and is otherwise free of cardiac disease. FIG. 6a shows electrogram 200 recorded from the V2 position of a standard 12-lead ECG for the first patient that is the result of simultaneous right atrial and right ventricular apical pacing at a constant CL of 550 ms. The curve 202 shows the average electrogram of the heart in ECG lead V2 that is the result of averaging all the digitized ECG signals aligned to the pacing spike deflection. The Valtmean curve 206 is the result of a method used to identify the greatest region of TWA. A method that will identify the Valtmean curve and the greatest regions of repolarization alternans will be described below. In addition, other methods which use the entire electrogram data will also be described.

In this exemplary patient who is exhibiting no signs of cardiac disease, curve 206 suggests the absence of TWA since the curve 206 only varies slightly from zero voltage and the minor variation may be within the range of background noise. Precise determination of the presence or absence of TWA relies on the full method described below. Thus, the electrogram 200 suggests normal electrophysiologic stability with steady state pacing.

FIG. 6b shows the electrogram 210 for the same patient when the 4-beat resonant pacing pattern 50 described above with reference to FIG. 2 is applied. Again, the curve 212 shows the average electrogram of the heart as a result of cardiac pacing aligned to the pacing spike deflection. The region 214 of the Valtmean curve 216 shows 100 ms segment of the ECG with the greatest repolarization alternans for the patient's heart. Oscillations of repolarization will be further characterized from region 214. As can be seen from this electrogram 210, the resonant pacing pattern induces an oscillation causing a measurable TWA. As was described above and as will be described in greater detail below, the health of the heart may be determined by observing the magnitude and decay of these induced oscillations. Thus, the TWA shown in electrogram 210 is an expected phenomenon because it was induced by the pacing pattern. The relative electrophysiologic stability of the patient's heart will be determined by the heart's ability to dampen the induced oscillations.

Figure 6C:
FIG. 6c shows a first exemplary signal averaged electrogram and alternans detection curve for a second patient having a constant ventricular pacing pattern according to the present invention.
Figure 6D:
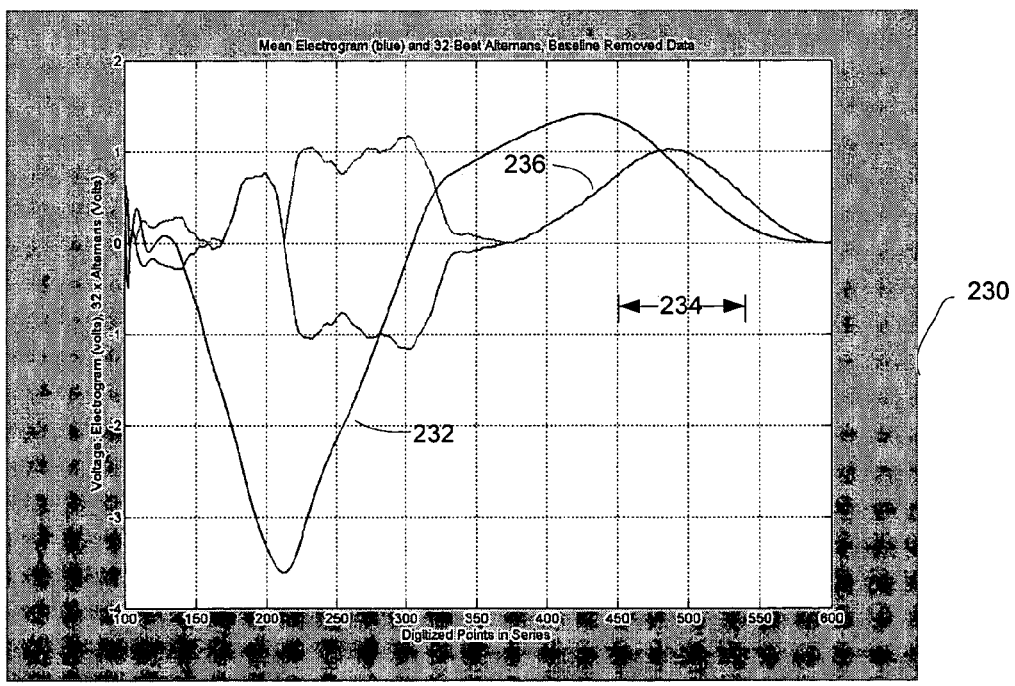
FIG. 6d shows a second exemplary signal averaged electrogram and alternans detection curve for a second patient having a resonant ventricular pacing pattern according to the present invention.
Figure 6E:
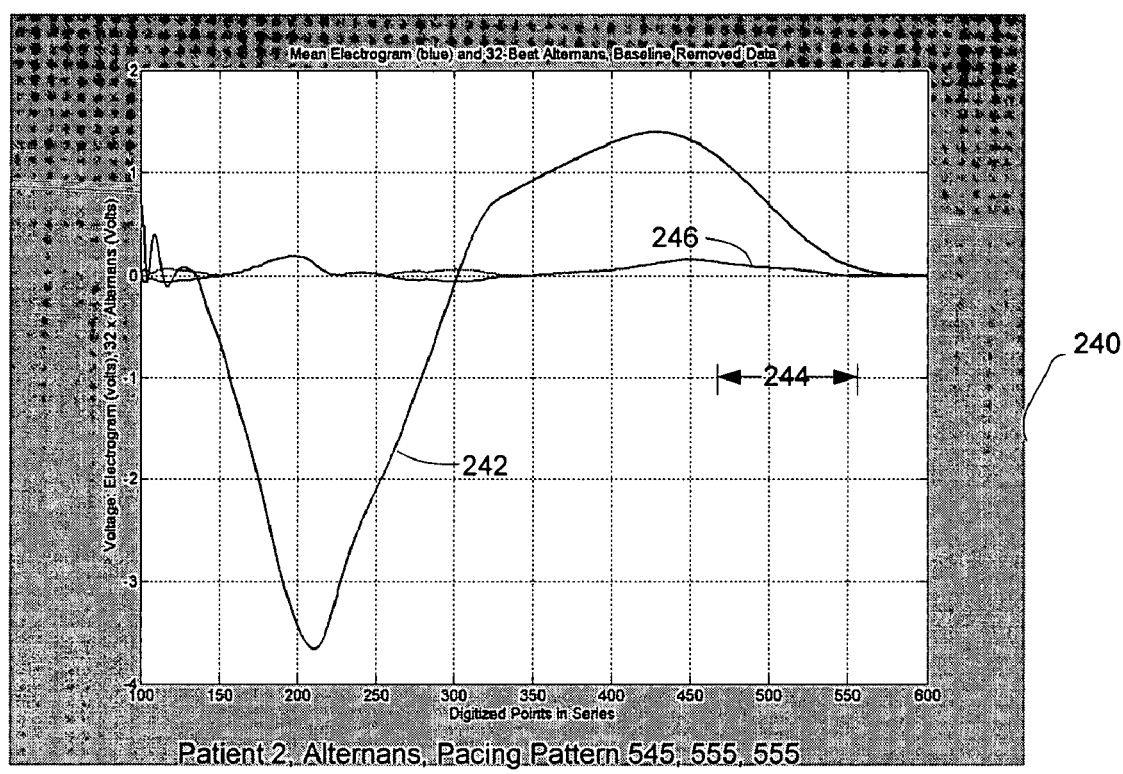
FIG. 6e shows a third exemplary signal averaged electrogram and alternans detection curve for a second patient having a non-resonant ventricular pacing pattern according to the present invention.

FIGS. 6c–e show electrograms for a second patient with coronary artery disease and heart failure due to myocardial infarction. FIG. 6c shows electrogram 220 for the second patient when simultaneous atrial and ventricular cardiac pacing at a constant CL of 550 ms is applied. The curve 222 shows the average electrogram aligned to the pacing spike and the region 224 of the Valtmean curve 226 shows the 100 ms segment with the greatest repolarization alternans. Oscillations of repolarization will be further characterized in this region 224. In this particular patient, the electrogram 220 suggests the presence of TWA as shown by curve 226 when the steady state pacing pattern is applied. Precise determination of the presence or absence of TWA relies on the full method described below. As described above, the presence of TWA when a steady state pacing pattern is applied indicates marginal electrophysiologic stability. The diagnostic method according to the present invention will determine the relative electrophysiologic stability.

FIG. 6d shows the electrogram 230 for the same patient when the 4-beat resonant pacing pattern 50 described above with reference to FIG. 2 is applied. The curve 232 shows the average electrogram aligned to the pacing spike of the heart as a result of simultaneous atrial and ventricular pacing and the region 234 shows the 100 ms segment with greatest repolarization alternans that is identified by Valtmean curve 236. The magnitude of pacing induced repolarization alternans in region 234 suggests that a large oscillation has been induced by the 4-beat resonant pacing pattern. Precise determination of the magnitude and dynamics of TWA relies on the full method described below. Region 234 of patient 2 is much greater than region 216 of patient 1 (FIG. 6b) due to patient 2 having less cardiac electrophysiologic stability.

FIG. 6e shows the electrogram 240 for patient 2 when a 3-beat non-resonant pacing pattern 85 described above with reference to FIG. 4a is applied. The curve 242 shows the average ECG aligned to the pacing spike of the heart as a result of simultaneous atrial and ventricular pacing and the region 244 shows the 100 ms region with the greatest repolarization alternans found under curve 246. The TWA measured in the region 244 and shown by curve 246 indicates that the 3-beat non-resonant pacing pattern has reduced the intrinsic TWA that was present when pacing with a constant CL as described with reference to FIG. 6c. The therapeutic methods and benefits of applying various pacing patterns will be described in greater detail below.

Referring back to FIG. 5a, in step 160, a predefined spike detector array is used to robustly identify pacing spikes (sometimes called a fiduciary). A pacing spike is the small duration high frequency deflection that appears on the surface ECG indicating that a pacemaker output was delivered. It is caused by the brief discharge of electricity produced by the pacemaker to stimulate the heart. An array designed to have a similar frequency composition as the pacing spike and dissimilar frequency composition to the remainder of the electrogram may be used to identify the pacing spike. The array that was used in this example consisted of the series [−1, −2, −1, 2, 4, 2, −1, −2, −1]. This array is mathematically convolved with the electrogram in the region expected to contain the pacing spike and the location of the maximum absolute value of the convolution is considered to be the pacing spike location. Since the pacing pattern is known (e.g., 535, 555, 555, 555), the region that is expected to contain the pacing spike may be determined based on the known pacing pattern.

The fiduciary for electrogram alignment depends on the circumstances under which the electrogram is acquired. The preferred fiduciary for determining the risk of VT/VF during an electrophysiologic study is the pacing spike as described above. The preferred fiduciary for monitoring the risk of VT/VF and degree of cardiomyopathy is the pacing spike on the bipolar electrogram where pacing is delivered. Electrogram analysis may be performed on a simultaneously acquired unipolar electrogram that is aligned to the bipolar electrogram pacing spike. If the electrogram is acquired with atrial pacing or native rhythm, then the preferred fiduciary is the onset of the R-wave as an indicator of onset of ventricular depolarization.

Figure 13:
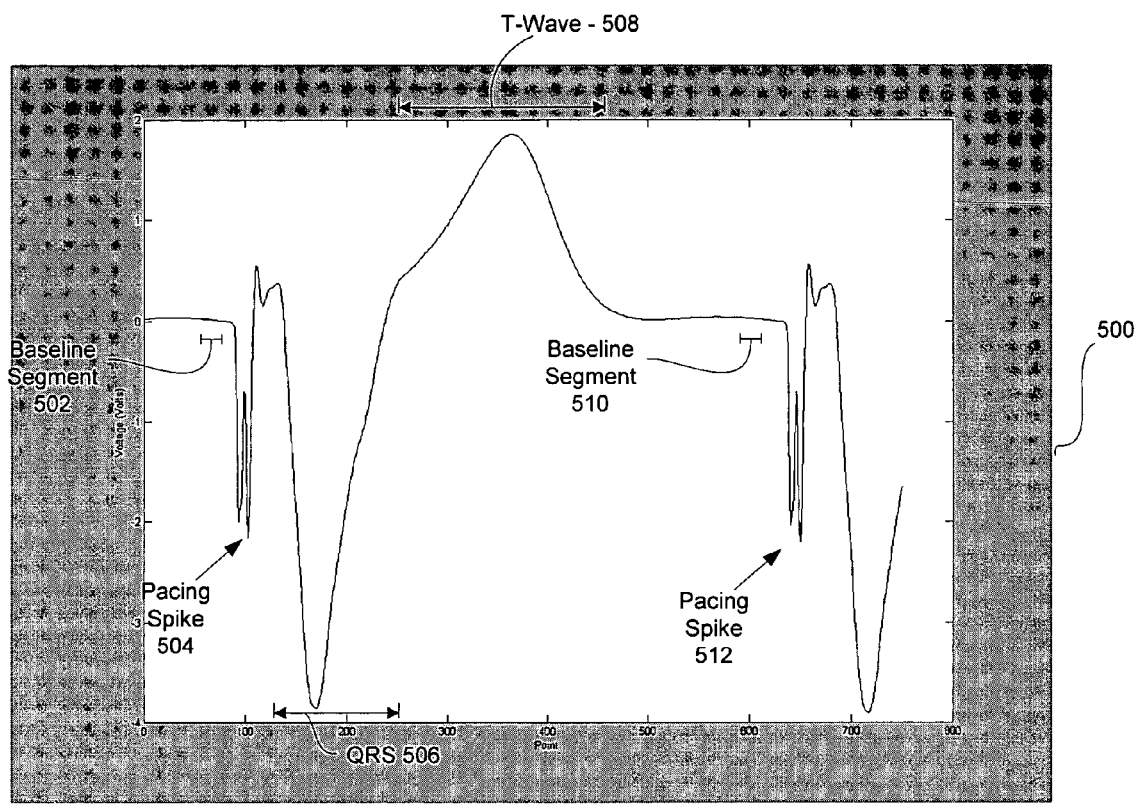
FIG. 13 shows an exemplary electrogram that is aligned to a pacing spike according to the present invention.

In step 165, the file is reformatted and aligned to the fiduciary. Each electrogram channel is reformatted from a 1-dimensional array (time) into a 2-dimensional array (cycle number, time). Further, the pacing pattern based on the timing between pacing spikes is determined. The electrogram for each cycle number starts at 100 ms prior to the pacing spike and continues to 650 ms after the pacing spike. Thus, each data segment contains 750 ms. For example, FIG. 13 shows electrogram 500 that is aligned to a pacing spike. The electrogram 500 includes a baseline segment region 502 in the 70–90 ms range, the pacing spike 504 around the 100 ms range, the QRS 506 in the 130–250 ms range and the T-Wave 508 in the 250–450 ms range. The electrogram 500 continues to have the next beat baseline segment 510 in the 590–610 ms range, the next beat pacing spike 512 around the 620 ms range, and the first portion of the next beat QRS starting at approximately the 650 ms range. The data segment (e.g., the data segment shown by ECG 500) is assigned a cycle number and stored in a 2-dimensional array. Those of skill in the art will understand that the ranges described above for the ECG 500 are only exemplary and approximate and each individual electrogram and analysis system will have its own unique characteristics.

Those of skill in the art will also understand that the raw electrogram data that is obtained in step 155 may go through some preprocessing prior to the identification step 160. The preprocessing may depend on the manner in which the electrogram data is collected. For example, two unipolar electrograms may be subtracted to create a third unipolar vector as part of the preprocessing.

Furthermore, the steps 160 and 165 may not need to be performed if the pacing device can record electrograms which are aligned to the timing of the pacing and the pacing pattern. If such recording can be performed, the fiduciary will be the timing of pacing and the pacing pattern itself. Therefore, the electrogram is implicitly aligned to the cardiac pacing and pacing pattern.

Referring back to FIG. 5a, in step 170, bad beats are identified and replaced so as not to corrupt the overall file. The identification of bad beats is determined by a sparse array created by sub-sampling an averaged beat. This array is then correlated to corresponding points on each individual beat. If the correlation coefficient (R-value) is less than 0.8 then the beat is considered bad. Alternative measures of degree of similarity between an average and individual beats may be chosen to identify bad beats. The replacement of bad beats procedure is designed to avoid disruption of the input (pacing pattern) and output (T-wave) relationship. For example, if the patient is being paced with the 4-beat pacing pattern ABCD and the bad beat is beat B, then the 4-beats replaced include the beat preceding the bad beat A, the bad beat B, and the two subsequent beats C and D. The replacement beat for A is calculated as the mean or median of the preceding 25 electrograms that result from paced beat A. This process is applied to all beats regardless of the pacing pattern. The number, temporal location and location relative to pacing pattern of bad beats is stored in a file so that the electrophysiologic conditions surrounding bad beats may be determined. For example, if there is a temporal cluster of bad beats, this may indicate a reaction by the particular patient which should be studied. A second sparse array is created by sub-sampling an averaged beat after replacement of bad beats to recheck the success of replacement of bad beats. This array is correlated to corresponding points on each individual beat and an R-value of less than 0.8 is considered bad. The R-value that is used for the second threshold may be higher than the original R-value. The various R-values may be parameters that are settable or adjustable by a user based on the individual electrograms.

Figure 14:
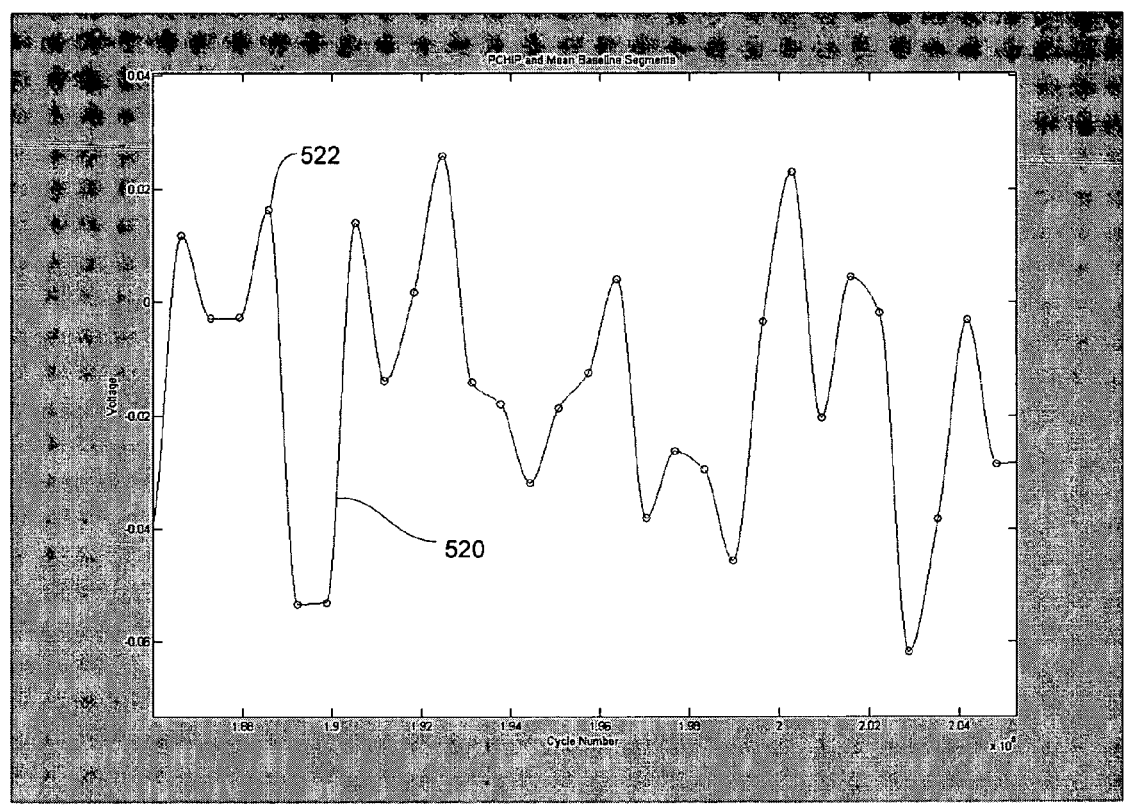
FIG. 14 shows an example of a piecewise cubic Hermite interpolating polynomial ("P-CHIP") curve applied to points representing a baseline segment for a series of cycles for the removal of baseline drift according to the present invention.

The process then continues to step 175 for an alignment of the baseline voltage. The electrogram region labeled baseline segment 502 in FIG. 13 immediately prior to the pacing spike 504 is considered to have zero voltage. The average voltage of the baseline segment consisting of points 70–90 that is also the 10–30 ms region prior to the pacing spike is found and used as a fiduciary point for interpolation between beats to remove any baseline drift. In the example of FIG. 13, the ECG 500 is created by recording data points every 1 ms, thus, each point is equivalent to 1 ms. Multiple methods are available to remove baseline drift such as linear interpolation and polynomial interpolation. In this example, a piecewise cubic Hermite interpolating polynomial ("P-CHIP") was applied to the set of fiduciary points to remove any baseline drift as is shown in FIG. 14. FIG. 14 shows an example of a P-CHIP curve 520 applied to points (e.g., point 522) representing the baseline segment for a series of cycles. Those of skill in the art will understand that a baseline drift will offset the voltage of the next cycle in the direction (positive/negative) and magnitude of the baseline drift. Removal of the baseline drift assures that cycles are consistent when further signal processing is performed on the cycles, e.g., summing, transforming, comparing, etc.

The above example of voltage alignment used a particular segment of the electrogram to remove baseline drift. However, any electrically stable portion of the electrogram may be used for the purpose of removing baseline drift. For intracardiac electrograms, the baseline drift correction may not be used. For example, if there is alternans in the baseline segment that is concordant with alternans in the region of interest, then baseline drift correction may not be desirable because it would reduce the magnitude of the apparent alternans.

Figure 27:
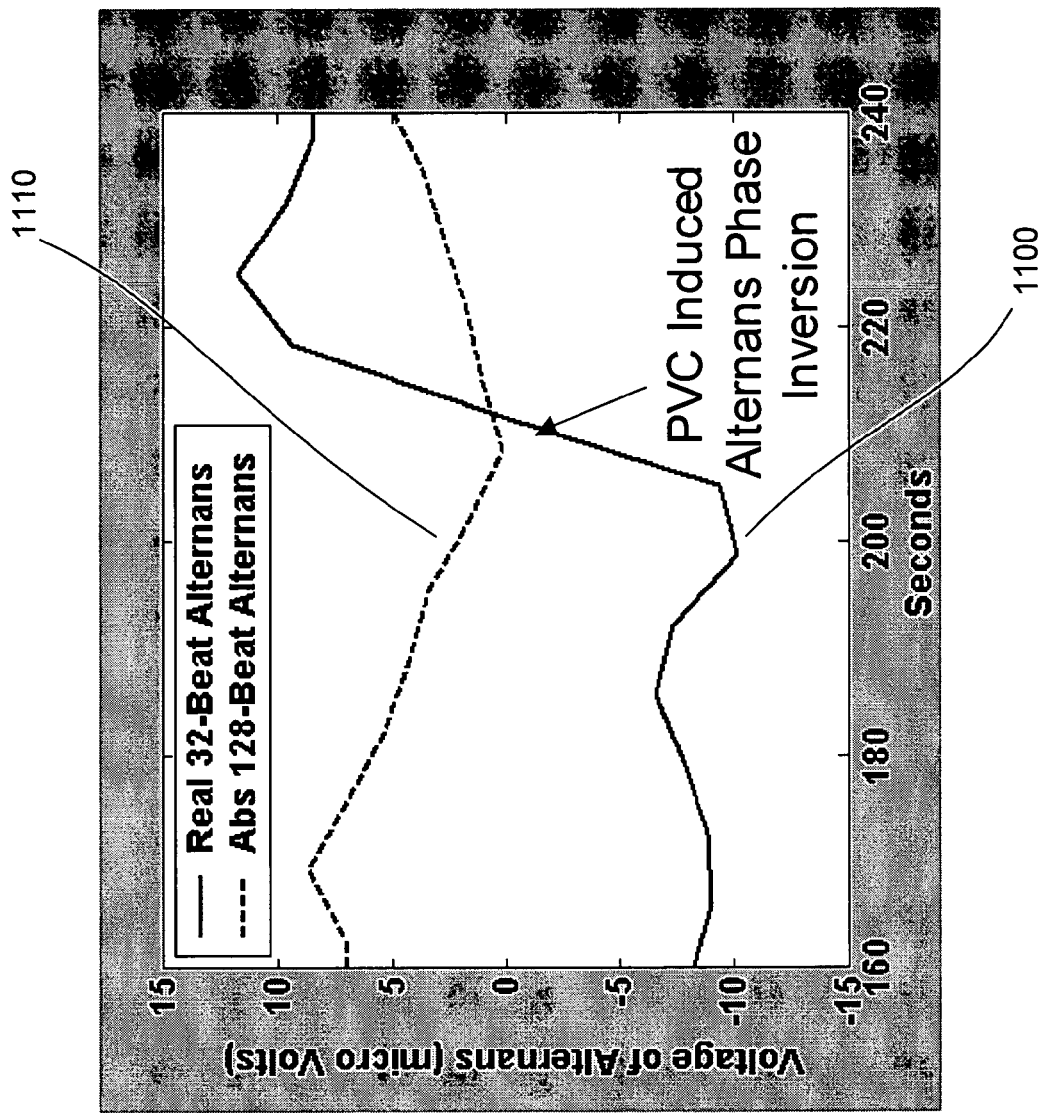
FIG. 27 shows an example of a PVC induced phase inversion in the presence of significant alternans.

In step 180, the alternans phase is synchronized. This step is critical to prevent the inability to identify significant alternans due to the presence of an alternans phase inversion. FIG. 27 shows an example of a PVC induced phase inversion in the presence of significant alternans. Curve 1100 shows the result of the real component of a 32-beat Fourier transformation at 0.5 cycles/beat. The PVC beat results in an alternans phase inversion from a negative 9 $\mu$V to a positive 9 $\mu$V. Curve 1110 shows the result of the absolute value of the 128-beat Fourier transformation at 0.5 cycles/beat. This curve 1110 illustrates a gradual reduction of alternans to zero, then a gradual increase in alternans. Thus, this figure depicts the failure to identify significant alternans at the time of an alternans phase inversion and a reduction of measurable alternans around the time of the alternans phase inversion. Further, this figure illustrates that using the real component of a relatively short segment Fourier transformation creates a sensitive method to identify the location of an alternans phase inversion.

Figure 28:
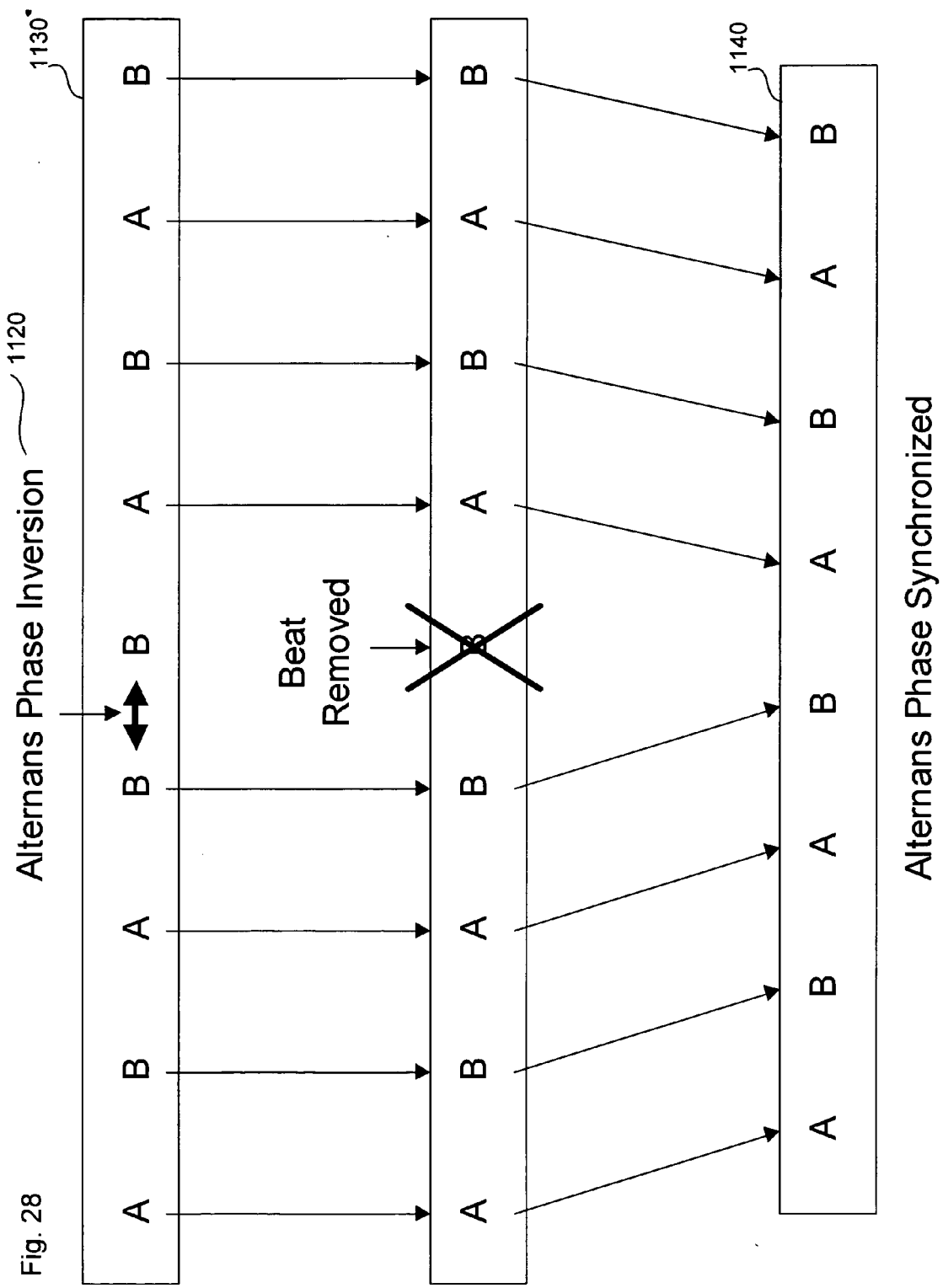
FIG. 28 illustrates the impact of removal of one beat at the location of an alternans phase inversion according to the present invention.

Again referring to step 180, the following process describes how the alternans phase is synchronized. Sequential overlapping short segment Fourier transformations with 4-beat steps are performed over the entire electrogram. In the example above, a 32-beat Fourier transformation was chosen. An alternans phase inversion is said to occur if the phase of the alternans is consistent, the magnitude is significant for a period and then transitions to the opposite phase with a significant magnitude. For example, a consistent alternans phase is present if there is a phase for 6 or 8 overlapping segments and a magnitude greater than a threshold value. If an alternans phase inversion occurs, then the location of the phase inversion is determined by the location where a consistent alternans phase changes to a consistent alternans opposite phase, i.e., positive to negative or negative to positive. One beat is removed at the site of the alternans phase inversion. This results in removal of the alternans phase inversion. FIG. 28 illustrates the impact of removal of one beat at the location 1120 of an alternans phase inversion. Removal of a beat at the location 1120 of the phase inversion results in conversion of an ABABBA-BAB pattern 1130 to an ABABABAB pattern 1140 where 'A' represents high T-waves and 'B' represents low T-waves as the components of alternans. Sequential overlapping Fourier transformation of longer segments of the entire electrogram will then be performed as described below for identification of the dynamics and magnitude of TWA as measures of electrophysiologic stability.

It should be noted that this step is generally not necessary where a resonant pacing pattern is being used because the resonant pacing pattern generally induces phase synchronization. If the resonant pacing pattern has variation of pacing that is of a low magnitude, it is possible for the resonant pacing pattern to fail to cause phase synchronization. The rational for resonant pacing criteria to control phase synchronization is explained with reference to FIGS. 26*a* and 26*b* in the above text. The level of variation of pacing required for resonant pacing to cause phase synchronization may be used to determine relative electrophysiologic stability. However, when a constant pacing pattern, a non-resonant pacing pattern or the native rhythm is being recorded as the electrogram, there may be alternans phase inversions due to slow oscillations of phase or due to premature or other bad beats. Further, when the alternans phase synchronization is applied to a non-resonant pacing pattern with an odd number of beats in the pattern, then the number of beats removed should be equal to the number of beats in the pacing pattern. This process prevents disruption of the impact of the pacing pattern.

The number of beats included in the Fourier transformation of step 180, alternans phase synchronization, includes the root of alternans, 2, and the root of the number of beats in the pacing pattern, e.g., 3, 4, 5, 6, etc. Choosing a segment length that includes the roots allow identification of the alternans while minimizing the impact of the pacing pattern on the measurement. The preferred number of beats in the Fourier transformation of step 180, alternans phase synchronization, is 32 when pacing with a constant rate, a 4-beat resonant pacing, or assessing native rhythm. The preferred number of beats in the Fourier transformation is 36 when pacing with the 3-beat non-resonant pacing pattern.

An alternative to performing a Fourier transformation in step 180, is to subtract the sum the magnitude of the voltage in the region of interest from the even beats from the odd beats. The sign of the difference between even and odd beats identifies the alternans phase. This alternative method requires fewer computations and is the preferred method for monitoring risk of VT/VF or cardiomyopathy using a pacemaker or ICD.

It should be noted that step 180, alternans phase synchronization, may be integrated with step 170, identification and replacement of bad beats. This is because bad beats are a common cause of alternans phase inversions and both sections deal with modification of beats. The choice of the timing of step 180, alternans phase synchronization depends on the impact of respiratory variation and other artifacts on the baseline and how those baseline changes impact the ability to detect the phase of alternans. The preferred approach for alternans phase synchronization when assessing the risk of VT/VF are the sequential steps 170, 175 then 180. Integration of steps 170 and 180 may be performed for monitoring of risk of VT/VF and cardiomyopathy if the baseline drift minimally impacts the alternans phase.

Referring back again to FIG. 5*a*, the end of step 180 (or 175 when a resonant pacing pattern is being used), the process provides data aligned to the fiduciary marking pacing or depolarization, the pacing pattern, and the phase of alternans over the entire electrogram. This aligned data is used to determine the time and frequency domain responses to cardiac pacing. From the time and frequency domain responses to pacing, the dynamics and magnitude of TWA as measures of electrophysiologic stability are identified. These measures of electrophysiologic stability are then used to determine the risk of VT/VF and the degree of cardiomyopathy. This fiduciary, pattern and alternans phase aligned data may be used directly to generate final time and frequency domain data for the patient. Using this data directly will be described in greater detail below. However, there are multiple exemplary methods for generating the final time and frequency domain data. Some of these methods require the identification of a region of interest within the electrogram data.

Figure 5B:
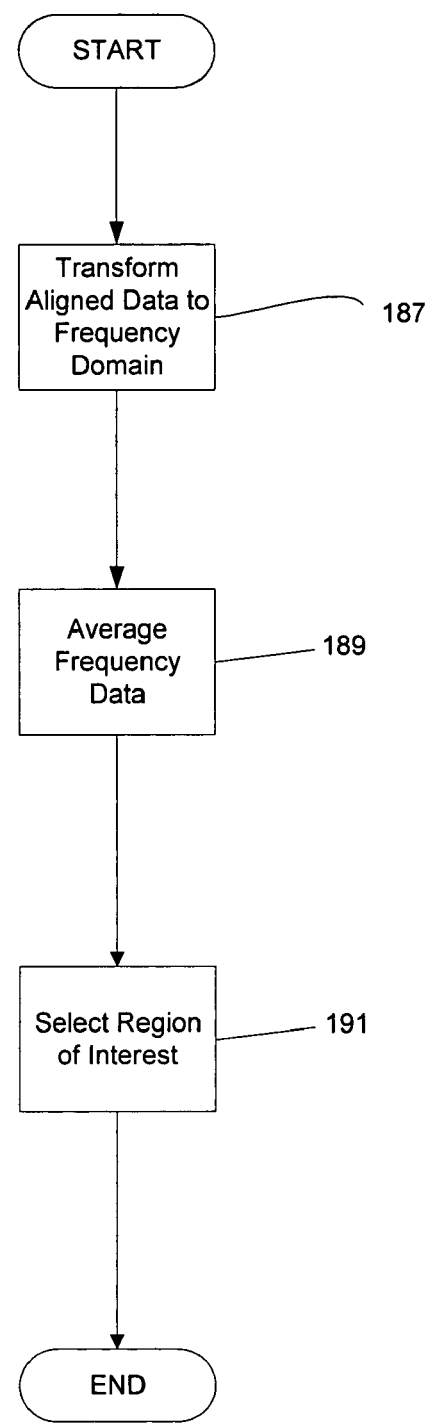
FIG. 5b shows an exemplary process for selecting a region of interest for an electrogram according to the present invention.

FIG. 5*b* shows an exemplary process 185 for selecting a region of interest of an electrogram. In step 187, the fiduciary, pattern and alternans phase aligned data which was generated by the process 150 of FIG. 5*a* is transformed from the time domain (the native domain of the electrogram data)

to the frequency domain. Those of skill in the art will understand that there are numerous manners of transforming time domain information into frequency domain information, e.g., Fourier Transforms, Fast Fourier Transforms, etc. The process of transforming from the time to the frequency domain consists of dividing the aligned electrograms into 10-ms average voltage bins. Sequential overlapping 64-ms beat Fourier transformations with 16-beat steps are then performed over the entire beat series for each of the 10-ms bins. As described above, the length of the Fourier transformation segment and the step must include the alternans root, 2, and the number of beats in the pacing pattern. Hence, for a 3-beat pacing pattern, 72-beat Fourier transformations would be chosen and 18-beat steps. The result of the transformation of step 187 is frequency domain data over the entire electrogram for sequential 64-beat segments.

Figure 29A:
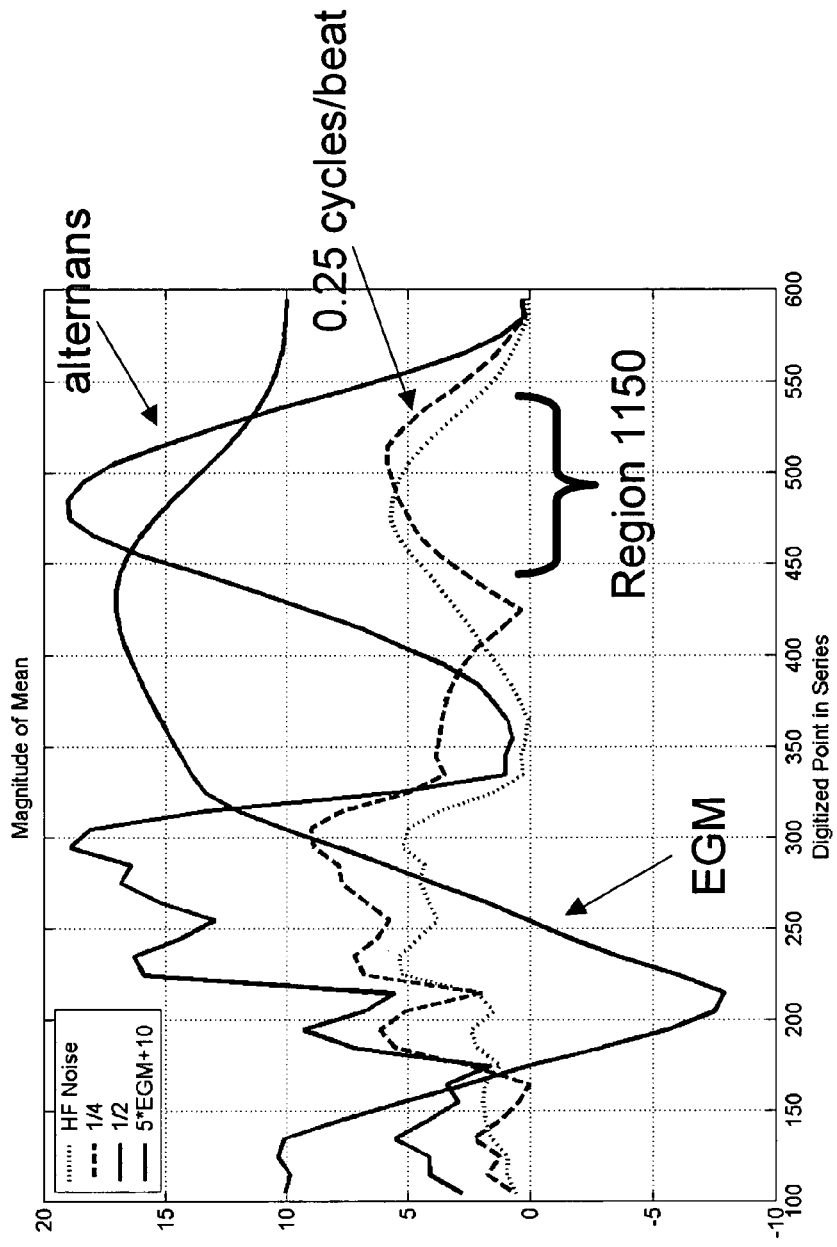
FIG. 29a shows the magnitude of the frequency composition of electrograms over time in the high frequency range and the averaged electrogram data according to the present invention.

In step 189, the average complex number frequency domain data is then determined in each of the 10-ms bins. Hence, at each 10-ms bin along the electrogram, the frequency composition of the electrogram response to the pacing pattern is determined. Since the source data was fiduciary, pattern and alternans phase aligned, the frequency domain data is also aligned to pacing pattern and alternans phase. Components of the raw electrogram that are not stationary relative to the pacing pattern or the alternans phase, e.g., respiratory artifact or random noise, will be averaged out of the signal over the large number of beats since the phase of the non-stationary elements will be variable. FIG. 29a shows the magnitude of the frequency composition of electrograms over time at 0.25, 0.5, the range 0.3–0.48 cycles/beat (high frequency range) and the averaged electrogram data from the step 189 using the second exemplary patient, i.e, the patient with heart failure and history of myocardial infarction. The averaging of the frequency data for the entire electrogram allows multiple frequencies to be analyzed for a determination of the region of interest.

Alternatively in step 189, if the location and contribution of the non-stationary elements of the signal is desired, then the average of the magnitude of the frequency domain data is determined in each of the 10-ms bins. By obtaining the magnitude only in this alternative process, the phase information is lost signal elements that are not synchronized to pacing remain in the signal. This will be described further detail below with reference to FIG. 7b reversal of order of steps 715 and 720. FIG. 29b shows the magnitude of the frequency composition of electrograms over time at 0.25, 0.5, the range 0.3–0.48 cycles/beat (high frequency noise) and the averaged electrogram data, in the frequency domain resulting from the second exemplary patient, i.e., the patient with heart failure and history of myocardial infarction. This figure demonstrates that the inclusion of the non-stationary components significantly increases the high noise measurement when compared to FIG. 29a.

In step 191, the region of interest is selected for the electrogram data. This selection is made based on the analysis of the average frequency data at each position along the electrogram. The region of interest is selected as a region along the electrogram where there is a high magnitude of alternans in the signal. Again referring to FIG. 29a, the location of the region of interest is selected as the region of the electrogram, region 1150, where there is a high magnitude of alternans in the repolarization range of the electrogram.

Referring back to FIG. 1, the next steps are to complete the electrogram analysis of step 20 and provide output results in step 30. Again, these steps may be performed using software within a signal processing or computing device. As described above, the goal of the diagnostic method according to the present invention is to quantify the cardiac electrophysiologic stability by assessing the impact of a minor change in cycle length within the repeated pacing pattern. The diagnostic method will quantify small changes in repolarization induced by a slightly premature beat and quantify the subsequent decay of the pacing induced oscillation. The primary focus of the diagnostic method is to determine final frequency domain data and/or final time domain data for the electrogram data. This final frequency/time domain data may then be used to generate and evaluate multiple stability indices for the patient in order to evaluate risk of VT/VF, monitor cardiomyopathy, or other cardiac disease.

Figure 7A:
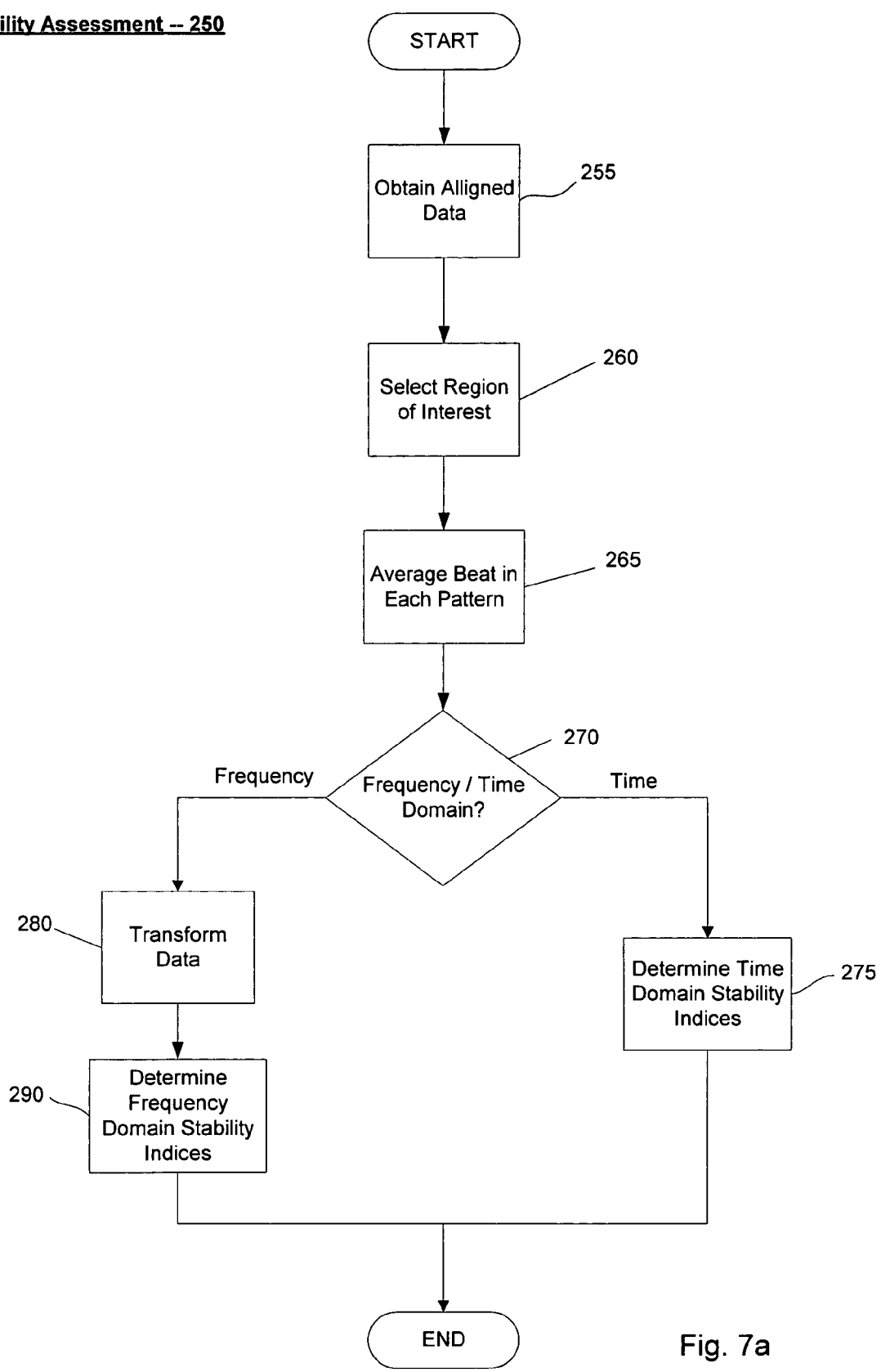
FIG. 7a shows a first exemplary process for assessing cardiac electrophysiologic stability according to the present invention.

FIG. 7a shows a first exemplary process 250 for assessing cardiac electrophysiologic stability. As described above, the stability assessment may be performed where a pacing pattern is being used or on the native heartbeat of the patient. For the process 250, the fiduciary, pacing pattern and alternans phase aligned data which was generated using the process 150 described with reference to FIG. 5a may be used as the data on which the process 250 operates as shown in step 255 where the aligned data is obtained.

In step 260, the region of interest is selected. The selection of the region of interest may be performed as described above with reference to FIG. 5b. Another manner of selecting the region of interest will be described with reference to the electrogram of FIG. 6a. This method comprises the subtracting of the fiduciary and pattern aligned data for the even and odd beats. This process is performed on sequential 16 or 24-beat segments. The average difference between even and odd beats at each of the time points along the electrogram, or fixed small intervals along specific regions of the electrogram, is determined and to obtain the short time scale oscillation ("Valtshort(1)"). The process is repeated for each sequential 16 or 24-beat series for the entire recording to identify Valtshort(2,3,4 . . . n). If the voltage of Valtshort (n) is negative at a fixed point in the predicted region of TWA, e.g., 350 ms after the pacing spike, then the sign is inverted. The mean Valt ("Valtmean") is calculated as the mean of all Valtshort. Valtmean curve 206 is used to identify region 204 that is the 100 ms region with the greatest mean alternans. This identifies the region of repolarization where the greatest amount of electrical instability occurs. Those of skill in the art will understand that the location of the alternans within an electrogram is partially dependent on how the electrogram is filtered. Thus, for intracardiac electrograms that have a higher high frequency filtering cutoff, the location of the apparent alternans may be displaced from the exemplary region shown in FIG. 6a. This alternative method requires fewer computations and is the preferred method for monitoring risk of VT/VF or cardiomyopathy using a pacemaker or ICD.

Figure 19:
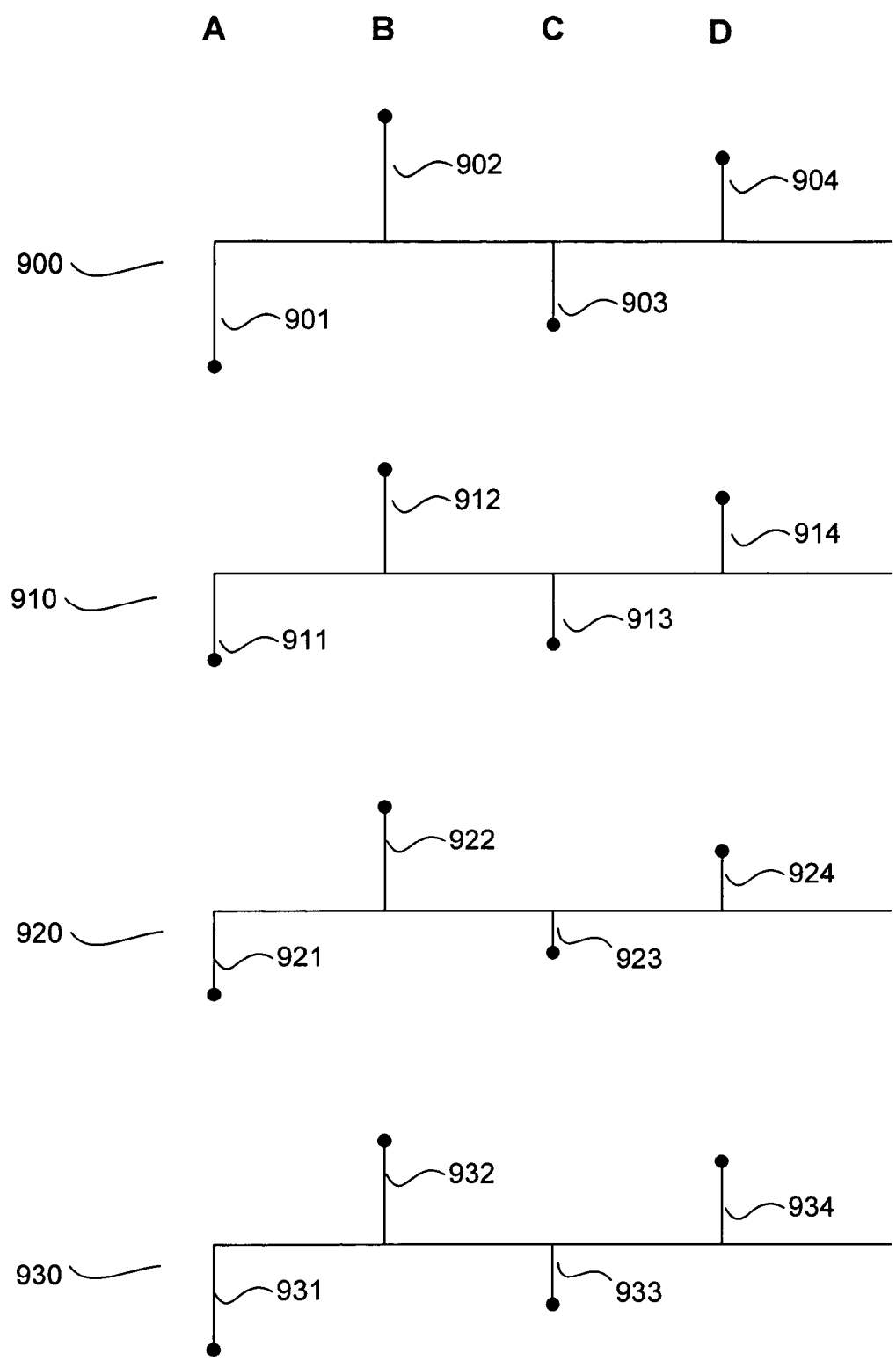
FIG. 19 shows exemplary beat patterns and an average beat pattern according to the present invention.

In step 265, the average beat for each beat in the pattern is found. This step will be described in more detail with reference to FIG. 19 which shows exemplary beat patterns 900, 910 and 920 and an average beat pattern 930. In this example, the patient is being paced with a 4 beat pattern pacing, i.e., pacing pattern A,B,C,D. Various resonant and non-resonant pacing patterns have been described above. Each beat pattern 900, 910 and 920 shows the mean voltage in the region of interest of the various beats for the particular beat pattern, e.g., beat pattern 900 has beat A mean voltage 901, beat B mean voltage 902, beat C mean voltage 903 and beat D mean voltage 904, beat pattern 910 has beat A mean voltage 911, beat B mean voltage 912, beat C mean voltage 913 and beat D mean voltage 914, beat pattern 920 has beat A mean voltage 921, beat B mean voltage 922, beat C mean voltage 923 and beat D mean voltage 924.

In this example, the phases of each of the beats (A,B,C,D) in the different beat patterns 900, 910 and 920 are aligned. When resonant pacing is being used this should be the case. However, in the case of non-resonant or constant pacing, the phases of the beats may not be aligned and thus, it may be necessary to invert the phase of various beats in order to make sure that all the phases are aligned. This phase inversion was described in more detail above with reference to step 180 in FIG. 5a.

Thus, each of the beats in the beat patterns 900, 910 and 920 may be averaged resulting in the average beat pattern 930 having the average of the mean voltage for the beats as follows: beat A average voltage 931, beat B average voltage 932, beat C average voltage 933 and beat D average voltage 934. Those of skill in the art will understand that the actual data may encompass many more beat patterns than the three shown in this example for the purposes of obtaining a significant statistical sample to find the average beats.

This averaging in step 265 provides the final time domain data for the patient's electrograms. As described above, the primary goal of the diagnostic method is to find the final time and/or frequency domain data. Thus, if the goal is to work in the time domain, the average time data determined in step 265 may be used as the final time domain data. As shown in step 270, the user of the process may select to work in either the time domain and/or the frequency domain. Again, as described above, the process may be performed using a signal processing device that is included in the pacing device, the device collecting the electrogram data or an independent device. Thus, the user of the process 250 may be the individual who programs these devices.

If it is selected to work in the time domain, in step 275, time domain stability indices may be found. There are any number of possible stability indices that may be derived from the final time data. These indices may be different for different patients or different conditions which a physician may be attempting to diagnose or monitor. Exemplary time domain indices of electrophysiologic stability are the overall magnitude of alternans, the magnitude of the response to the CL variation, the terminal magnitude of alternans in response to the pacing pattern, the rate of alternans decay (dV/dt), the rate of alternans decay modeled as composite of two different exponential decay rates, and the rate of alternans decay relative to the magnitude of alternans termed the TWSI, etc. An exemplary time domain index termed TWSI will be described below. Those of skill in the art will understand that other indices may be developed or recognized from the time domain information. For example, a pattern may be recognized in the time data for all patients who have a particular VF/VT condition. Thus, such a pattern may then be used as an indicator of the particular condition.

If the user decides to operate in the frequency domain, the process 250, continues to step 280 where the time domain average data is transformed from the time domain to the frequency domain by, for example, Fourier Transformation. This transformation provides the other goal of the process, i.e., final frequency domain data. The process may then continue to step 290 where frequency domain stability indices may be derived. Similar to the time domain stability indices, the frequency domain stability indices may vary by patient and condition. An exemplary frequency stability index may be the magnitude and phase response of the system at key frequencies, e.g., 0.5, 0.33, 0.25, etc. Additional exemplary frequency stability indices may be derived from combinations of the magnitude and the phase of the key frequencies, e.g., 0.5 and 0.25, or 0.5 and 0.33. Those of skill in the art will understand that other indices may be developed or recognized from the frequency domain information.

Figure 7B:
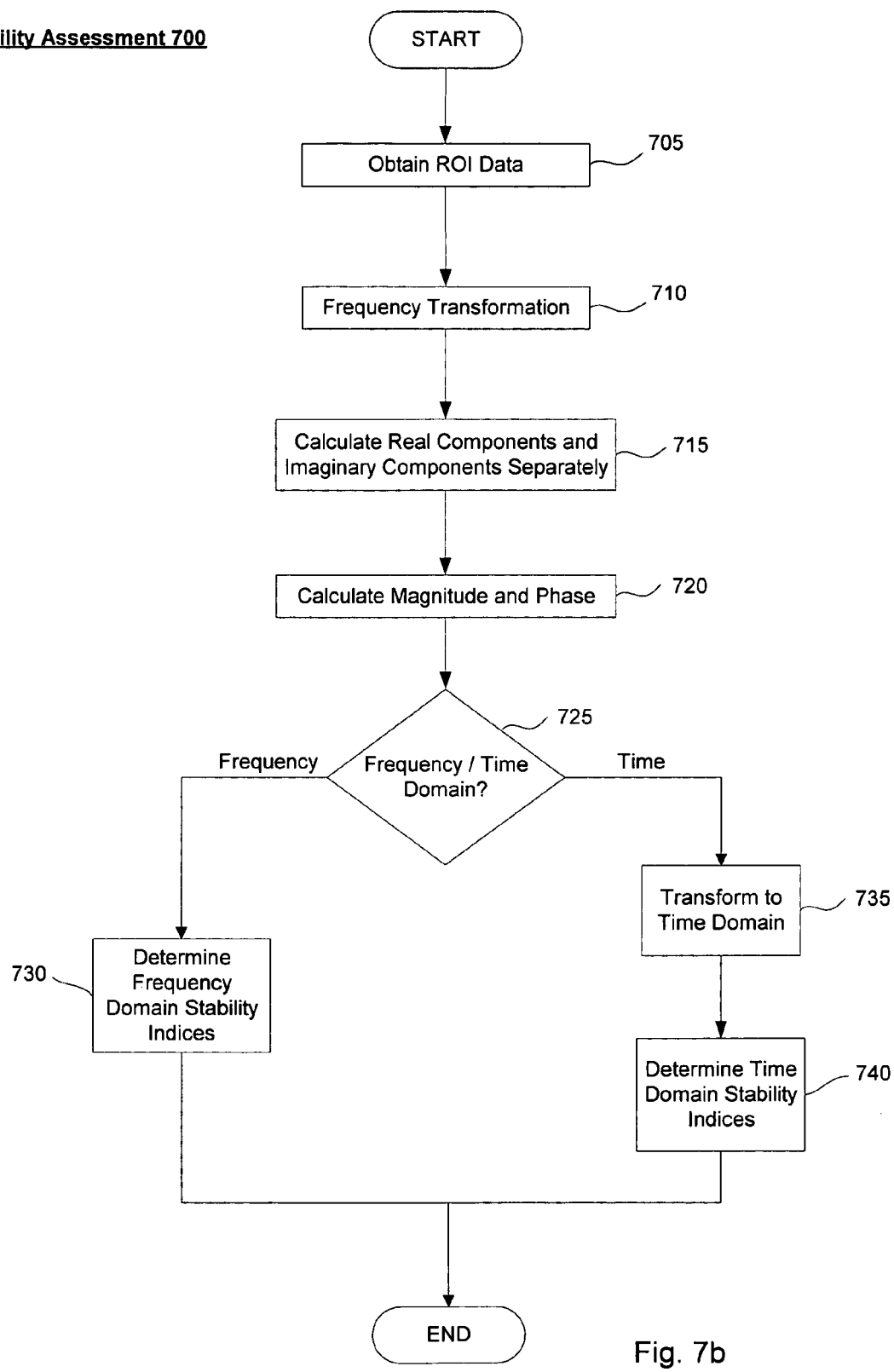
FIG. 7b shows a second exemplary process for assessing the cardiac electrophysiologic stability according to the present invention.

FIG. 7b shows a second exemplary process 700 for assessing the cardiac electrophysiologic stability either induced by an exemplary pacing pattern or the native heartbeat of the patient. In the first step 705, the fiduciary, pacing pattern and phase aligned data from the region of interest data is obtained. The mean voltage for each beat in the region of interest is obtained. This preprocessed region of interest data may be derived using the process 185 described with reference to FIG. 5b.

The process then continues to step 710 where the time domain data is transformed into frequency domain data. In this example, the frequency transformation is performed using a Fourier Transformation of a 72-beat segment with sequential 12-beat steps aligned to the pacing pattern over the entire range of recorded beats. The step interval is chosen to include a root of the pattern length and the frequencies of interest. In this example, a 12-beat step was chosen to allow analysis of 3-beat or 4-beat pacing patterns. The minimum beat step for the 4-beat pattern is a 4-beat step. The minimum beat step for the 3-beat pattern is a 6-beat step, i.e., two times three, so that the alternans frequency may also be analyzed. As will be described in greater detail below, the format of the output allows the physician to discern the response of the patient to the individual beats of the pacing pattern. Those of skill in the art will understand that 72-beat segments with sequential 12-beat steps is only exemplary and that the presently described method may be performed using other segment lengths and steps.

In step 720, the average real and imaginary components in the frequency domain are calculated separately at each frequency. The purpose of averaging the real and imaginary components separately is to eliminate non-stationary changes in the output data. Non-stationary changes are any components in the electrogram frequency spectra that are not contributed by a response to the pacing pattern. An example of a non-stationary change that may contribute to the electrogram signal is the impact of respiration on the electrogram because it will not be synchronized to the pacing pattern. Because the non-stationary changes are not synchronized both in magnitude and phase to the pacing pattern, the summation of the unsynchronized signal will include real and imaginary components distributed around zero such that the summation of these components approaches zero, thereby eliminating the effects of the unsynchronized signals and other noise components.

Figure 20:
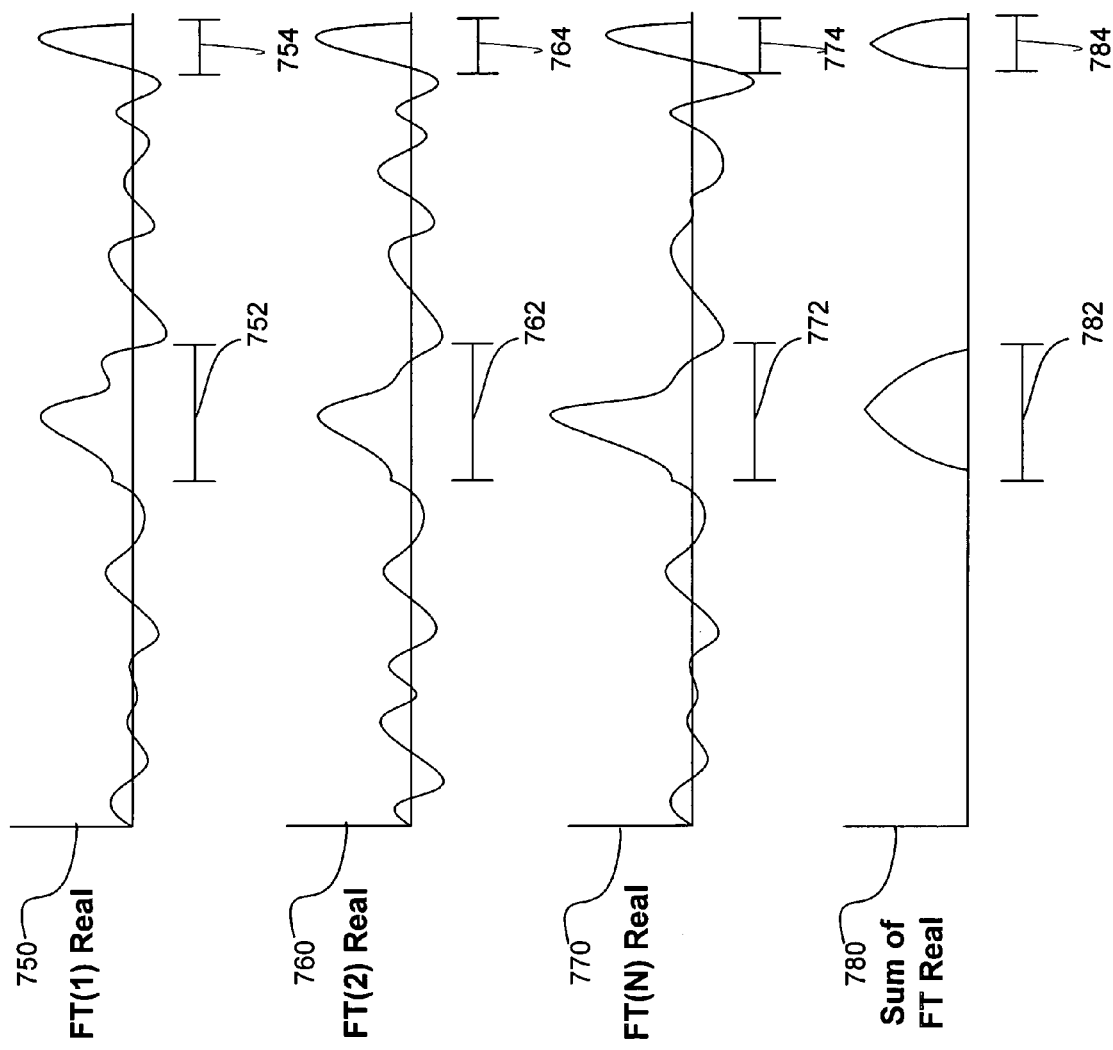
FIG. 20 shows a real component of an exemplary electrogram signal on four graphs according to the present invention.

In contrast, oscillations induced by the pacing pattern have real and imaginary components of the electrogram signal FT will have the same phase, i.e., pacing induced phase synchronization. Thus, identification of the average of the real and imaginary components allows for solving the magnitude and phase of the oscillations that are the result of the pacing pattern. For example, referring to FIG. 20 that shows a real component of an exemplary electrogram signal on four graphs 750, 760, 770 and 780. The first graph 750 shows the real component of the electrogram signal for the first FT segment e.g., a 72-beat segment. The graph shows that the real component of the signal is generally random, but has spikes in the area of frequency regions 752 and 754. In this example, the pacing pattern is expected to produce results in the frequency regions 752 and 754.

Similarly, the second graph 760 shows the real component of the electrogram signal for the second FT segment e.g., a 72-beat segment offset by a 12-beat step from the first segment. The graph shows that the real component of the signal is generally random, but has spikes in the area of frequency regions 762 and 764. Furthermore, the third graph 770 shows the real component of the electrogram signal for the Nth FT segment. Again, the graph shows that the real component of the signal is generally random, but has spikes in the area of frequency regions 772 and 774.

Finally, the final graph 780 shows the summation of the real components of all the FT segments. As described above, it is expected that the average of the frequency spectral components that are not a result of pacing will approach zero, while the average of the frequency spectral components that are a result of pacing will approach the true magnitude and phase in the complex plane for that pacing induced frequency response, e.g., those frequencies 782 and 784 of FIG. 20 where there is an expected response based on the pacing pattern. The same results would be expected for the imaginary components of the electrogram signal. Those of skill in the art will understand that there may be instances where the signals that are not about the frequencies of interest do not tend to zero and the physician may be interested in such signals because they may indicate some other factor which is inducing a non-random signal about a frequency unrelated to the pacing pattern. One such signal is the alternans signal when pacing with at odd numbered pacing pattern such as the exemplary 3-beat non-resonant pacing pattern. Alternans not produced by the pacing pattern, however may occur despite the pacing pattern and is desirable to identify.

Referring back to FIG. 7b, the process then continues to step 720 where the magnitude and phase of the averaged real and imaginary components are calculated. Steps 715 and 720 may be reversed to assess the non-stationary elements in the frequency spectra that are removed with the signal processing method described above. The utility of reversing steps 715 and 720 is discussed below. Thus, at the end of the step 720, the final frequency data has been determined. Similar to the process described above, the user may decide to work in the time domain or the frequency domain in step 725.

Using an alternative embodiment of step 720, the non-stationary components of the frequency domain may be monitored. These non-stationary elements may be desirable to monitor to assess the impact of respiration, the overall noise in the signal, and other cardiac disease processes such as myocardial ischemia. Specifically, myocardial ischemia may result in a characteristic pattern of increase in frequency domain complexity. In this alternative embodiment, the average magnitude of the frequency domain is calculated separately at each frequency. Since the phase is ignored by assessing the magnitude alone, signals that contribute to the frequency domain that are not synchronized to the pacing may be assessed. Referring back to region of interest selection process 185, separate regions of interest may be selected for monitoring the non-stationary components electrogram based on the location where the larger and/or smaller magnitudes of these components are temporally located in the electrogram.

If the user decides to work in the frequency domain, the process continues to step 730 where the frequency domain stability indices are determined. These indices may be the same as described above with reference to the process 250 of FIG. 7a. If the user desires to work in the time domain, the process continues to step 735 where the final frequency domain data is transformed into the time domain using, for example, an Inverse FT. The process then continues to step 740 where the time domain stability indices are determined. These indices may be the same as described above with reference to the process 250 of FIG. 7a.

Figure 21A:
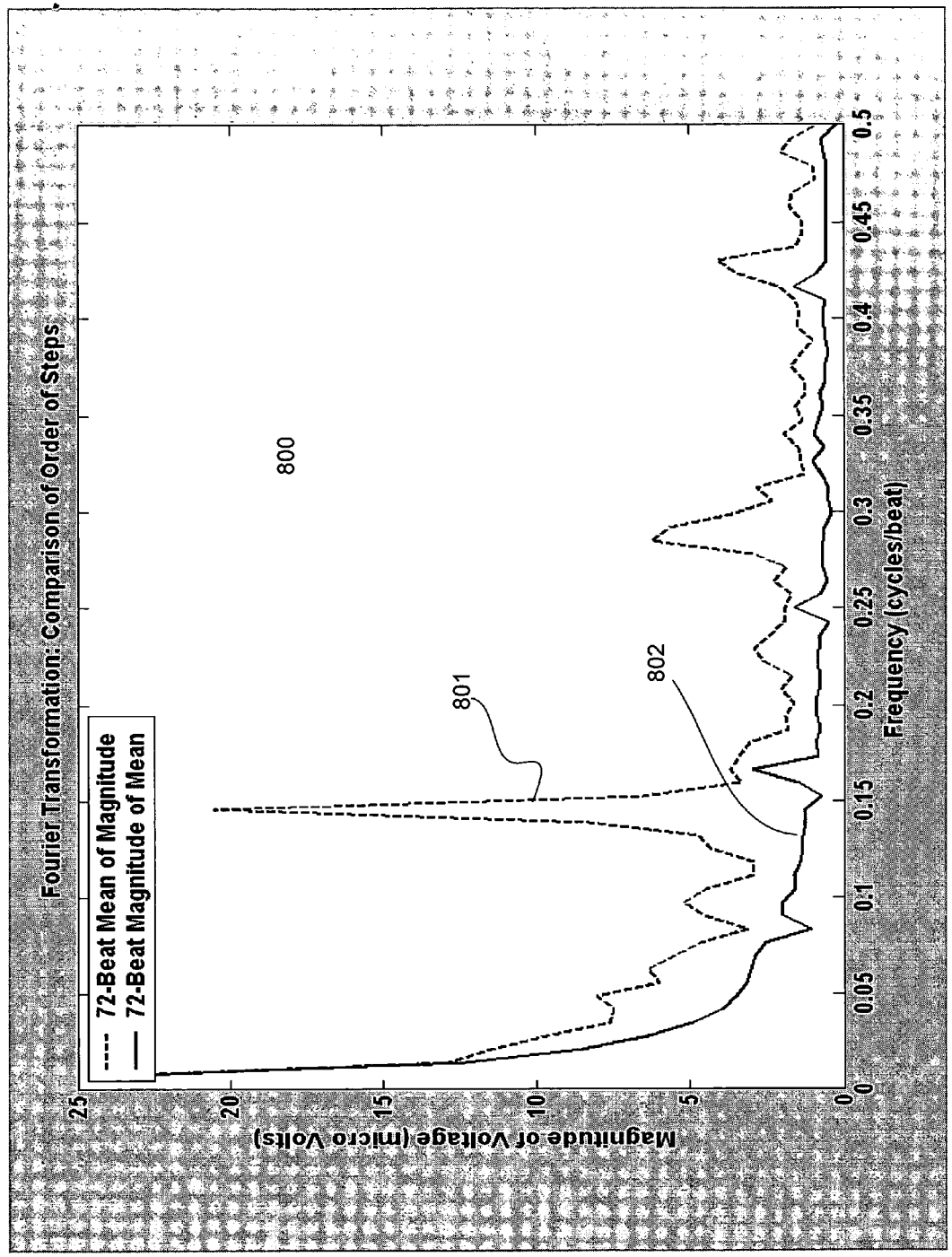
FIG. 21a shows an exemplary mean magnitude versus frequency graph for the first patient as a result of a constant 550 ms CL pacing according to the present invention.
Figure 30A:
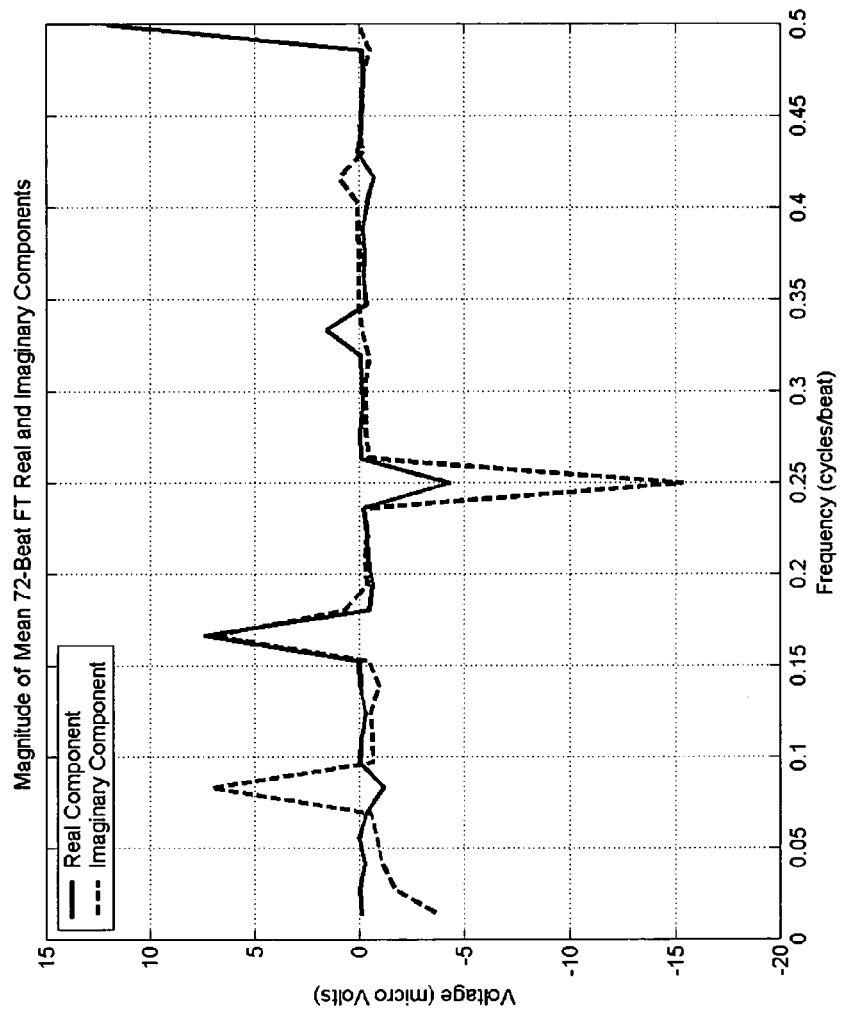
FIG. 30a shows exemplary final frequency data for a normal patient using the exemplary method described with reference to FIG. 7b.
Figure 30B:
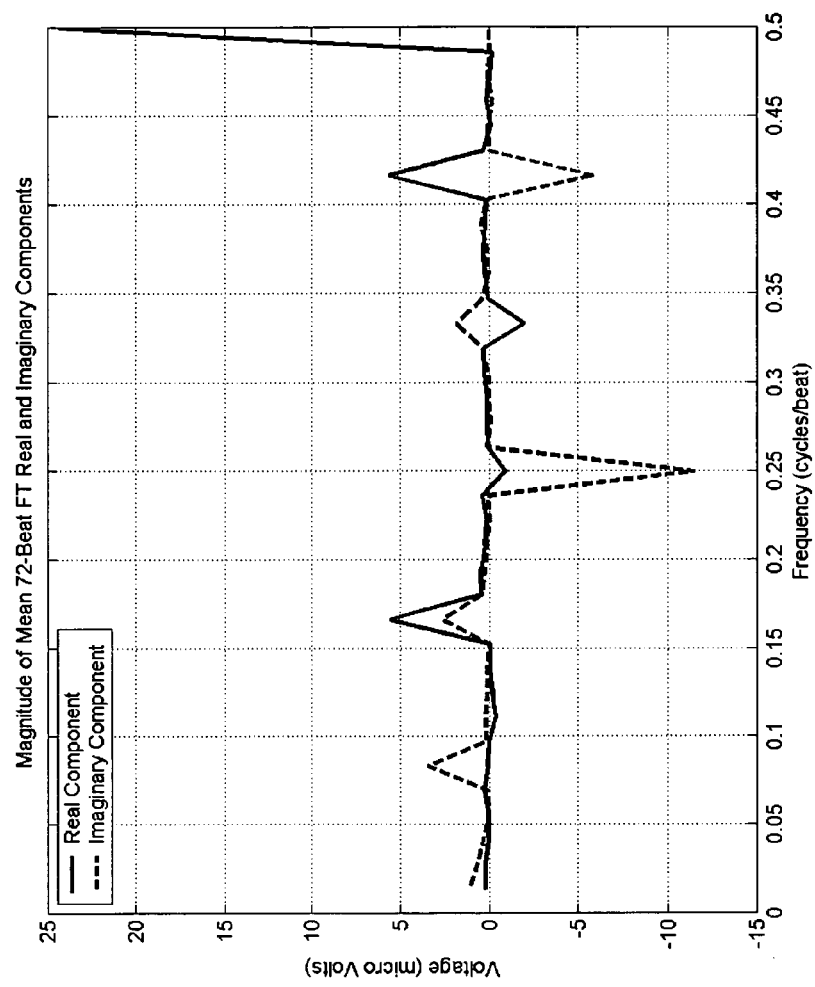
FIG. 30b shows exemplary final frequency data for a patient with heart failure using the exemplary method described with reference to FIG. 7b.

FIGS. 30a and 30b show exemplary final frequency data for patients using method 700 described with reference to FIG. 7b. Specifically, the real and imaginary components are maintained so that the phase information is not lost. Using and inverse Fourier transformation, the final frequency domain data may be converted to final time domain data. FIGS. 21–23 show the magnitude of the exemplary final frequency domain data for patients using the method 700 described with reference to FIG. 7b. In these examples, the patients 1 and 2 are the same patients described above. FIG. 21a shows an exemplary graph 800 with the frequency spectra curves 801 and 802 for the first patient, i.e., the patient exhibiting no signs of cardiac disease, as a result of a constant 550 ms CL pacing. Curve 801 is the average of the magnitude of the frequency spectra, i.e., steps 715 and 720 are reversed which results in inclusion of the non-stationary spectral components. The curve 801 demonstrates oscillations at 0.14 cycles/beat that is the expected result of respiratory modulation of the T-wave amplitude and oscillations at 0.28 and 0.42 that are the expected result of the phenomenon of spectral leakage from oscillations at 0.14 cycles/beat. Curve 802 is the magnitude of the average real and imaginary components of the frequency spectra. As described above, there is a marked reduction of the non-stationary spectral components. The peaks that are the result of respiratory modulation and spectral leakage of respiratory modulation are markedly reduced. As described previously, an area of interest at the frequency of 0.5 cycles/beat will show an increased magnitude in patients who have beat-to-beat oscillations of repolarization that occurs as a result of multiple cardiac disease processes. This patient shows a very low magnitude of T-wave oscillations across the entire frequency range and especially in the area of interest indicating that there is an absence of pacing induced oscillations of repolarization and normal cardiac electrophysiologic stability. It should be noted that for each of the FIGS. 21–23, the steps 715 and 720 of process 700 have been inverted to generate the dotted lines and the steps 715 and process 700 are in order to generate the solid lines. It is preferred that the process is carried out in the manner described with reference to FIG. 7b to analyze pacing induced oscillations, but the steps 715 and 720 may be inverted to analyze the sum of the pacing induced oscillations and the non-stationary components. A selection of the non-stationary components may be used assess noise components such as white noise in the signal, the impact of respiration on the electrogram, or other cardiac disease processes in the region of interest.

Figure 21B:
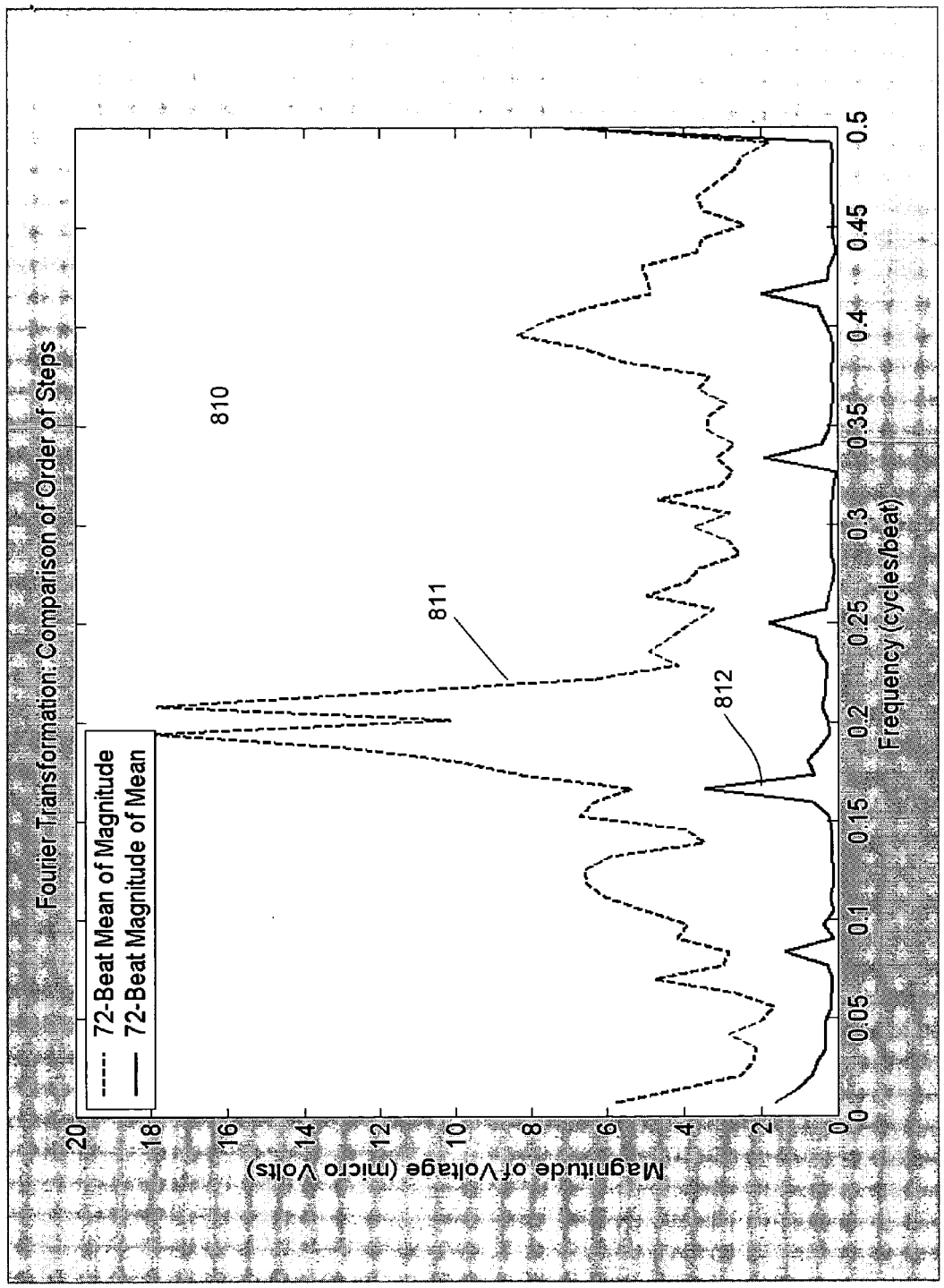
FIG. 21b shows an exemplary mean magnitude versus frequency graph for the second patient as a result of a constant 550 ms CL pacing according to the present invention.

FIG. 21b shows an exemplary graph 810 with the frequency spectra curves 811 and 812 for the second patient, i.e., the patient exhibiting signs of cardiac disease, as a result of a constant 550 ms CL pacing. Curve 811 is the average of the magnitude of the frequency spectra and curve 812 is the magnitude of the average real and imaginary components of the frequency spectra. In this patient, curve 811 demonstrates significant respiratory modulation of the T-wave at 0.2 cycles/beat with spectral spread to 0.4 cycles/beat. Curve 812 demonstrates a marked reduction of theses non-stationary components. Both curves demonstrate significant magnitude at 0.5 cycles/beat indicating the presence of T-wave alternans. Curve 812 also demonstrates a marked reduction in noise due to non-stationary components and spectral leakage of 0.5 cycles/beat to other frequencies. The presence of oscillations at 0.5 cycles/beat at the constant pacing pattern indicates a level of disease that the physician may desire to assess further or intervene upon.

Figure 22A:
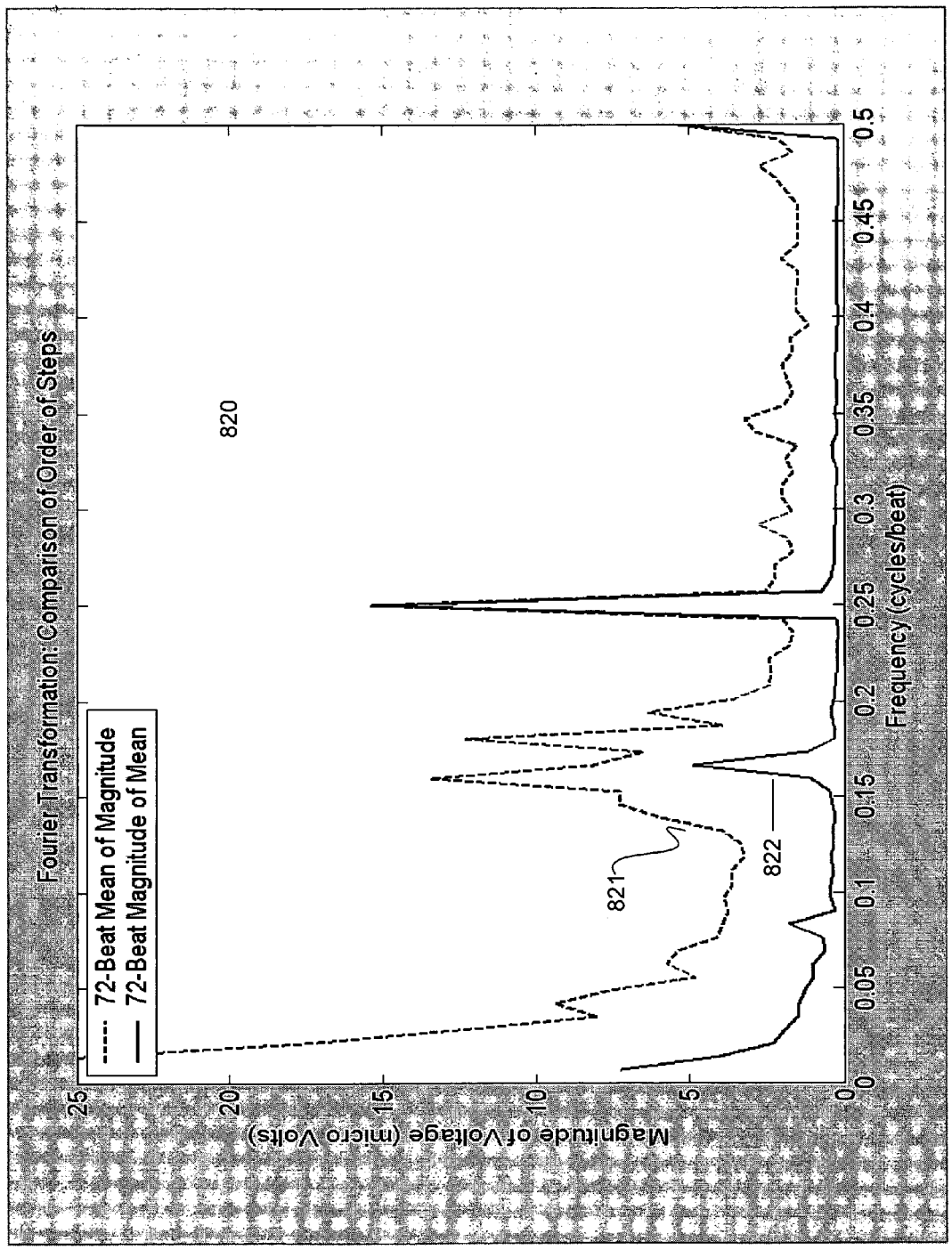
FIG. 22a shows an exemplary mean magnitude versus frequency graph for the first patient as a result of a 4-beat resonant pacing pattern according to the present invention.

FIG. 22a shows an exemplary graph 820 with the frequency spectra curves 821 and 822 for the first patient as a result of the 4-beat resonant pacing pattern 50 described with reference to FIG. 2. Curve 821 is the average of the magnitude of the frequency spectra and curve 822 is the magnitude of the average real and imaginary components of the frequency spectra. The graph shows the presence of oscillations of repolarization at 0.25 and 0.5 cycles/beat. Since the pacing pattern is a 4-beat resonant pacing pattern with a slightly premature beat at every fourth beat, the physician can infer that the premature beat is the fourth beat that contributes to the large magnitude of T-wave oscillation at 0.25 cycles/beat. As described earlier, the measure of the system stability is the ability of the heart to dampen induced oscillations. The oscillation at 0.5 cycles/beat is the frequency of T-wave alternans. An exemplary derived measure of electrophysiologic stability from the final frequency domain data is described below, however other derived measures may be obtained from the final frequency domain data. The ability of the system to dampen the pacing induced oscillations may be measured by the relative and absolute magnitudes of oscillation at 0.25 and 0.5 cycles/beat. As shown by the graph 820, the healthy heart is able to dampen the oscillations significantly resulting in the small magnitude at 0.5 cycles/beat relative to the larger magnitude at 0.25 cycles/beat.

Figure 22B:
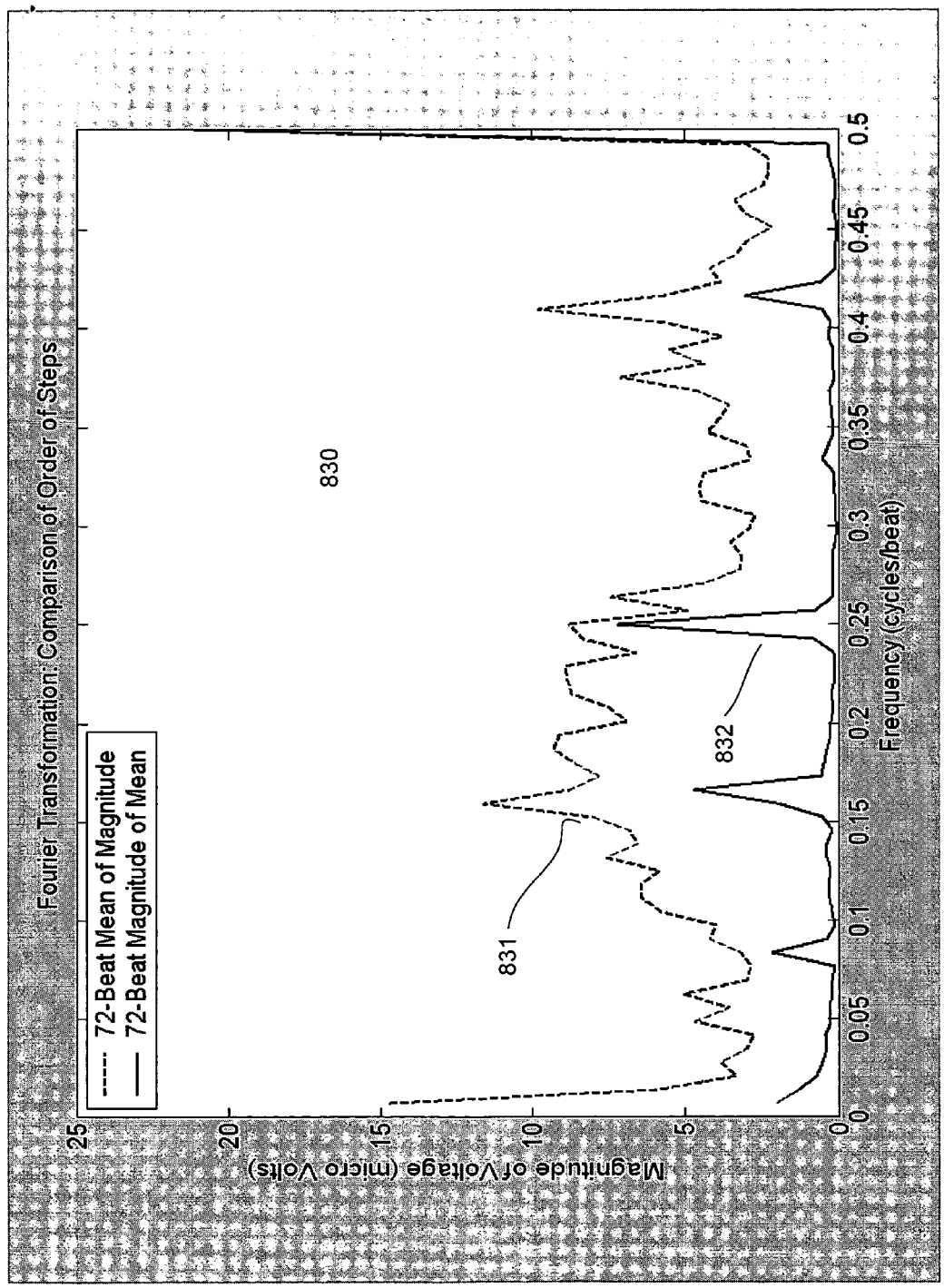
FIG. 22b shows an exemplary mean magnitude versus frequency graph for the second patient as a result of a 4-beat resonant pacing pattern according to the present invention.

In contrast, FIG. 22b shows an exemplary graph 830 with the frequency spectra curves 831 and 832 for the second patient as a result of the 4-beat resonant pacing pattern 50 described with reference to FIG. 2. Curve 831 is the average of the magnitude of the frequency spectra and curve 832 is the magnitude of the average real and imaginary components of the frequency spectra. Similar to graph 820, there is an increased magnitude in the frequency spectra at 0.25 cycles/beat that represents the contribution of the premature beat every fourth cycle and at 0.5 cycles/beat that represents the magnitude of ongoing repolarization alternans. Importantly, the magnitude at 0.5 cycles/beat is much greater than the magnitude at 0.25 cycles/beat in curve 832 of the second patient with heart disease which is a reversed relationship when compared to the first patient without heart disease. This is because the diseased heart as a system has less ability to dampen the oscillations. Rather, the oscillations build-up and increase significantly at the 0.5 cycles/beat frequency relative to 0.25 cycles/beat indicating that the heart has less relative electrophysiologic stability.

Figure 23A:
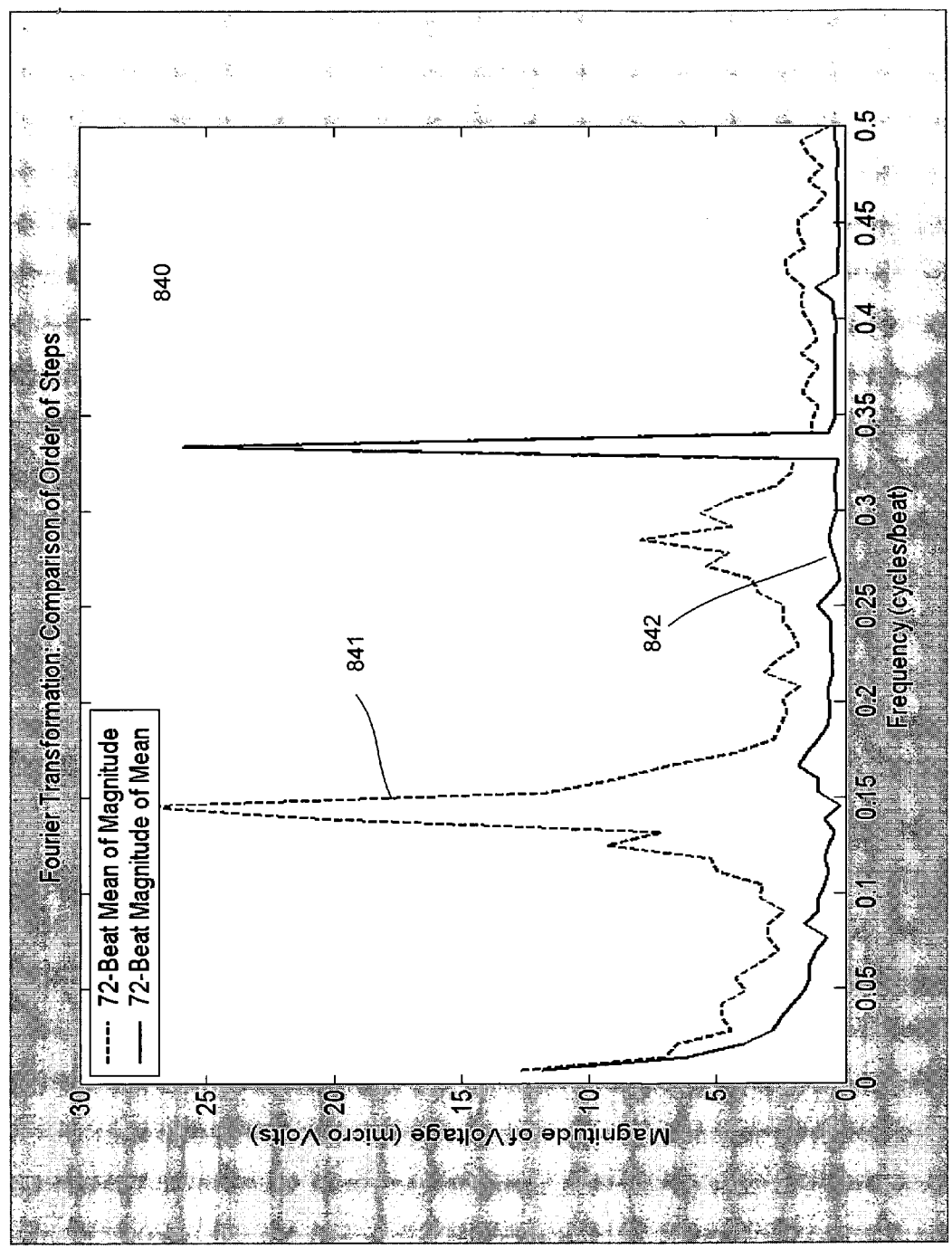
FIG. 23a shows an exemplary mean magnitude versus frequency graph for the first patient as a result of a 3-beat non-resonant pacing pattern according to the present invention.

FIG. 23a shows an exemplary graph 840 with the frequency spectra curves 841 and 842 for the first patient as a result of the 3-beat non-resonant pacing pattern 85 described with reference to FIG. 4a. Curve 841 is the average of the magnitude of the frequency spectra and curve 842 is the magnitude of the average real and imaginary components of the frequency spectra. Similar to the 4-beat pacing pattern, the 3-beat pacing pattern induces an oscillation of the T-wave for every third beat, i.e., the premature beat for the 3-beat pacing pattern. In this case, the signal for every third beat occurs at the frequency of 0.333 cycles/beat. The segment length 72 was chosen to include a root of three so that the Fourier transformation would solve for the magnitude at the frequency of 0.333 cycles/beat. The design feature of inclusion of the root of the frequency of interest in the segment length is important to the exemplary embodiment of this invention. A segment length that dose not include the root 3, e.g., 64 or 128, would not solve for the magnitude at the frequency of 0.333 cycles/beat. Thus, once again, the physician may determine the heart's electrophysiologic stability based on the ability of the system to manifest a response at 0.333 cycles/beat that indicates the ability of the system to be controlled by pacing. The 3-beat pacing pattern as graph 840 shows is notable for not inducing oscillations of repolarization at the alternans frequency of 0.5 cycles/beat.

Figure 23B:
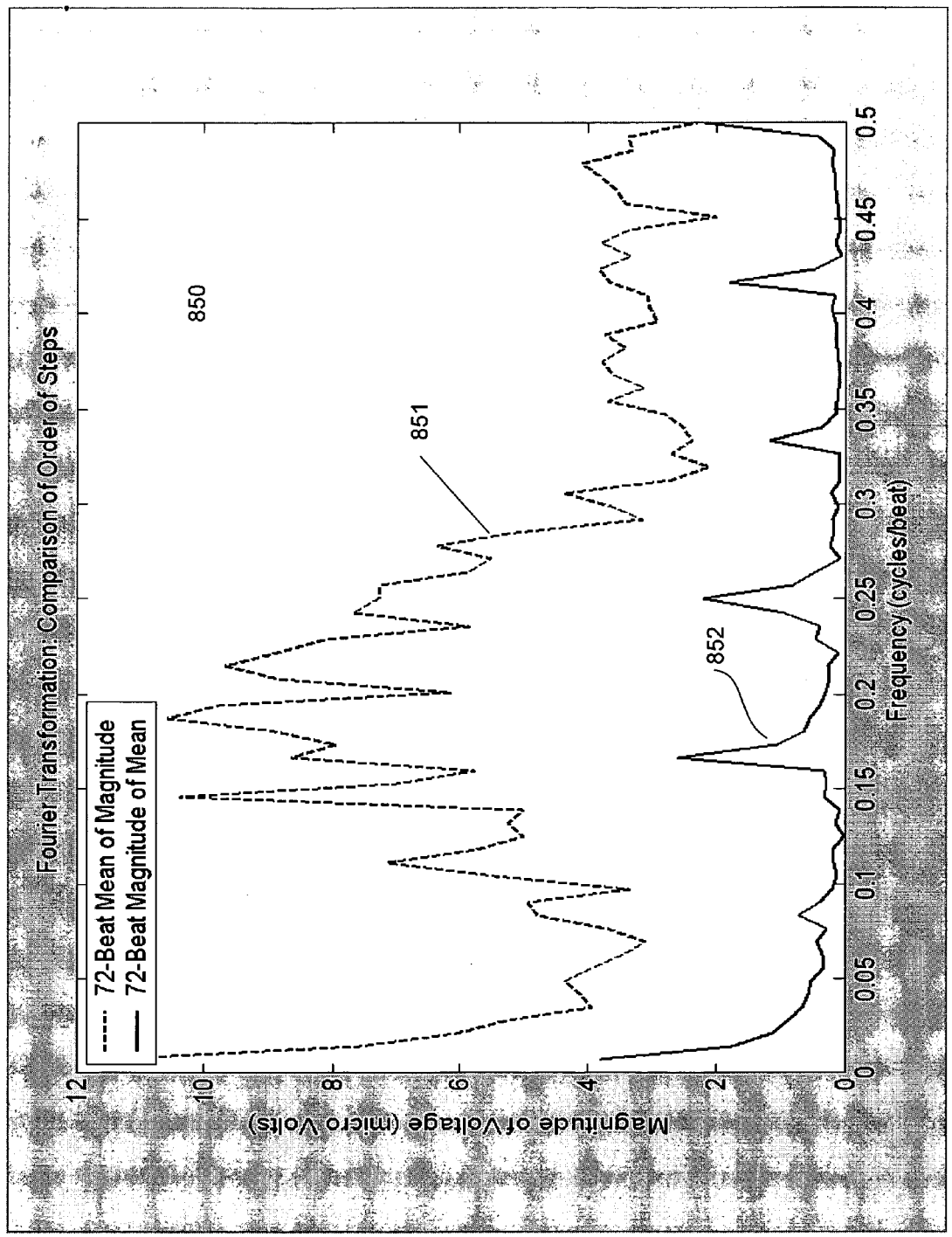
FIG. 23b shows an exemplary mean magnitude versus frequency graph for the second patient as a result of a 3-beat non-resonant pacing pattern according to the present invention.

FIG. 23b shows an exemplary graph 850 with the frequency spectra curves 851 and 852 for the second patient as a result of the 3-beat non-resonant pacing pattern 85 described with reference to FIG. 4a. Curve 851 is the average of the magnitude of the frequency spectra and curve 852 is the magnitude of the average real and imaginary components of the frequency spectra. As can be seen from this graph, the 3-beat pacing pattern has a much smaller magnitude at 0.333 cycles/beat on curve 852 when compared to the first patient curve 842. This indicates that the 3-beat pattern has less ability to control the system with pacing. Additionally, there are small oscillations 0.1666 (⅙), 0.25 (¼), 0.42 (5/12) and 0.5 (½) cycles/beat that indicates the presence of oscillations at these frequencies or the artifact of spectral leakage. The magnitude at the frequency 0.5 is significantly lower than the previous magnitudes at this frequency for the second patient as shown in FIGS. 21b and 22b. Thus, the 3-beat non-resonant pacing pattern is suppressing oscillations of repolarization at the alternans frequency of 0.5 cycles/beat. Similar to the ratio of magnitudes of the frequency spectra at 0.25 and 0.5 cycles/beat in response to the 4-beat resonant pacing pattern described above, the ratio of magnitudes of the frequency spectra at 0.333 and 0.5 cycles/beat in response to the 3-beat non-resonant pacing pattern may be used as a measure of relative electrophysiologic stability. Additional information on the therapeutic benefits of cardiac pacing patterns will be described below.

Figure 7C:
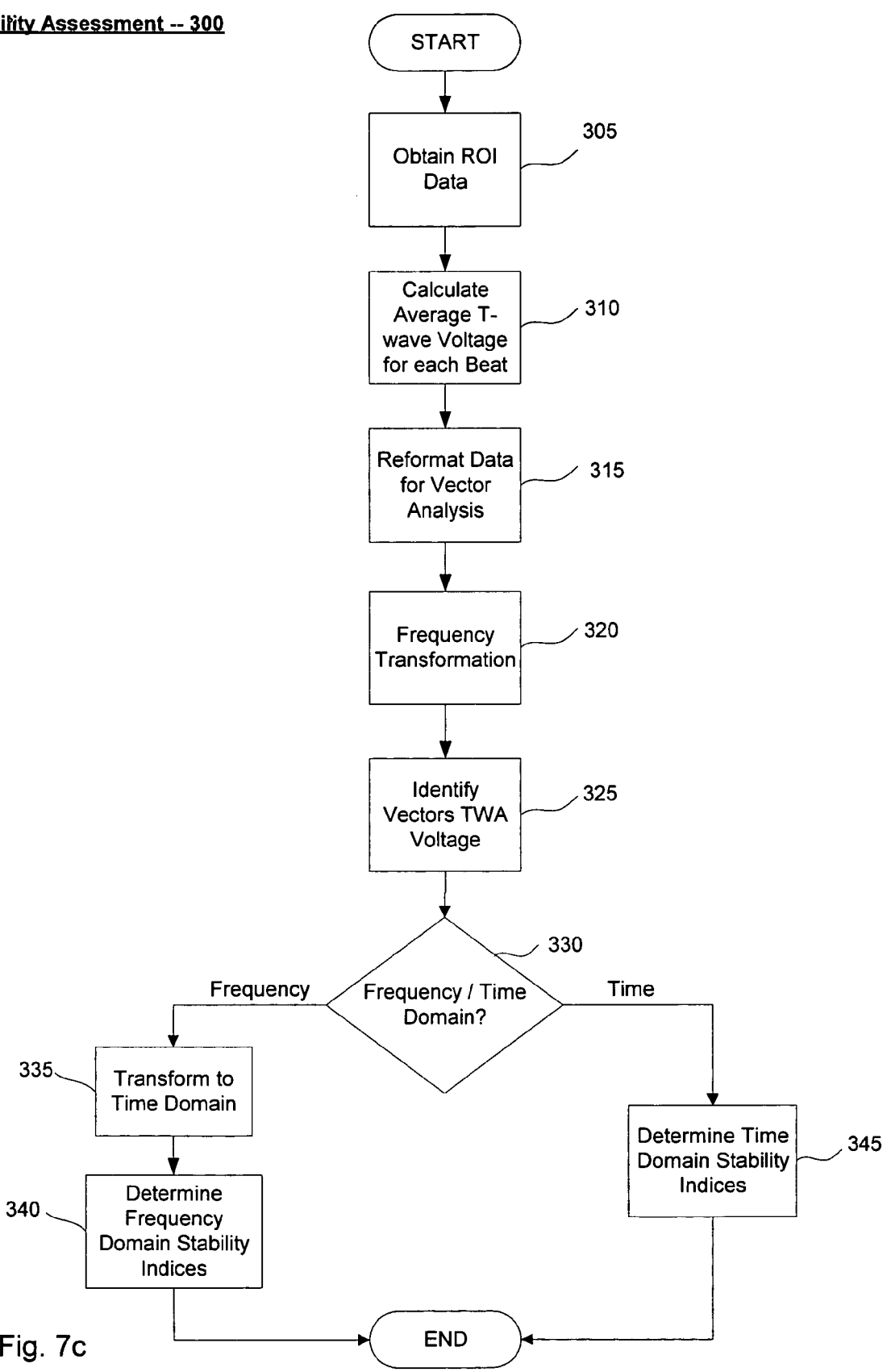
FIG. 7c shows a third exemplary process for assessing the cardiac electrophysiologic stability according to the present invention.

FIG. 7c shows a third exemplary process 300 for assessing the cardiac electrophysiologic stability using an exemplary pacing pattern or the native heartbeat of the patient. The process 300 of FIG. 7c is a follow on process to the process 150 described with reference to FIG. 5a, i.e., the process 300 will use the data generated by the process 150.

The process 300 will be described using an example of applying a repeated pacing pattern to two (2) sample patients. The repeated pacing pattern will be the resonant 4-beat pacing pattern 50 described with reference to FIG. 2, i.e., an A, B1, B2, B3 pattern which has a premature A beat at 535 ms and normal B beats at 555 ms. The first sample patient is the patient described above with reference to the electrograms 200 and 210 of FIGS. 6a–b, respectively, i.e., a patient exhibiting no signs of any cardiac disease. The second sample patient is the patient described above with reference to the electrograms 220, 230 and 240 of FIGS. 6c–e, respectively, i.e., a patient with coronary artery disease and heart failure after myocardial infarction.

The first step 305 of process 300 is to obtain the fiduciary, pacing pattern and phase aligned data from the region of interest data that may be derived using the process 185 described above. In step 310, the average T-wave voltage is calculated for each beat in the region of interest. The process then continues to step 315, where data arrays are reformatted so that a Fourier Transformation of the new data array will identify the impact of each beat within the pacing pattern. This is accomplished by sub-sampling the average T-wave voltage array to create four vectors: A-B1, B1-B2, B2-B3, and B3-A. These four vectors correspond to the change of the T-wave voltage between each of the adjacent beats. Those of skill in the art will understand that the use of a Fourier transform for the conversion of data from the time domain to the frequency domain is only exemplary. There are other computational methods for identifying the frequency content of a signal, e.g., Laplace transforms, Fast Fourier transforms, Wavelet transforms, complex demodulation, etc.

Figure 15:
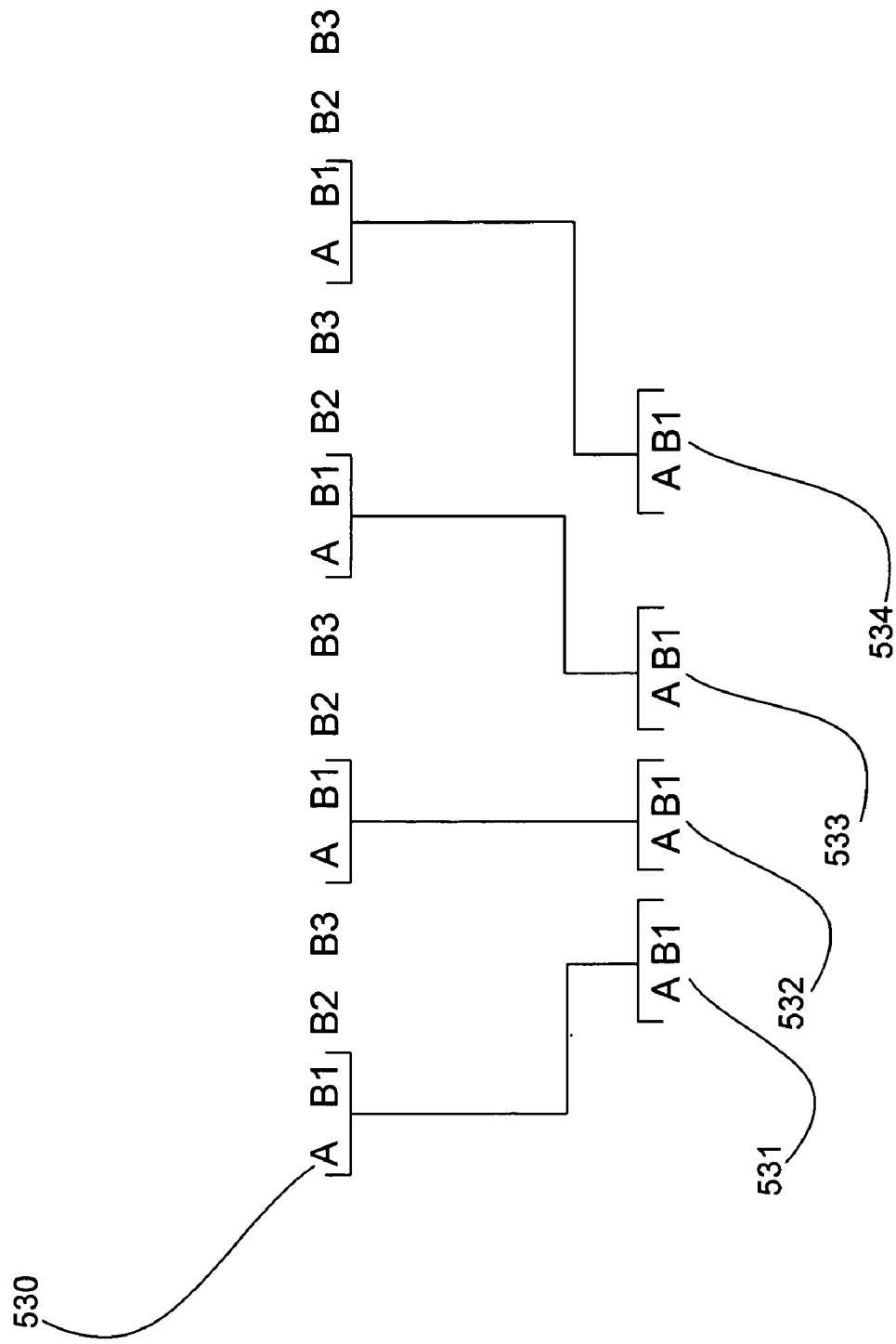
FIG. 15 shows an example of the sub-sampling of the beat T-wave voltage to create a vector corresponding to the change of T-wave voltage between each of the adjacent beats according to the present invention.

FIG. 15 shows an example of the sub-sampling of the beat T-wave voltage to create a vector corresponding to the change of T-wave voltage between each of the adjacent beats. In this example, four complete loops of the pacing pattern 50 (A, B1, B2, B3) are shown. Each beat represents a value for the average T-wave voltage for the beat as calculated in step 310 of process 300. In this example, the calculation for the vector A-B1 is performed to determine the change of the T-wave voltage between the beats A-B1. Four subsamples 531–534 are shown for the vector A-B1. Those of skill in the art will understand that the subsample will include the entire recorded series. In the same manner, the vectors B1-B2, B2-B3 and B3-A will also be determined.

In step 320, a conversion from time domain to frequency domain is performed on sequential overlapping segments for each of the four vectors created in step 315. In the exemplary method, a 60-beat segment length was chosen. In the exemplary method, a Fourier Transformation ("FT") used to convert the data from the time domain to the frequency domain. A FT is performed on a 60-beat segment consisting of cycles 1 through 60. The next data segment that a FT is then performed on consists of cycles 13 through 72, that is an overlapping segment generated by moving down 12 cycles. This process is repeated until the complete series of beats is analyzed. Those of skill in the art will understand that the use of a 60-beat segment and the 12-beat step is only exemplary and that the method according to the present invention may identify segments and steps of varying lengths.

Figure 16:
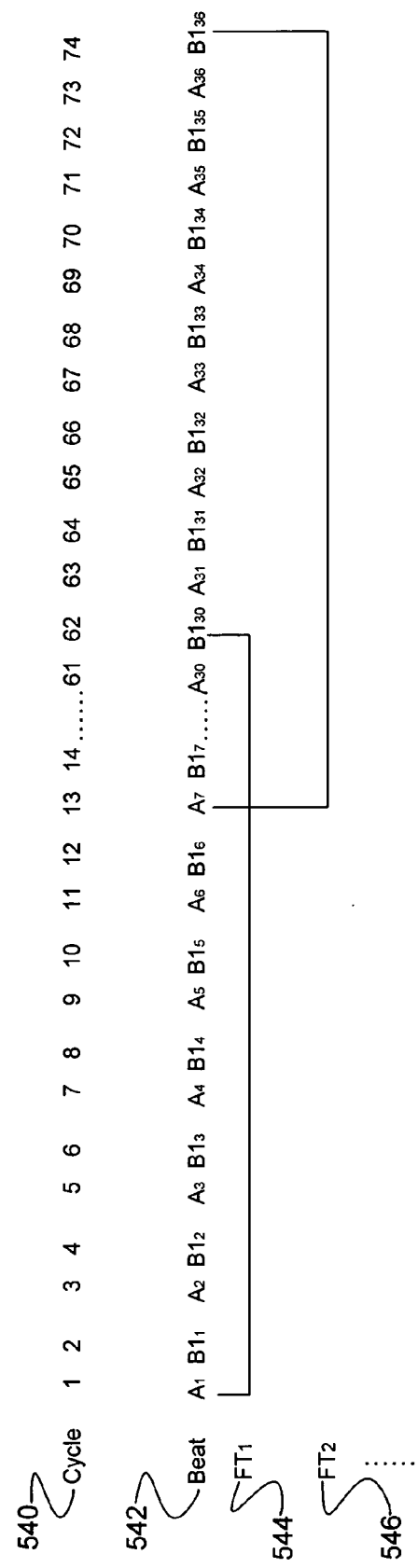
FIG. 16 shows an example of the transformation of beat vector segments from the time domain to the frequency domain according to the present invention.

FIG. 16 shows an example of the transformation of beat vector segments from the time domain to the frequency domain. In this example, the vector A-B1 is shown over a series of 74 cycles. The cycle number is shown in row 540 and the individual beats are shown in row 542. Thus, the first 60-beat segment includes cycles 1–60. A $FT_1$ is performed on this segment, resulting in the frequency domain result $FT_1$ (544). The process is then repeated by moving down 12 cycles to perform the next FT operation. In this example, the next FT operation is performed on cycles 13–72, resulting in the frequency domain result $FT_2$ (546). The process is then repeated until the entire series of beats has been analyzed. Once again, the preferred sample is 60 cycles with a step of 12 cycles. However, other sample sizes and step sizes may also be used to perform the method of the present invention. In a preferred embodiment, a sample of 144 cycles with steps of 12 cycles is used.

Figure 17:
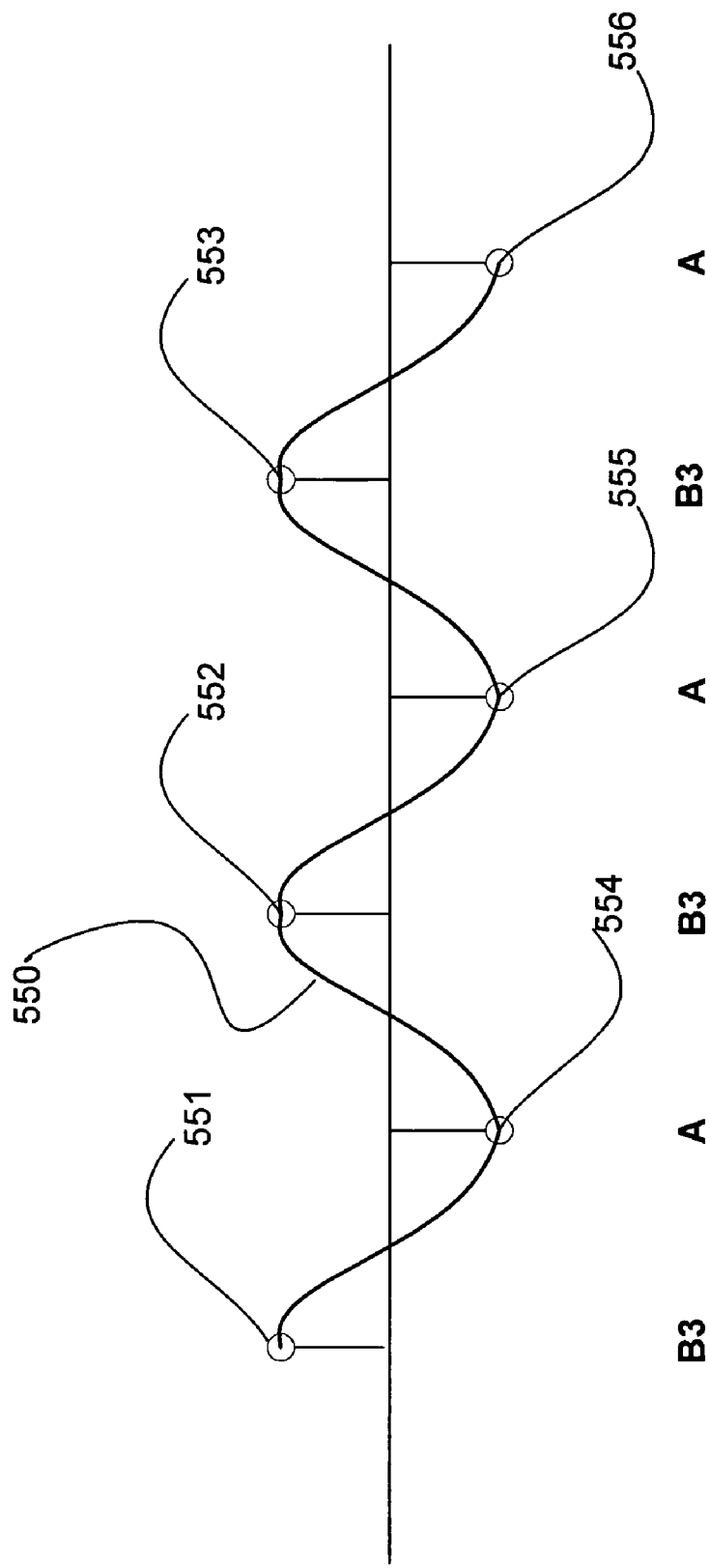
FIG. 17 shows an example of the resulting frequency domain sine wave curve for the beat to beat change for the evaluated vector according to the present invention.

FIG. 17 shows an example of the relationship between the time and the frequency domains for the evaluation of the vector of change between beat B3 and beat A. The X-axis is the sub-sampled series of beats consisting of sequential beats B3 (points 551–553) and A (points 554–556). The Y-axis is the mean T-wave amplitude (voltage) over the 100 ms identified to have the greatest T-wave oscillation. The sine wave curve 550 occurs at 0.5 cycles/sub-sampled beat. This frequency is used to identify the vector change from beat B3 to beat A. The magnitude of the sine wave is half the absolute change of the mean T-wave amplitude over the 100 ms segment from beat B3 to beat A. The phase of the sine wave identifies that there is a decrease in the mean T-wave amplitude over the 100 ms segment when moving from beat B3 to beat A. Note that a 180° phase shift of curve 550 would identify an increase rather than a decrease in voltage when moving from beat B3 to beat A. The sine wave is identified by applying a Fourier Transformation to the sub-sampled beat series and identifying the magnitude and phase at 0.5 cycles/sub-sampled beat. Hence, this method identifies the vector of change (magnitude and phase) from beat B3 to beat A.

Figure 8A:
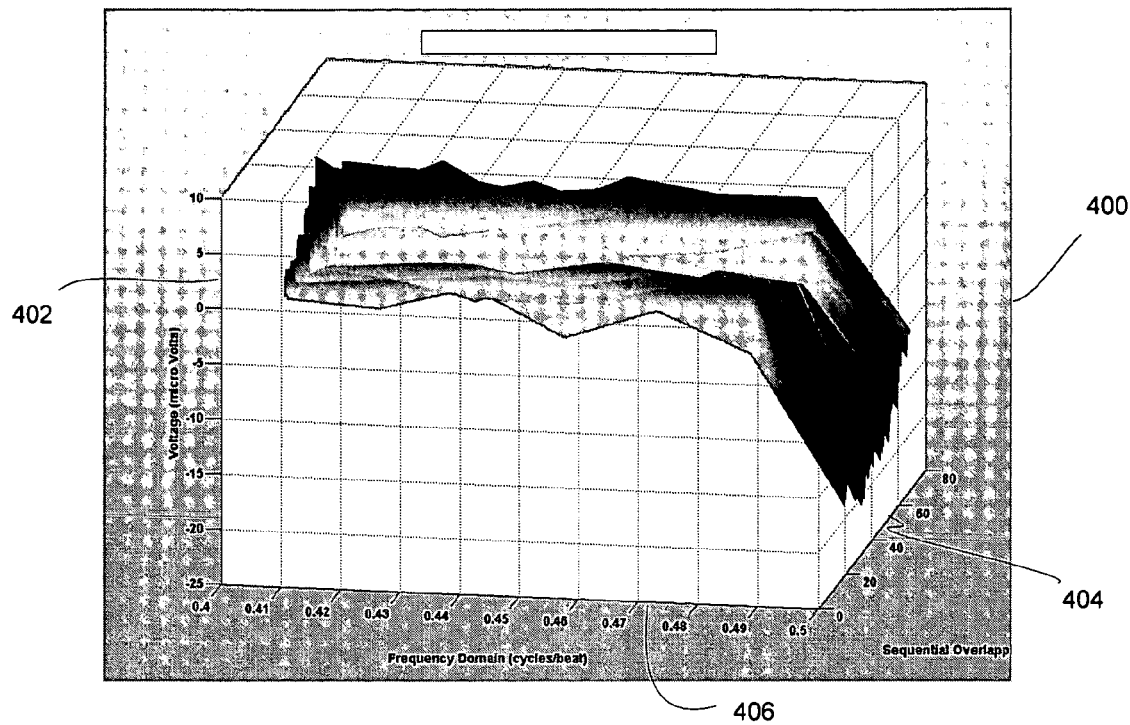
FIG. 8a shows an exemplary graph illustrating the frequency domain impact from a fourth beat to a first premature beat in a first patient according to the present invention.

FIG. 8a shows an exemplary graph 400 illustrating the frequency domain impact of the first premature beat (beat A) from the prior beat (beat B3) in the first patient. The graph is a three dimensional plot with the horizontal axis (406) being the real component of the FT frequency domain. The primary frequency of interest occurs at 0.5 cycles/sub-sampled beat on the right hand side of the plot and represents the vector change from beat B3 to beat A as is illustrated in FIG. 17. The adjacent frequencies to the left are limited to those between 0.4 cycles/beat and 0.5 cycles/beat to give a measure of background noise. However, this measure of background noise is not necessary to the embodiment of this invention since the phase of oscillation is controlled by pacing and the overall impact of pacing may be assessed independent of the background noise. The depth axis (404) is the result of each sequential overlapping series, e.g., the number of 60-beat segments to which the FT was applied. The vertical axis (402) is the voltage in microvolts of each frequency. This graph is the result of the FT performed in step 320 of process 300 on the first of the four vectors identified in step 315 of process 300. The actual mean voltage change in the 100 ms segment of the terminal T-wave with moving from beat B3 to beat A is twice the frequency domain measure as is illustrated in FIG. 17. The alternans signal indicates that the T-wave magnitude is consistently reduced 20–40 microvolts as a result of moving from beat B3 to beat A (twice 10–20 microvolts seen on the graph as discussed above). In the example provided, the graph 400 is for the first patient and the vector B3-A that is the result of the premature beat (A) after the last normal beat (B3).

Figure 8B:
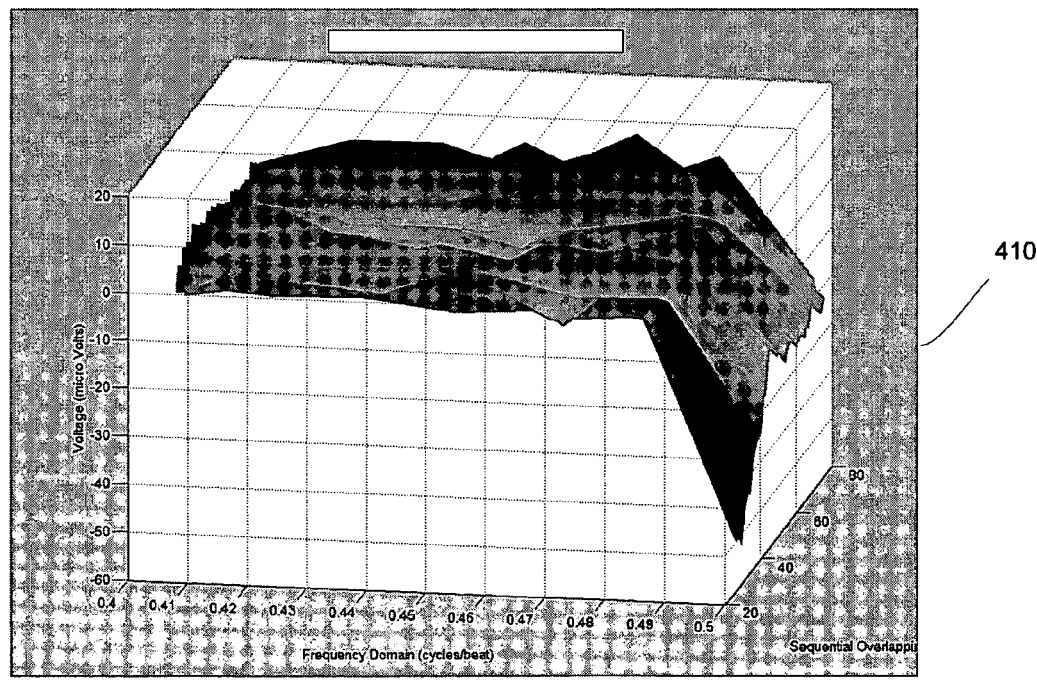
FIG. 8b shows an exemplary graph illustrating the frequency domain impact from a fourth beat to a first premature beat in a second patient according to the present invention.
Figure 9A:
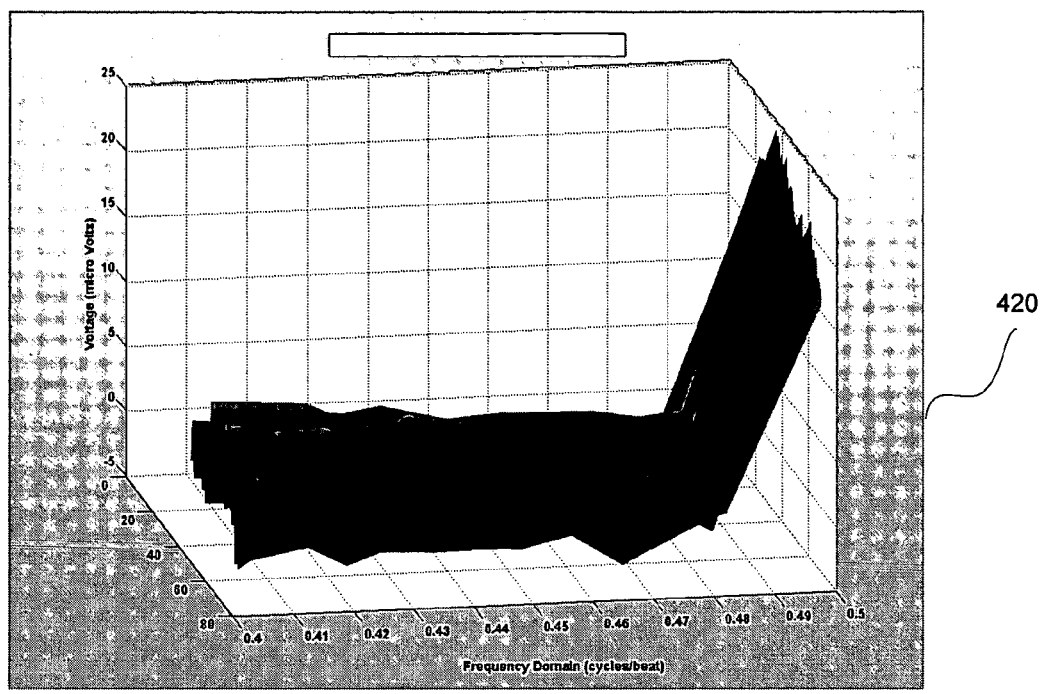
FIG. 9a shows an exemplary graph illustrating the frequency domain impact from a first premature beat to a second beat in a first patient according to the present invention.
Figure 9B:
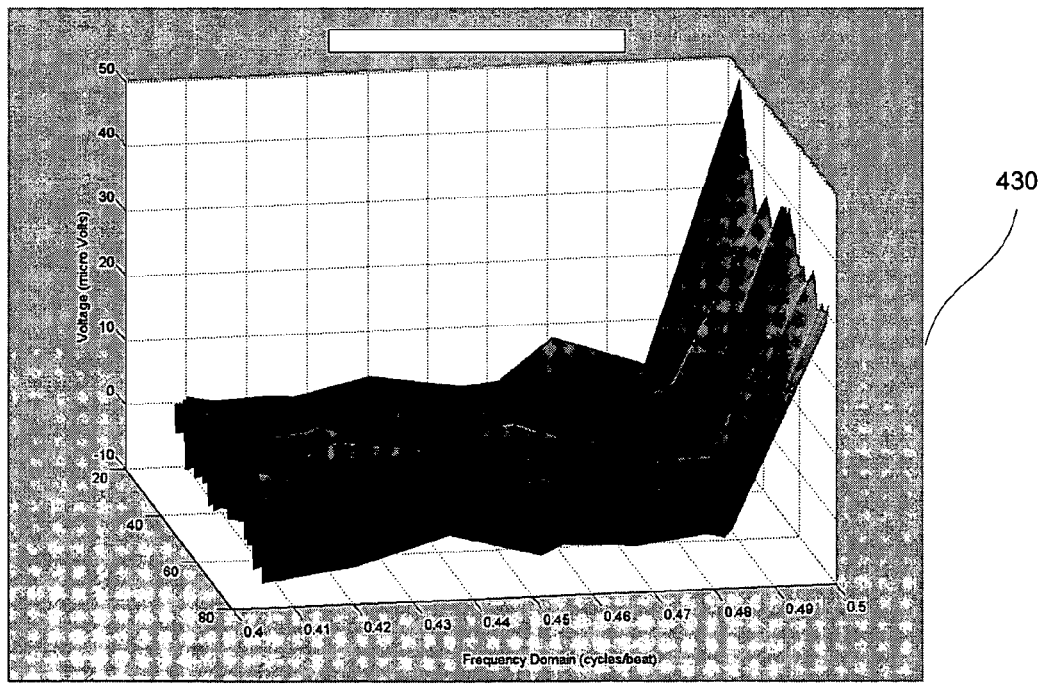
FIG. 9b shows an exemplary graph illustrating the frequency domain impact from a first premature beat to a second beat in a second patient according to the present invention.
Figure 10A:
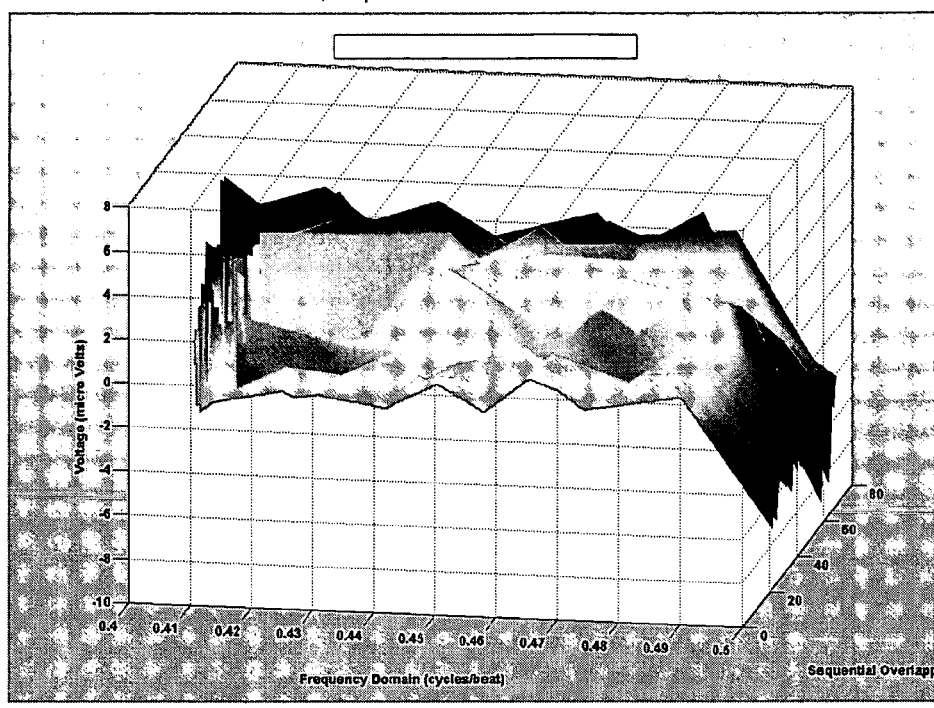
FIG. 10a shows an exemplary graph illustrating the frequency domain impact from a second beat to a third beat in a first patient according to the present invention.
Figure 10B:
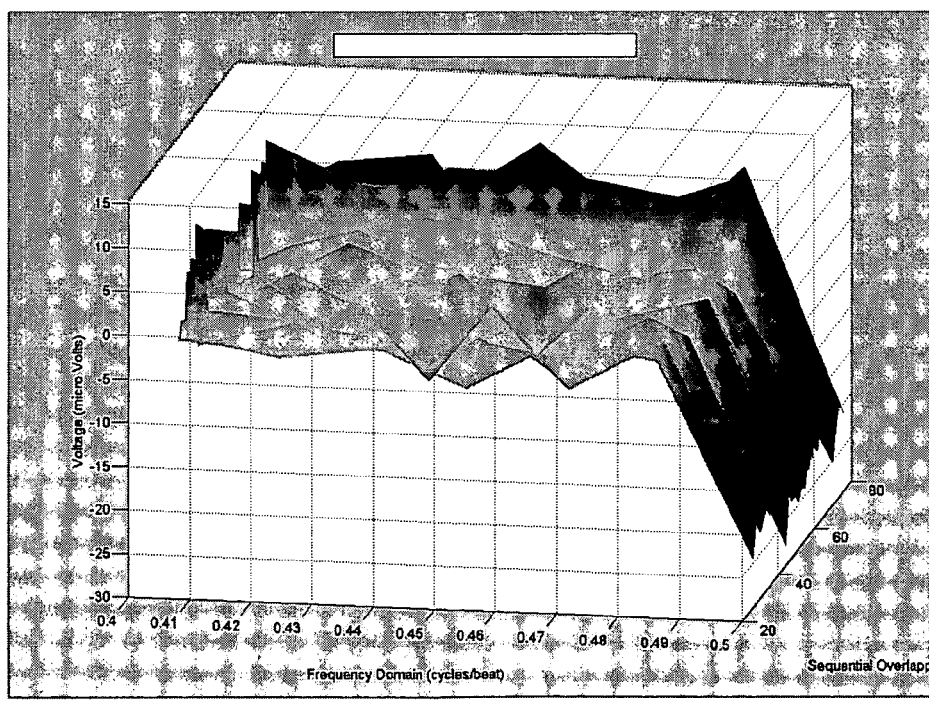
FIG. 10b shows an exemplary graph illustrating the frequency domain impact from a second beat to a third beat in a second patient according to the present invention.
Figure 11A:
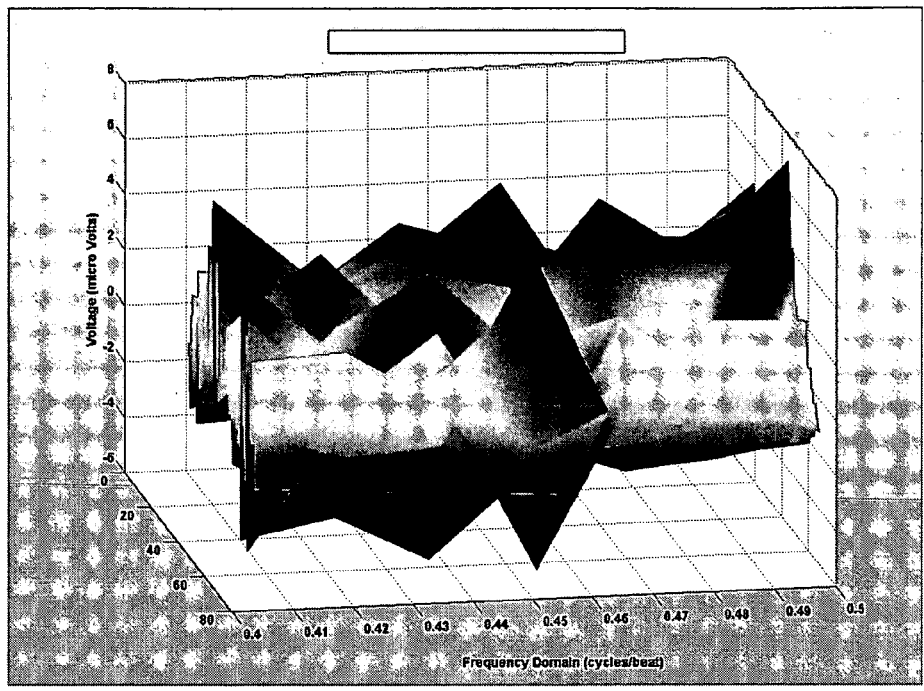
FIG. 11a shows an exemplary graph illustrating the frequency domain impact from a third beat to a fourth beat in a first patient according to the present invention.
Figure 11B:
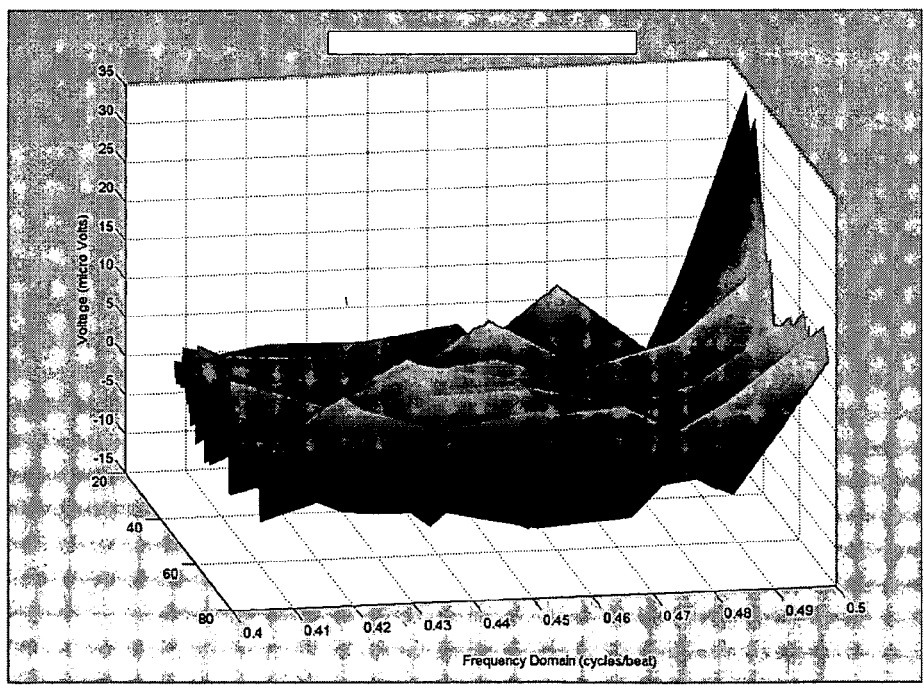
FIG. 11b shows an exemplary graph illustrating the frequency domain impact from a third beat to a fourth beat in a second patient according to the present invention.

Similarly, FIG. 8b shows an exemplary graph 410 illustrating the frequency domain impact of the first premature beat (Beat A) from the prior beat (Beat B3) in the second patient. The graph 410 is obtained in the same manner as the graph 400 and shows the same information for the second patient as described above for the first patient with respect to graph 400. FIG. 9a shows an exemplary graph 420 illustrating the frequency domain impact from the premature beat (Beat A) to the second beat (Beat B1) in the first patient. FIG. 9b shows an exemplary graph 430 illustrating the frequency domain impact from the premature beat (Beat A) to the second beat (Beat B1) in the second patient. FIG. 10a shows an exemplary graph 440 illustrating the frequency domain impact from the second beat (Beat B1) to the third beat (Beat B2) in the first patient. FIG. 10b shows an exemplary graph 450 illustrating the frequency domain impact from a second beat (Beat B1) to the third beat (Beat B2) in the second patient. FIG. 11a shows an exemplary graph 460 illustrating the frequency domain impact from the third beat (Beat B2) to the fourth beat (Beat B3) in the first patient. FIG. 11b shows an exemplary graph 470 illustrating the frequency domain impact from the third beat (Beat B2) to the fourth beat (Beat B3) in the second patient. Those of skill in the art will understand that each of the graphs 420, 430, 440, 450, 460 and 470 are created in the same manner as described above for graph 400. Each graph represents the frequency domain data for a particular sub-sampled beat series for the identified patient.

Referring back to FIG. 7c, the next step 325 is used to identify the alternans vector related to each of the beats in the pattern. The alternans vectors labeled as Valt1, Valt2, Valt3 and Valt4 correspond to the vectors B3-A, A-B1, B2, and B2 B3, respectively at 0.5 cycles/sub-sampled beat. Thus, Valt1 is the vector of the voltage change of the FT of beat B3 to beat A found at 0.5 cycles/sub-sampled beat in the frequency domain. Referring to the graph 400 of FIG. 8a, it can be seen that the Valt1 for the first patient is shown as the voltage in micro Volts (axis 402) at the value of 0.5 cycles/sub-sampled beat (axis 406). The Valt1 may be considered the average of each of the values of the sequential overlapping 60-beat segments. Those of skill in the art will understand that the Valt1 for the second patient may be obtained in the same manner from the graph 410.

The process is then repeated to find each of Valt2, Valt3 and Valt4 by identifying the 0.5 cycles/beat in the frequency domain for the remaining vectors A-B1, B1-B2, and B2-B3. Once again, those of skill in the art will understand that the graphs 420–470 may be used to determine the corresponding of Valt2, Valt3 and Valt4 for each patient in the same manner as described above for Valt1 for the first patient.

Figure 12A:
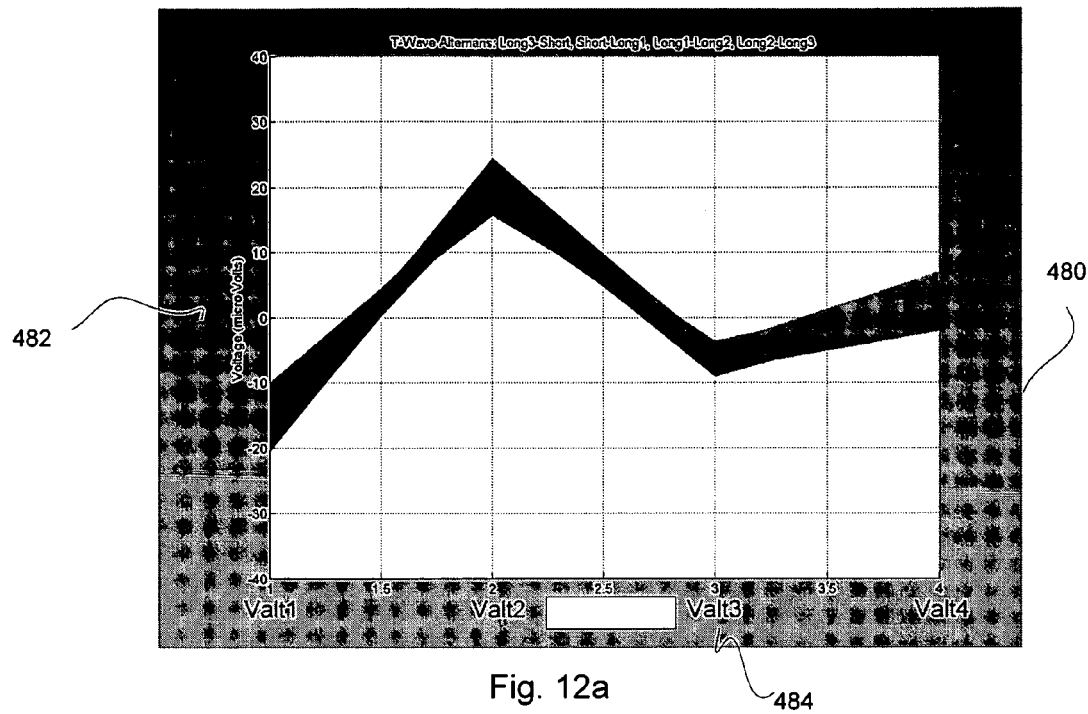
FIG. 12a shows an exemplary graph illustrating the TWA voltage change in response to a 4-beat resonant pacing pattern in a first patient according to the present invention.
Figure 12B:
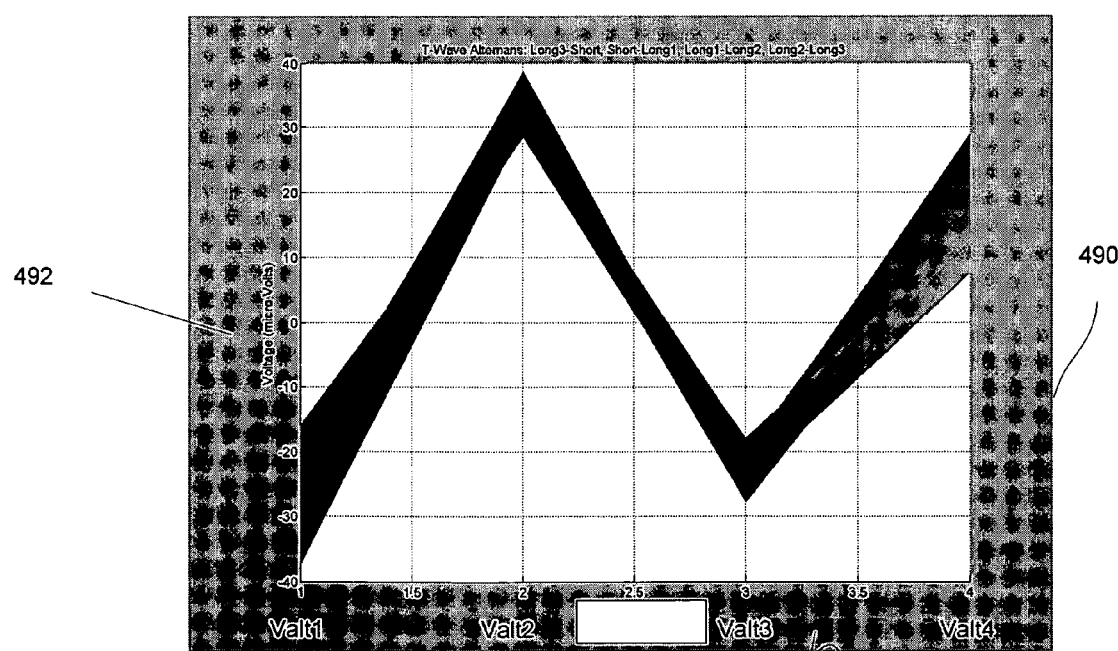
FIG. 12b shows an exemplary graph illustrating the TWA voltage change in response to a 4-beat resonant pacing pattern in a second patient according to the present invention.

FIG. 12a shows an exemplary graph 480 illustrating the alternans vectors over the 4-beat resonant pacing pattern in the first patient. Each of the Valt1, Valt2, Valt3 and Valt4 (axis 482) as determined above may be shown over the beat resonant pacing pattern (axis 484). Similarly, FIG. 12b shows an exemplary graph 490 illustrating the alternans vectors over the 4-beat resonant pacing pattern in the second patient. Each of the Valt1, Valt2, Valt3 and Valt4 (axis 492) as determined above may be shown over the 4-beat resonant pacing pattern (axis 494). Thus, graphs 480 and 490 show the repolarization oscillation induced by the slightly premature beat over the four beats of exemplary pacing pattern 50. The graphs 480 and 490 show that Valt1 is the vector of change of the T-wave from beat B3 to the premature beat A which induces a reduction of the T-wave amplitude in the region of interest that was identified as having the maximum oscillation for the particular patient.

Figure 18:
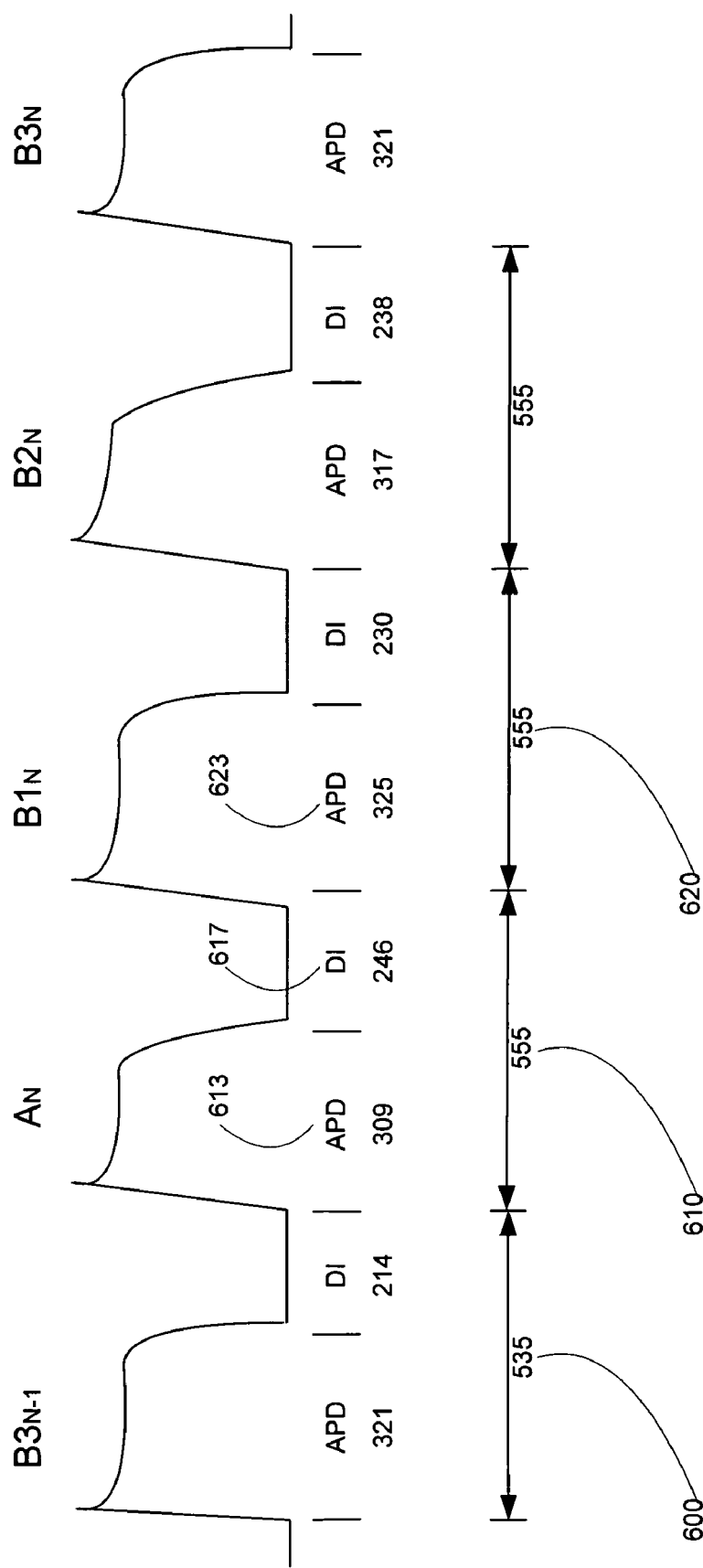
FIG. 18 shows five beats of an exemplary 4-beat resonant pacing pattern according to the present invention.

The electrical restitution relationship that resulted in the reduction of the T-wave for Valt1 has an impact on the subsequent T-wave. This may again be explained in terms of the electrical restitution relationship where the prior diastolic interval impacts the subsequent action potential duration. The interaction of the pacing pattern and electrical restitution is described with reference to FIG. 18 which shows five beats of the exemplary 4-beat resonant pacing pattern from beat $B3_{N-1}$ through beat $B3_N$, where N is the loop number of the pattern. This exemplary figure shows the four beats of loop N and the last beat of loop N−1. Shortening of the action potential duration ("APD") 613 of beat A (309 ms) results in a longer diastolic interval ("DI") 617 after beat A (246 ms). Also, the CL 610 is returned to 555 ms giving the diastolic interval an additional 10 ms over the prior CL 600 (535 ms). This results in the longer APD 623 after beat B1 (325 ms) and larger amplitude of the terminal T-wave. The electrical restitution relationship describes the expected APD using the formula:

$$APD_N \cong m * DI_{N-1} + B$$

where: m is the slop of the restitution curve; and
B is the y intercept of the restitution curve This relationship becomes important because the steeper the restitution curve, the more likely it is that the patient will experience VF. The magnitude of the change of the T-wave as a result of the premature beat is a reflection of the slope of the restitution curve, i.e., a steeper restitution curve results in a greater change of the T-wave due to a greater change of the APD as shown by the formula above. A steeper restitution curve also causes greater buildup of oscillation resulting in a greater chance of VF for the patient.

A comparison of the graphs 480 and 490 of FIG. 12 shows that the pacing pattern induces a much greater oscillation in the second patient (i.e., the patient with a history of heart failure and coronary artery disease). In addition, the graphs 480 and 490 also show that the oscillations decay much faster in the first patient (i.e., the patient exhibiting no signs of any cardiac disease) than the second patient. As described above, the magnitude of oscillations and the decay rate of oscillations are measures of electrophysiologic stability and a smaller oscillation with a faster decay rate indicates a more stable system.

Similar to the preceding two processes, the user has the choice of working in the time domain and/or the frequency domain in step 330. If the user decides to work in the frequency domain, the process continues to step 335 where the time domain data is converted to frequency domain data using a process such as an inverse Fourier transformation. The process continues to step 340 where the frequency domain stability indices are determined. These indices may be the same as described above with reference to the process 250 of FIG. 7a. If the user desires to work in the time domain, the process continues to step 345 where the time domain stability indices are determined. These indices may be the same as described above with reference to the process 250 of FIG. 7a.

To expand on the indices described above, the electrophysiologic stability may be measured by calculating indices that measure the response to pacing and overall alternans. These indices are calculated from the primary result which is the time and frequency domain representations of the response to pacing. They include the overall Valt, Valt2, Valt4, dValt/dt, the T-wave stability index (TWSI). Each of these measures may be normalized to the magnitude of a component of the electrogram since the magnitude of TWA has been shown to be dependent on the magnitude of the T-wave. The TWSI which, as described above, is an index of the decay rate of oscillations relative to the magnitude of background oscillations induced by pacing. The TWSI is an indicator of relative electrophysiologic stability of the patient's heart where a smaller TWSI indicates a slower decay rate of oscillations relative to pacing induced oscillations and hence a less stable system. The first step in calculating the TWSI is to determine the decay rate of oscillation, dValt/dt. An exemplary method for the calculation of dValt/dt utilizes the vectors Valt2 and Valt4. Valt2 reflects the oscillation induced by both the premature beat and the post-premature beat while Valt4 reflect the oscillations present after a time period for oscillation decay. Hence, the measure dValt equals Valt2−Valt4. The measure dt equals the time interval between from beat B1 to beat B3 which is 1110 ms, i.e., 555 ms+555 ms. Thus, dValt/dt equals (Valt2−Valt4)/1.11 microVolt/second. Pacing induced oscillations (Valt) after a time period for decay of oscillations may be measured as Valt4. The TWSI is then calculated as (dValt/dt/Valt4 which reduces to (Valt2−Valt4)/ (1.11*Valt4).

The following is an exemplary calculation of the TWSI for the first and second patients using the exemplary data as presented in graphs 480 (FIG. 12a) and 490 (FIG. 12b), respectively:

Patient 1:
Valt2=20 micro Volts
Valt4=5 micro Volts dValt/dt=(Valt2−Valt4)/1.11 micro Volts/second
dValt/dt=(20−5)/1.11=15/1.11=13.5
TWSI=(Valt2−Valt4)/(1.11*Valt4)
TWSI=(20−5)/(1.11*5)=2.7
Patient 2:
Valt2=32 micro Volts
Valt4=18 micro Volts
dValt/dt=(Valt2−Valt4)/1.11 micro Volts/second
dValt/dt=(32−18)/1.11=14/1.11=12.6
TWSI=(Valt2−Valt4)/(1.11*Valt4)
TWSI=(32−18)/(1.11*18)=0.7

As can be seen from the above calculations, the first patient (i.e., the patient exhibiting no signs of any cardiac disease) has a much higher TWSI than the second patient (i.e., the patient with a history of coronary artery disease). In the above example, the TWSI of patient 1 is 3.86 times the TWSI of patient 2. Thus, when a cardiologist receives the TWSI using the diagnostic method according to the present invention, the cardiologist may determine the stability of the patient's heart, the patient's risk factor for complications such as VT/VF and the degree of cardiomyopathy in the patient. The TWSI is one measure that may be derived from the exemplary method. Other measures that may provide prognostic information that may also be derived these data are the mean magnitude of alternans, the response to the early beat, Valt2, slope of oscillation decay, the magnitude of the terminal oscillation, Valt4, the magnitude of oscillation relative to the area under the T-wave. Those of skill in the art will understand that there may be many measures of stability assessment and that the TWSI is only one measure of stability. Other examples of stability have been described above.

The following includes additional examples of stability indices. When a patient is paced with a 4-beat resonant pacing, the resultant dValt/dt derived from the final time data and the magnitude of the 0.25 cycles/beat frequency derived from the final frequency data are measures of the decay rate of pacing induced oscillations. Similarly, Valt4 derived from the time data and the magnitude of the 0.5 cycles/beat frequency derived from the frequency data are measures of oscillations induced by pacing. As described above all three of the exemplary methods 250, 300 and 700 may be used to generate final time data and final frequency data. A measure of stability in the frequency domain that that is similar to the TWSI derived from the time domain data is the magnitude at 0.25 cycles/beat divided by the magnitude at 0.5 cycles/beat. The In the examples above, this yields 2.93 for patient one and 0.34 for patient two. The ratio of these results is 8.4:1. Similarly, parameters derived from the final frequency domain may be used to differentiate normal from marginal electrophysiologic stability. Those of skill in the art will understand that the time domain data and the frequency domain data may be used in conjunction. For example, the physician may read the frequency data and determine that there is a decrease in electrophysiologic stability. However, the physician may then desire to see the time data to see the results on a beat-by-beat basis to verify the findings, fully understand the phenomena, or determine a course of treatment for the patient.

Thus, the exemplary diagnostic method according to the present invention uses a pacing pattern to dynamically induce oscillations of repolarization and then allows a time period for observation of oscillation decay. The pacing pattern is designed so that the timing of the irregularity in the cycle length resonates with repolarization oscillations of past beats to create a greater magnitude of oscillations in hearts with marginal T-wave stability and a decay of oscillations in hearts with normal T-wave stability. The impact of the pacing pattern is recorded on electrograms and then the pattern is analyzed with signal processing. The method then quantifies magnitude of oscillations due to pacing and the ability of the heart to suppress oscillations. Indices are used to maximally differentiate normal from abnormal electrophysiologic stability and create a scale that can identify small incremental changes in electrophysiologic stability through time for monitoring purposes.

Furthermore, while the above has been described with respect to pacing, and more specifically resonant pacing as defined above, the diagnostic method is not limited to monitoring the effects of resonant pacing. The diagnostic method may also be used to monitor the heart system when non-resonant pacing is used, when a constant pacing is used or when the native heartbeat is being monitored. As described above, resonant pacing should produce the effect that there are no phase inversions in the measurement of the beats on the electrogram. Thus, for resonant pacing, the stimulus of pacing corrects any phase inversions. In contrast, non-resonant pacing, constant pacing and native heartbeats may have resulting phase inversions. Thus, in these cases, the phase inversions will be corrected through the computational method for analyzing the heartbeat. This computational method for correcting for phase inversions is more fully described with reference to step 180 of FIG. 5*a*.

In addition to the diagnostic method described above, the exemplary embodiments of the present invention may also include a therapeutic method. Specifically, the pacing patterns described previously may reduce a patient's risk of developing VT/VF. Patients that have a more normal amount of heart rate variability have a lesser degree of mortality when heart failure occurs. Patients who have heart failure and require cardiac pacing generally receive cardiac pacing with a constant CL. This reduces their heart rate variability to essentially zero. The impact of reducing heart rate variability to a minimal amount with cardiac pacing in heart failure remains unknown, but may be detrimental and increase the risk of VT/VF or progression of heart failure. Thus, the programmed resonant and non-resonant pacing patterns described above may introduce a degree of heart rate variability into the patient and decrease the risk of death from heart disease.

Figure 24:
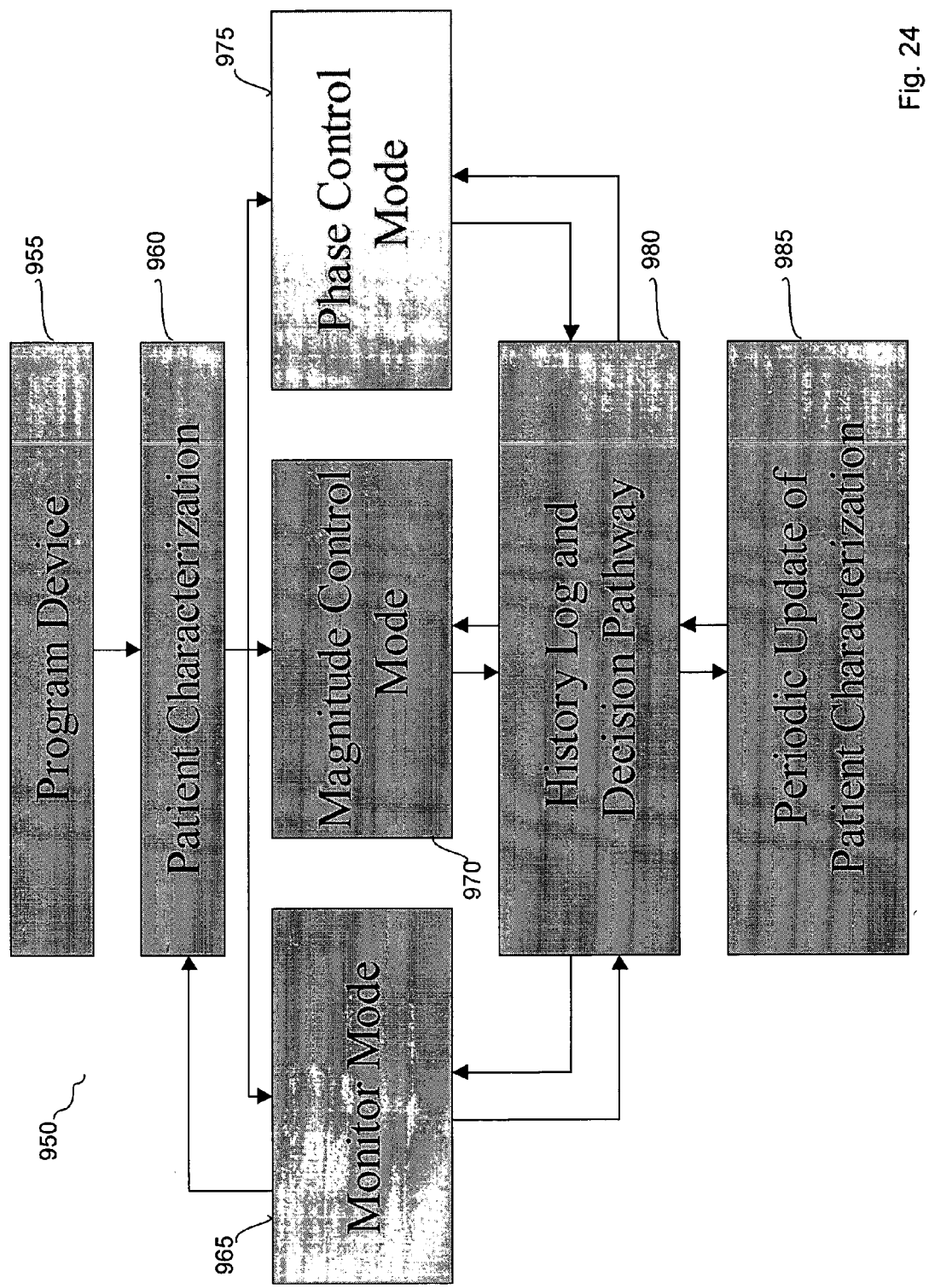
FIG. 24 shows an exemplary therapeutic method according to the present invention.

FIG. 24 shows an exemplary therapeutic method 950 which includes patient monitoring and feedback. In step 955, the pacing device is programmed to include the various methods of pacing that are desired for the patient. FIG. 25 shows an exemplary input form 1000 which may be used to program the pacing device. The input form 1000 shows the various choices which a physician may make to program the pacing device for the present invention. In the first field 1010, the physician may choose the patient characterization options including, steady state response, non-resonant pacing, resonant pacing and a template of responses. The patient characterization will be described in greater detail below. However, it should be noted that the physician may choose any or all of the options.

In the second field 1020, the physician may choose the operation mode and the order of operation for the pacing device. The modes which will be described in greater detail below include a monitoring mode, a magnitude control mode and a phase control mode. The third field 1030 allows the physician to set a heart rate maximum and a mode for alternans. The final field 1040 includes settings for responses to premature beats. Those of skill in the art will understand that the form 1000 is only exemplary and that there may be other settings that can be set for the pacing device.

Referring back to FIG. 24, the method continues to step 960 where the patient is characterized. The patient characterization step 960 includes analysis of the patients native rhythm using the fiduciary and phase synchronization steps described above, and providing the various pacing patterns to the patient and determining the patient's response to these pacing patterns. These various responses are then stored in a template of responses. In a first characterization the system is tested to determine its steady state response, including the magnitude and phase of the steady state response. In a second characterization the system is tested to determine its response to resonant pacing, including the magnitude and phase of the response. The same process is carried out for non-resonant pacing. In addition, various impulses are supplied to the system to determine the impact of the impulses on the system. More specifically, the patient's the open-loop impulse response is determined by obtaining a desired phase and magnitude of alternans by varying the pacing pattern, e.g., resonant pacing, and/or heart rate, then applying an impulse consisting of a change in cycle length or pacing amplitude to the heart followed by constant pacing. The phase and magnitude of the oscillations during constant pacing is then analyzed. This process is repeated to obtain an adequate signal for the impulse response under a set of conditions, e.g., phase and magnitude of alternans, and heart rate. Determination of the impulse response is then determined for various initial conditions. The various responses to the different pacing patterns and impulses are stored in a template for further use.

The process then continues to one of the control modes 965, 970 or 975 based on the selection by the physician. The monitor mode 965 will be described first. In the monitoring mode, the steady state response of the system will be monitored. If the alternans exceeds a defined threshold as measured by the time domain or frequency domain data, the monitoring mode may indicate via an output the state of the system. It may also automatically change the current mode to another mode, e.g., magnitude control mode 970 or phase control mode 975. The monitoring mode also monitor for other conditions such as PVC and characterize the PVC morphology, e.g., the magnitude and phase of alternans for pre and post PVC beats, etc. This may also trigger a switch to a different phase.

The magnitude control mode 970 allows the pacing device to control the magnitude of the repolarization alternans. If the magnitude exceeds a defined threshold, the pacing device may increase the cycle length of pacing or deliver a non-resonant pacing pattern based on the patient characterization of responses to various non-resonant pacing patterns which may be stored in the template. The pacing device may compare the current magnitude and phase with stored values to select the most appropriate non-resonant pacing pattern. If the magnitude continues to exceed the threshold, the pacing pattern may be changed to another non-resonant pattern or switched to a closed loop control strategy to reduce the magnitude of alternans. This strategy consists of determining the magnitude and phase of alternans and delivering an impulse, the impulse consists of a cycle length variation or pacing amplitude. The impulse is selected from the template of responses to modulate the magnitude and phase of ongoing alternans. The impulse may be selected to have a proportionate reduction of the level of ongoing alternans, e.g., a 10–20% reduction in the magnitude of alternans for a given pulse. Re-detection of the magnitude and phase of alternans is then performed. A determination is made whether the impulse had the anticipated response. Then another impulse is delivered based on the ongoing magnitude and phase of alternans and the template of responses. The process is repeated and an overall assessment of the degree of alternans control is determined. A decision is then made as to whether the control strategy is successful and whether to change the pacing mode or other pacing parameters based on pre-programmed parameters and a log of the patient's responses.

Examples of non-resonant cardiac pacing patterns are described with reference to FIGS. 4a–g. In this example, the exemplary 3-beat pacing pattern 85 as shown in FIG. 4a will be considered. As shown in FIG. 4a, the 3-beat pacing pattern 85 includes a premature beat (Beat A) two normal beats (Beats B,C). The 3-beat pacing pattern 85 (or any non-resonant pacing pattern) that does not resonate with repolarization alternans may reduce the magnitude of repolarization alternans. As described above, the magnitude of oscillation of the repolarization alternans is an indicator of risk and may be a direct precipitant of VT/VF. Therefore, the reduction of the magnitude of these oscillations may decrease the risk associated with the repolarization alternans. Mechanisms of initiating ventricular arrhythmias may vary dependant on an individual's electrophysiologic substrate. Whereas the resonant pacing pattern described above prevents the genesis of spatially discordant alternans, the non-resonant pacing pattern may reduced the magnitude of alternans and potentially prevent arrhythmias initiated by after depolarizations or other mechanisms. Hence, both resonant and non-resonant pacing patterns may be important in producing heart rate variability that creates anti-arrhythmic preconditioning according to an individual's particular electrophysiologic substrate.

Referring back to FIG. 6c electrogram 220 and FIG. 21b curve 812 show the reaction of the second patient (i.e., the patient with a history of heart failure and coronary artery disease) to a steady state pacing pattern. As shown in electrogram 220 and curve 812, the patient exhibits a marked TWA in the repolarization region 224 and oscillations of repolarization at 0.5 cycles/beat in the frequency spectra curve 812. Thus, the electrogram 220 and curve 812 indicate that the patient has some instability in the heart because of the presence of the TWA as measured by two different methods. However, referring to FIG. 6e electrogram 240 and FIG. 23b curve 852 show the response of the same patient to the 3-beat non-resonant pacing pattern (545 ms, 555 ms, 555 ms). As shown in electrogram 240 and curve 852, magnitude of the TWA in the repolarization region 244 and oscillations of repolarization at 0.5 cycles/beat in the frequency spectra of curve 852 has been significantly reduced from the TWA in electrogram 220 and the frequency spectra of 0.5 cycles/beat of curve 812. Thus, FIG. 6e and FIG. 23b show that a non-resonant pacing pattern, specifically a 3-beat pattern, can reduce the magnitude of the TWA in the repolarization region, thereby decreasing the patient's risk attributable to the presence of TWA.

The phase control mode 975 allows the pacing device to control the phase of the repolarization alternans. An exemplary resonant pattern is the 4-beat resonant pacing pattern 50 described with reference to FIG. 2. The input to the system is the cycle length between beats. The output of the system is the action potential that includes the T-wave as a manifestation of repolarization in the electrogram. Resonant temporal pacing results in an increase in heart rate variability. Repolarization alternans may occur out of phase in different regions of the heart, i.e., the apex of the heart may oscillate in a long-short pattern while the base of the heart oscillates in a short-long pattern. This phenomenon is called spatially discordant alternans and results in a large gradient of repolarization that is thought to be pro-arrhythmic by leading to functional block that may initiate of reentrant VT around scar (Pastore J M, Rosenbaum D S., "Role of structural barriers in the mechanism of alternans-induced reentry.", Circulation Research 2000; 87: 1157–1163) or figure of 8 reentry induction of VF (Pastore J M, Girouard S D, Laurita K R, et. al., "Mechanism Linking T-Wave Alternans to the Genesis of Cardiac Fibrillation," *Circulation* 1999; 99: 1385–1394). Spatially concordant alternans is said to occur if both regions of the heart are oscillating in phase. This is thought to be a less pro-arrhythmic condition due to a smaller gradient of repolarization between regions of the heart. If a pacing pattern results in both regions of the heart oscillating in phase (spatially concordant alternans) the gradient of repolarization may be significantly reduced. Pacing that results in converting spatially discordant alternans into spatially concordant alternans may have an antiarrhythmic effect by decreasing the gradient of repolarization. Hence, incorporation of a resonate pacing pattern into a cardiac pacemaker may introduce beneficial heart rate variability and may decrease the development of the pro-arrhythmic condition of discordant spatially alternans that has been shown to precipitate VT/VF. Other examples of resonant pacing patterns are provided in FIGS. 3a–e.

The phase control mode delivers a resonant pacing pattern based on the template of responses. The magnitude and phase of the response is measured to determine if the pacing pattern is delivering the expected response. If the system is having the expected response, the resonant pacing pattern is continued. If the expected response is not being measured, the pacing pattern may be changed by modulating the variation in cycle length, i.e., the size of the impulse, or changing to another resonant pattern. If an arrhythmia or other unfavorable dynamics are detected, then pacing may be changed to a longer mean cycle length, or a different pacing strategy. Again, the template includes the patient response to various pacing patterns and impulse responses and the pacing device will apply the most appropriate pattern or pacing strategy. The method may then continuously feedback the current magnitude and phase and the pacing pattern and/or impulses will be adjusted to continuously control the phase.

As can be seen from the above description, the modes have various feedback loops to adjust the control of the pacing device to achieve the desired control for the patient. The step 980 allows for the recording of the history for the device and the patient's reaction to the various control modes. The step 985 provides for periodic updates of the patient characterization to keep the templates updated so that the proper input may be given to the patient.

In the preceding specification, the present invention has been described with reference to specific exemplary embodiments thereof. It will, however, be evident that various modifications and changes may be made thereunto without departing from the broadest spirit and scope of the present invention as set forth in the claims that follow. The specification and drawings are accordingly to be regarded in an illustrative rather than restrictive sense.

What is claimed is:

1. A method, comprising the step of delivering a resonant pacing pattern to a heart.

2. The method of claim 1, wherein the heart has a plurality of oscillators producing an oscillation, wherein a variation of the resonant pacing pattern resonates with each of the oscillators, thereby synchronizing the phase of oscillation of each of the oscillators to the resonant pacing pattern.

3. The method of claim 2, wherein the oscillators include one of a cardiac alternans and a repolarization alternans.

4. The method of claim 2, wherein the variation is one of a temporal and amplitude variation.

5. The method of claim 1, wherein the resonant pacing pattern is one of a 2-beat, a 4-beat, a 6-beat, an 8-beat, a 10-beat and a 12-beat pacing pattern.

6. The method of claim 1, wherein the resonant pacing pattern has a high magnitude of frequency content in a frequency region of each of a plurality of oscillators of the heart.

7. The method of claim 6, wherein the resonant pacing pattern increases a magnitude of oscillation of each of the oscillators.

8. The method of claim 1, wherein the resonant pacing pattern induces a first low amplitude oscillation in a first pattern cycle and then induces a second low amplitude oscillation in a second pattern cycle, the second low amplitude oscillation being in-phase with the first low amplitude oscillation.

9. The method of claim 1, further comprising the steps of:
changing a variation of one of a cycle length and a pacing amplitude of the resonant pacing pattern; and
determining a response of the heart to the variation of the one of the cycle length and the pacing amplitude.

10. A cardiac pacing device, comprising:
a pulse generator producing pacing pulses for delivery to a heart;
a controller generating a signal to control the pulse generator, wherein the signal controls the pulse generator to produce pacing pulses with a resonant pacing pattern; and
an electrode placed within the body delivering the pacing pulses with the resonant pacing pattern to the heart.

11. A method, comprising the step of delivering a non-resonant pacing pattern to a heart.

12. The method of claim 11, wherein the heart has a plurality of oscillators producing an oscillation, wherein a variation of the non-resonant pacing pattern does not resonate with each of the oscillators, thereby reducing a magnitude of the oscillation.

13. The method of claim 12, wherein the oscillators include one of a cardiac alternans and a repolarization alternans.

14. The method of claim 12, wherein the non-resonant pacing pattern sequentially inverts the phase of the oscillators.

15. The method of claim 12, wherein the variation is one of a temporal and amplitude variation.

16. The method of claim 11, wherein the non-resonant pacing pattern is one of a 3-beat, a 5-beat, a 7-beat, a 9-beat and an 11-beat pacing pattern.

17. The method of claim 11, wherein the non-resonant pacing pattern has a low magnitude of a frequency content in a frequency region of each of a plurality of oscillators of the heart.

18. The method of claim 11, wherein the non-resonant pacing pattern induces a first low amplitude oscillation in a first pattern cycle and then induces a second low amplitude oscillation in a second pattern cycle, the second low amplitude oscillation being 180 degrees out of phase with the first low amplitude oscillation.

19. The method of claim 11, further comprising the steps of:
changing a variation of one of a cycle length and a pacing amplitude of the non-resonant pacing pattern; and
determining a response of the heart to the variation of the one of the cycle length and the pacing amplitude.

20. A cardiac pacing device, comprising:
a pulse generator that produces pacing pulses for delivery to a heart;
a controller generating a signal to control the pulse generator, wherein the signal controls the pulse generator to produce pacing pulses with a non-resonant pacing pattern; and
an electrode placed within the body delivering the pacing pulses with the non-resonant pacing pattern to the heart.

21. A method, comprising the steps of:
delivering a pacing pattern to a heart, wherein the pacing pattern is one of a resonant pacing pattern and a non-resonant pacing pattern;
measuring a response of the heart to the pacing pattern, the measured response including a series of electrograms representing a plurality of heartbeats of the pacing pattern; and
calculating diagnostic data from the measured response, wherein the diagnostic data includes data in one of a time domain and a frequency domain.

22. The method according to claim 21, wherein the calculating step includes the substep of aligning the measured response to the pacing pattern.

23. The method according to claim 21, wherein the calculating step further includes the substep of synchronizing a phase of the measured response.

24. The method according to claim 21, wherein the calculating step includes the substep of selecting a region of interest in the measured response, the selecting substep including transforming the aligned data into the frequency domain and averaging each of the frequency components of the aligned data.

25. The method according to claim 21, wherein the calculating step further includes the substep of averaging a value of each beat in the pacing pattern.

26. The method according to claim 21, wherein the calculating step includes the substeps of:
determining real components in the frequency domain in a region of interest of the response;
determining imaginary components in the frequency domain in the region of interest of the response; and
determining one of a magnitude and a phase of the response at each frequency of the frequency domain in the region of interest.

27. The method according to claim 21, wherein the calculating step includes the substeps of:
calculating an average voltage for each beat in a region of interest of the response;
reformatting data in the region of interest into vector data;
transforming the vector data into the frequency domain; and
identifying a voltage for each of the vector data.

28. The method according to claim 21, when the diagnostic data is in the time domain, further comprising the step of: determining a time stability index for the heart from the diagnostic data.

29. The method according to claim 28, wherein the time stability index is one of an overall magnitude of alternans, a magnitude of the response to a cycle length variation, a terminal magnitude of alternans in response to the pacing pattern, a first rate of alternans decay, and a second rate of alternans decay relative to the magnitude of alternans.

30. The method according to claim 21, when the diagnostic data is in the frequency domain, further comprising the step of: determining a frequency stability index for the heart from the diagnostic data.

31. The method according to claim 30, wherein the frequency stability index is one of a magnitude response and a phase response at key frequencies.

32. A method, comprising the steps of:
characterizing a patient by measuring responses of a heart;
storing the characterization responses of the heart;
monitoring the patient when a pacing pattern is delivered to the heart; and
controlling one of a magnitude response and a phase response of the heart, wherein the controlling includes delivering one of a resonant pacing pattern and a constant pacing pattern including an impulse when controlling the phase response.

33. The method of claim 32, wherein the responses include one of responses to pacing patterns and a native rhythm.

34. The method of claim 33, wherein the pacing pattern is one of a constant pacing pattern, a resonant pacing pattern, a non-resonant pacing pattern and a constant pacing pattern which includes an impulse.

35. The method of claim 32, wherein the controlling step includes delivering one of a non-resonant pacing pattern and a constant pacing pattern including an impulse when controlling the magnitude response.

36. The method of claim 35, wherein a type of the one of the non-resonant pacing pattern and the constant pacing pattern including the impulse is delivered based on the stored characterization responses.

37. The method of claim 32, wherein a type of the one of the resonant pacing pattern and the constant pacing pattern including the impulse is delivered based on the stored characterization responses.

38. A method, comprising the steps of:
collecting responses of the a heart, the responses corresponding to sequential overlapping groups of beats of the heart;
determining a phase of each of the responses; and
removing one of the beats when the phase of one of the responses is inverted from the phase of a preceding response.

39. The method according to claim 38, wherein the responses are from a native rhythm of the heart.

40. The method according to claim 38, wherein the one of the beats is removed at a location of the inversion.

41. The method according to claim 38, wherein the responses are to a pacing pattern delivered to the heart.

42. The method according to claim 41, wherein the removed one of the beats includes a group of beats corresponding to the pacing pattern.

43. The method according to claim 38, further comprising the step of: analyzing the responses after the one of the beats is removed.

44. The method according to claim 43, wherein the analyzing step produces one of final time domain data and final frequency domain data for the responses.

* * * * *